US011434192B2

(12) United States Patent
Kleinbeck-Riniker et al.

(10) Patent No.: US 11,434,192 B2
(45) Date of Patent: Sep. 6, 2022

(54) PROCESS AND INTERMEDIATES

(71) Applicant: Novartis AG, Basel (CH)

(72) Inventors: Florian Karl Kleinbeck-Riniker, Basel (CH); Benjamin Martin, Basel (CH); Gerhard Penn, Basel (CH); Francesco Venturoni, Basel (CH); Thierry Schlama, Basel (CH); Thomas Ruch, Basel (CH); Thomas Allmendinger, Basel (CH); Bernhard Wietfeld, Basel (CH); Paolo Filipponi, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/452,452

(22) Filed: Jun. 25, 2019

(65) Prior Publication Data

US 2019/0308927 A1 Oct. 10, 2019

Related U.S. Application Data

(62) Division of application No. 15/780,957, filed as application No. PCT/IB2016/057435 on Dec. 8, 2016, now Pat. No. 10,377,697.

(30) Foreign Application Priority Data

Dec. 10, 2015 (EP) .................................... 15199378
Nov. 14, 2016 (EP) .................................... 16198655

(51) Int. Cl.
| | | |
|---|---|---|
| C07C 59/84 | (2006.01) | |
| C07C 67/035 | (2006.01) | |
| C07C 213/08 | (2006.01) | |
| C07C 69/738 | (2006.01) | |
| C07C 313/06 | (2006.01) | |
| C07C 229/34 | (2006.01) | |
| C07D 265/02 | (2006.01) | |
| C07D 207/36 | (2006.01) | |
| C07C 251/40 | (2006.01) | |
| C07C 251/66 | (2006.01) | |
| C07C 51/373 | (2006.01) | |

(52) U.S. Cl.
CPC .......... *C07C 69/738* (2013.01); *C07C 51/373* (2013.01); *C07C 59/84* (2013.01); *C07C 67/035* (2013.01); *C07C 229/34* (2013.01); *C07C 251/40* (2013.01); *C07C 251/66* (2013.01); *C07C 313/06* (2013.01); *C07D 207/36* (2013.01); *C07D 265/02* (2013.01); *C07B 2200/07* (2013.01)

(58) Field of Classification Search
USPC ......................................................... 560/174
See application file for complete search history.

(56) References Cited

U.S. PATENT DOCUMENTS

| | | | |
|---|---|---|---|
| 5,217,996 | A | 6/1993 | Ksander |
| 10,377,697 | B2 | 8/2019 | Kleinbeck-Riniker et al. |

FOREIGN PATENT DOCUMENTS

| | | |
|---|---|---|
| CN | 104557600 A | 4/2015 |
| CN | 105152980 A | 12/2015 |
| CN | 105330569 A | 2/2016 |
| CN | 105601524 A | 5/2016 |
| CN | 105753741 A | 7/2016 |
| CN | 105884656 A | 8/2016 |
| CN | 105924355 A | 9/2016 |
| CN | 106977415 A | 7/2017 |
| CN | 107602399 A | 1/2018 |
| EP | 0511021 A1 | 10/1992 |
| WO | WO2008/031567 A1 | 3/2008 |
| WO | 2008/083967 A2 | 7/2008 |
| WO | 2009090251 A2 | 7/2009 |
| WO | 2010081410 A1 | 7/2010 |
| WO | 2011035569 A1 | 3/2011 |
| WO | 2011088797 A1 | 7/2011 |
| WO | 2012025501 A1 | 3/2012 |
| WO | WO2012/025502 A1 | 3/2012 |
| WO | 2014032627 A1 | 3/2014 |
| WO | 2016119574 A1 | 8/2016 |
| WO | 2016135751 A1 | 9/2016 |

OTHER PUBLICATIONS

Burgess et al. J. Org. Chem. 1992, 1656.*
Soliman et al., "Syntheses in the Naphthalene Series. Part V.* Action of Sulphuric Acid on Substituted Ethyl 7-Phenylacetoacetates," Journal of the Chemical Society, (1954), 4655-4659.
Ksander G.M. et al., Dicarboxylic Acid Dipeptide Neutral Endopeptidase Inhibitors, J. Med. Chem., 1995, 1689-1700, 38.
Lau S.-H et al., Synthesis of a Precursor to Sacubitril Using Enabling Technologies, Org. Lett., 2015, 5436-5439, 17(21), Org. Lett., US.

* cited by examiner

*Primary Examiner* — Ana Z Muresan
(74) *Attorney, Agent, or Firm* — Timothy P. O'Dea

(57) ABSTRACT

The present invention relates to a new chemical synthesis, intermediates and catalysts useful for the preparation of the neprilysin (NEP) inhibitor sacubitril. It further relates to new intermediate compounds and their use for said new chemical synthesis route.

5 Claims, No Drawings

PROCESS AND INTERMEDIATES

RELATED APPLICATIONS

This application is a divisional application of U.S. application Ser. No. 15/780,957, filed on Jun. 1, 2018, which is a national stage application, filed under 35 U.S.C. § 371, of International Application No. PCT/IB2016/057435, filed Dec. 8, 2016, which claims priority to and the benefit of, European Patent Application Nos. EP 16198655.9, filed Nov. 14, 2016, and EP15199378.9, filed on Dec. 10, 2015, the entire contents of which are incorporated herein by reference in their entireties.

FIELD OF THE INVENTION

The present invention relates to a new chemical synthesis route and intermediates useful for the preparation of neprilysin (NEP) inhibitors and their prodrugs, in particular for the NEP inhibitor prodrug sacubitril.

BACKGROUND OF THE INVENTION

The NEP inhibitor prodrug sacubitril (N-(3-carboxyl-1-oxopropyl)-(4S)-(p-phenylphenyl-methyl)-4-amino-(2R)-methyl butanoic acid ethyl ester; IUPAC name 4-{[(1S,3R)-1-([1,1'-biphenyl]-4-ylmethyl)-4-ethoxy-3-methyl-4-oxobutyl]amino}-4-oxobutanoic acid, also known as AHU377) is represented by the following formula (A)

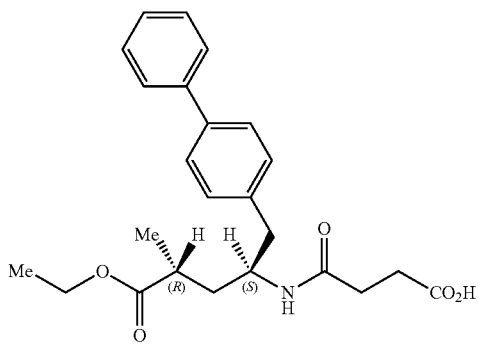

(A)

Sacubitril together with valsartan, a known angiotensin receptor blocker (ARB), forms a sodium salt hydrate complex, known as LCZ696, comprising the anionic forms of sacubitril and valsartan, sodium cations and water molecules in the molar ratio of 1:1:3:2.5, respectively (ratio of 6:6:18:15 in the asymmetric unit cell of the solid state crystal), and which is schematically present in formula (B).

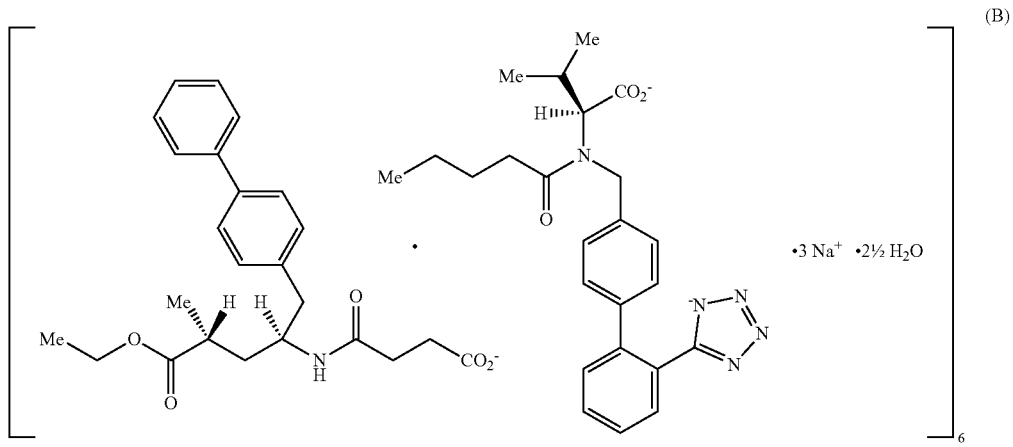

(B)

Said complex is also referred to by the following chemical names: Trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hemipentahydrate or Octadecasodium hexakis(4-{[(1 S,3R)-1-([1,1'-biphenyl]-4-ylmethyl)-4-ethoxy-3-methyl-4-oxobutyl]amino}-4-oxobutanoate) hexakis(N-pentanoyl-N-{[2'-(1H-tetrazol-1-id-5-yl)[1,1'-biphenyl]-4-yl]methyl}-L-valinate)-water (1/15) (IUPAC nomenclature).

LCZ696 acts as angiotensin receptor neprilysin inhibitor (ARNI) and is therefore useful particularly in the treatment of hypertention or chronic heart failure. Its utility has been confirmed by clinical trials, e.g. in the landmark PARADIGM-HF trial.

Chemical synthesis routes to prepare NEP inhibitors and their prodrugs, in particular sacubitril, and its precursors have been described previously, e.g. in Ksander et al. *J. Med. Chem.* 1995, 38, pp. 1689-1700; in U.S. Pat. No. 5,217,996, in the international patent applications WO 2008/031567, WO 2008/083967, WO 2009/090251, WO 2010/081410, WO 2011/035569, WO 2011/088797, WO 2012/025501, WO 2012/025502, WO 2014/032627 and WO 2016/135751, and in recently published CN patent applications such as CN104557600A, CN105152980A, CN105330569A, CN105601524A, CN105753741A, CN105884656A and CN105924355A and others.

However, there is still a need to design a chemical process for the synthesis of sacubitril which is suitable for industrial scale production under economically and environmentally favorable conditions and provides the drug substance in high chemical purity and with high stereo-chemical selectivity.

SUMMARY OF THE INVENTION

The invention relates to novel intermediates and process steps and processes for the manufacture of a compound of formula (XV), especially (XV-a) represented below, and its further use in the manufacture of sacubitril.

In a first aspect, the present invention provides the following new compounds:

A compound of formula (XV), or a salt thereof

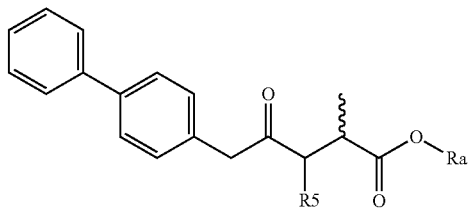

(XV)

wherein

R5 is selected from hydrogen and a group —CO—OR*, and

Ra and R* are, independently of each other, selected from hydrogen, a carboxyl protecting group, and $C_1$-$C_6$-alkyl, preferably ethyl.

In one embodiment thereof, the compound of the formula (XV) is represented by formula (XV-a) with the following stereochemistry

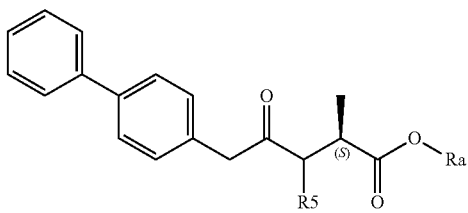

(XV-a)

wherein

R5 is selected from hydrogen and a group —CO—OR*, and

Ra and R* are, independently of each other, selected from hydrogen, a carboxyl protecting group, and $C_1$-$C_6$-alkyl, preferably ethyl.

In one embodiment thereof, the compound of formula (XV) is a compound of formula (I), or a salt thereof;

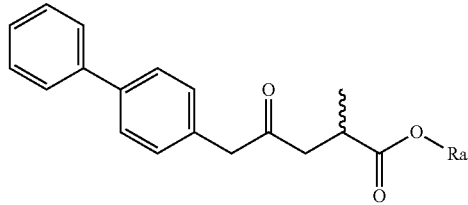

(I)

wherein Ra is selected from hydrogen, a carboxyl protecting group, and $C_1$-$C_6$-alkyl, preferably ethyl.

In one embodiment thereof, the compound of the formula (I) is represented by formula (I-a) with the following stereochemistry

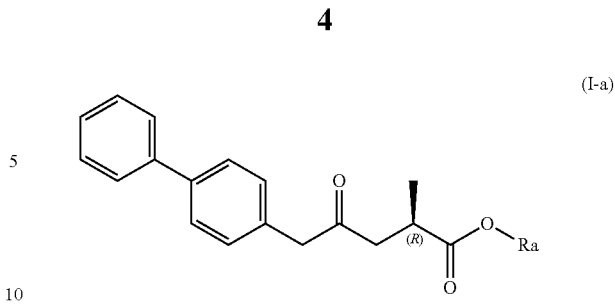

(I-a)

wherein Ra is selected from hydrogen, a carboxyl protecting group, and $C_1$-$C_6$-alkyl, preferably ethyl.

In one embodiment thereof, the compound of formula (XV) is a compound of formula (II), or a salt thereof;

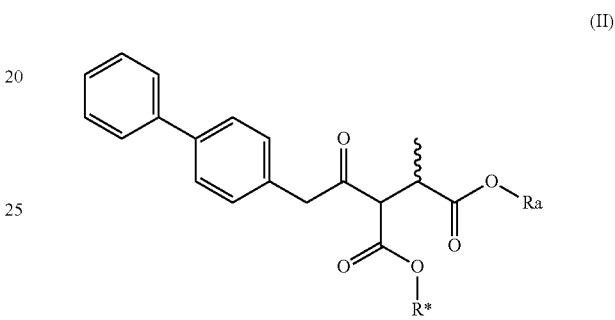

(II)

wherein Ra and R* are, independently of each other, selected from hydrogen, a carboxyl protecting group, and $C_1$-$C_6$-alkyl, preferably ethyl.

In one embodiment thereof, the compound of the formula (II) is represented by formula (II-a) with the following stereochemistry

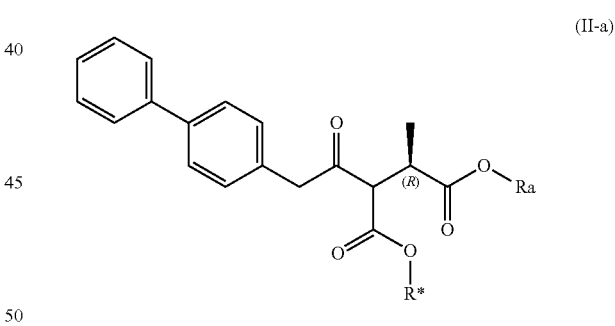

(II-a)

wherein Ra and R* are, independently of each other, selected from hydrogen, a carboxyl protecting group, and $C_1$-$C_6$-alkyl, preferably ethyl.

A compound of formula (XVI), or a salt thereof

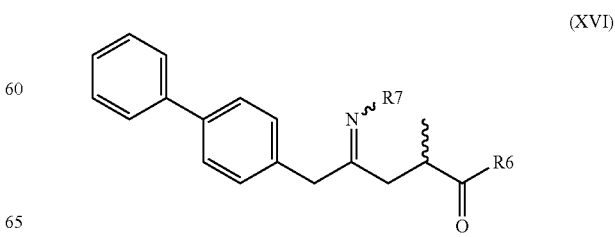

(XVI)

wherein

R6 is —O—Ra and R7 is selected from

—S(=O)—Rb

—OH

A, wherein A is —O—C(=O)—Rc or —O-Rd wherein Ra is selected from hydrogen, a carboxyl protecting group, and $C_1$-$C_6$-alkyl, preferably ethyl, and Rb, Rc and Rd are independently selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl, or R6 and R7 together represent —O— or form a bond.

In one embodiment thereof, the compound of the formula (XVI) is represented by formula (XVI-a) with the following stereochemistry

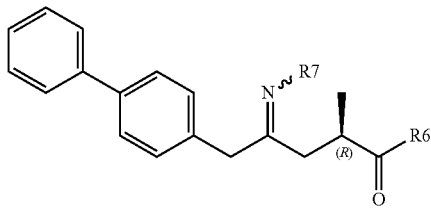

(XVI-a)

wherein

R6 is —O—Ra and R7 is selected from

—S(=O)—Rb

—OH, and

A, wherein A is —O—C(=O)—Rc or —O-Rd wherein Ra is selected from hydrogen, a carboxyl protecting group, and $C_1$-$C_6$-alkyl, preferably ethyl, and Rb, Rc and Rd are independently selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl, or R6 and R7 together represent —O— or form a bond.

In embodiment A thereof, the compound of formula (XVI) is a compound of formula (X), or a salt thereof

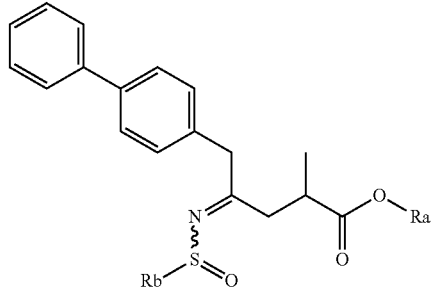

(X)

wherein Ra is selected from hydrogen, a carboxyl protecting group, and $C_1$-$C_6$-alkyl, preferably ethyl, and Rb is selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl.

In one embodiment thereof, the compound of the formula (X) is represented by formula (X-a) with the following stereochemistry

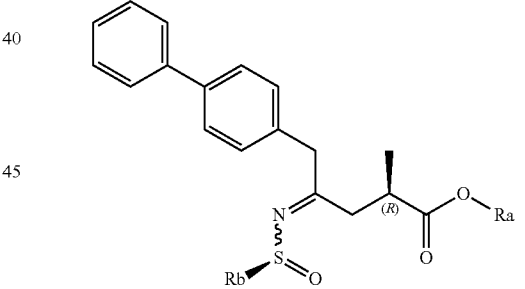

(X-a)

wherein Ra is selected from hydrogen, a carboxyl protecting group, and $C_1$-$C_6$-alkyl, preferably ethyl, and Rb is selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl.

In embodiment B thereof, the compound of formula (XVI) is a compound of formula (XVII), or a salt thereof

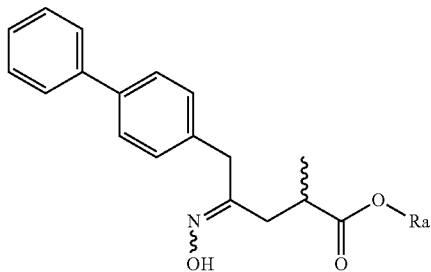

(XVII)

wherein Ra is selected from hydrogen, a carboxyl protecting group, and $C_1$-$C_6$-alkyl, preferably ethyl.

In one embodiment thereof, the compound of the formula (XVII) is represented by formula (XVII-a) with the following stereochemistry

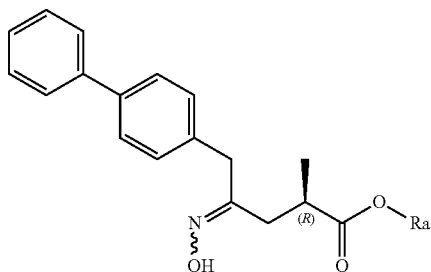

(XVII-a)

wherein Ra is selected from hydrogen, a carboxyl protecting group, and $C_1$-$C_6$-alkyl, preferably ethyl.

In embodiment C thereof, the compound of formula (XVI) is a compound of formula (XVII*), or a salt thereof

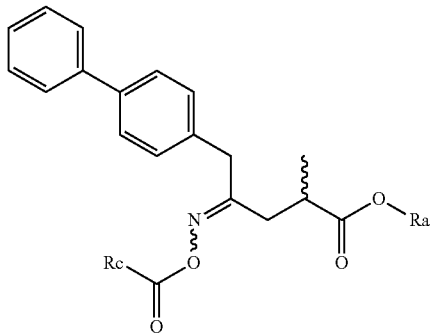

(XVII*)

wherein Ra is selected from hydrogen, a carboxyl protecting group, and $C_1$-$C_6$-alkyl, preferably ethyl, and Rc is selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl.

In one embodiment thereof, the compound of the formula (XVII*) is represented by formula (XVII*-a) with the following stereochemistry

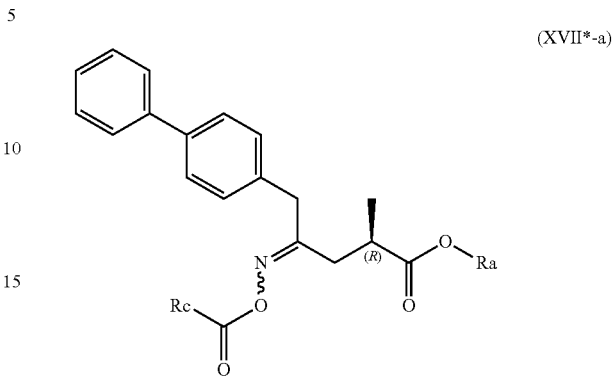

(XVII*-a)

wherein Ra is selected from hydrogen, a carboxyl protecting group, and $C_1$-$C_6$-alkyl, preferably ethyl, and Rc is selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl.

In embodiment D thereof, the compound of formula (XVI) is a compound of formula (XVII**), or a salt thereof

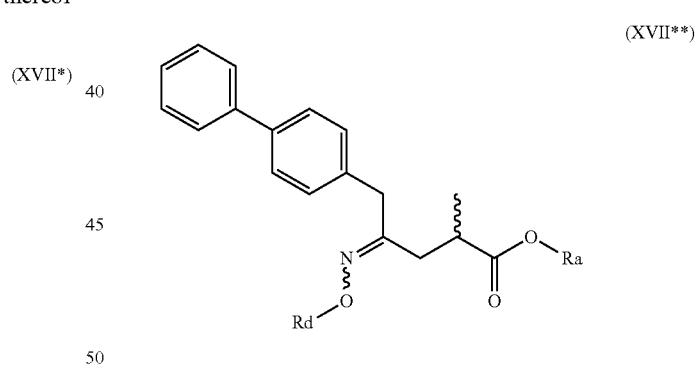

(XVII**)

wherein Ra is selected from hydrogen, a carboxyl protecting group, and $C_1$-$C_6$-alkyl, preferably ethyl, and Rd is selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl.

In one embodiment thereof, the compound of the formula (XVII) is represented by formula (XVII-a) with the following stereochemistry (XVII**-a)

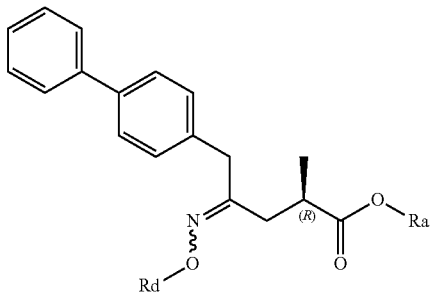

wherein Ra is selected from hydrogen, a carboxyl protecting group, and $C_1$-$C_6$-alkyl, preferably ethyl, and Rd is selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl.

In embodiment E thereof, the compound of formula (XVI) is a compound of formula (XVIII), or a salt thereof (XVIII)

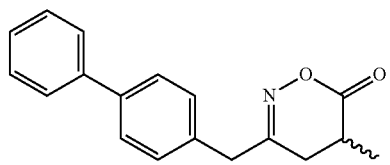

In one embodiment thereof, the compound of the formula (XVIII) is represented by formula (XVIII-a) with the following stereochemistry (XVIII-a)

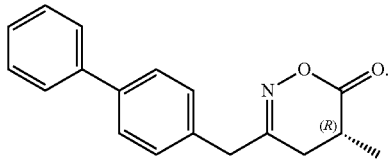

In embodiment F thereof, the compound of formula (XVI) is a compound of formula (XIX), or a salt thereof (XIX)

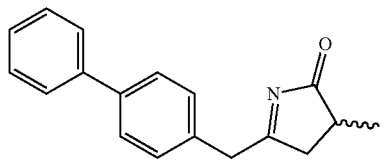

In one embodiment thereof, the compound of the formula (XIXI) is represented by formula (XIX-a) with the following stereochemistry (XIX-a)

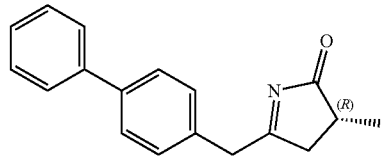

In a second aspect, the present invention provides a new process for the manufacture of the novel compound of formula (I), in particular of formula (I-a), or a salt thereof, as defined herein. This process comprises several steps via novel intermediate compounds and is depicted in the following Schemes 1 to 4, respectively, wherein each process depicted in the corresponding SCHEMEs 1, 2, 3, or 3* represents a separate embodiment of the invention.

SCHEME 1

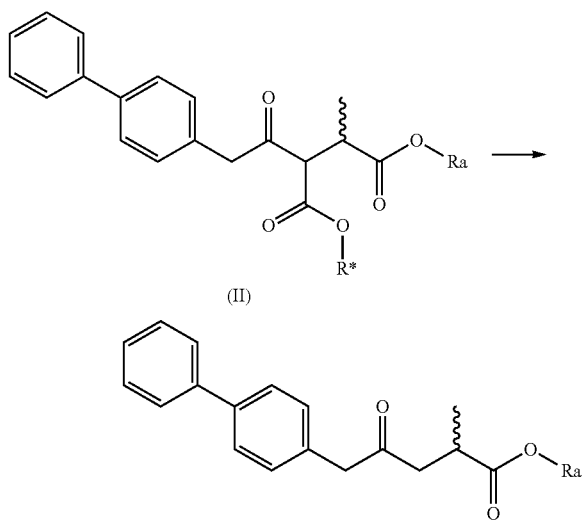

SCHEME 1-a

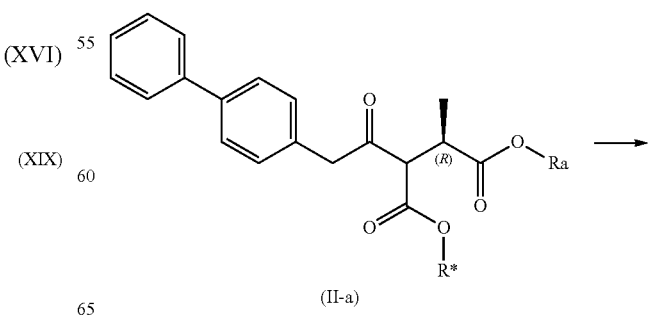

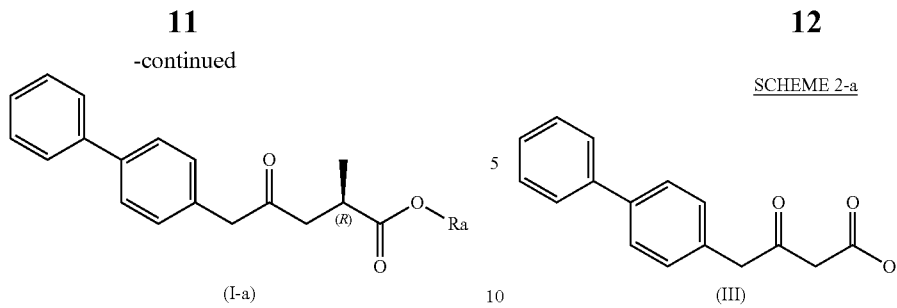

(I-a)

SCHEME 1 and SCHEME 1-a depict the process comprising reacting the novel intermediate compound of formula (II), preferably of formula (II-a), or a salt thereof, wherein Ra and R* are, independently of each other, selected from hydrogen, a carboxyl protecting group, and $C_1$-$C_6$-alkyl, preferably ethyl, under—if required—deprotection reaction conditions followed by decarboxylation reaction conditions, and optionally—if necessary or desired, e.g. if Ra is cleaved off during deprotection—by introduction of a moiety Ra selected from a carboxyl protecting group and $C_1$-$C_6$-alkyl, to provide the compound of formula (I) preferably of formula (I-a), or a salt thereof, wherein Ra is selected from hydrogen, a carboxyl protecting group and $C_1$-$C_6$-alkyl, preferably ethyl. If R* and Ra are different and Ra is already $C_1$-$C_6$-alkyl, especially ethyl, then only R* (e.g. tert-butyl) can be cleaved off selectively, while under the same conditions the $C_1$-$C_6$-alkyl, e.g. ethyl, remains bound. If desired—and not explicitly disclosed in the SCHEME 1—this can be followed by converting a compound of the formula (I), especially (I-a) into a salt, e.g. with an acid.

In one embodiment, the compound of formula (II) can be obtained according to a reaction as depicted in the following SCHEMES 2 and 2-a:

SCHEME 2

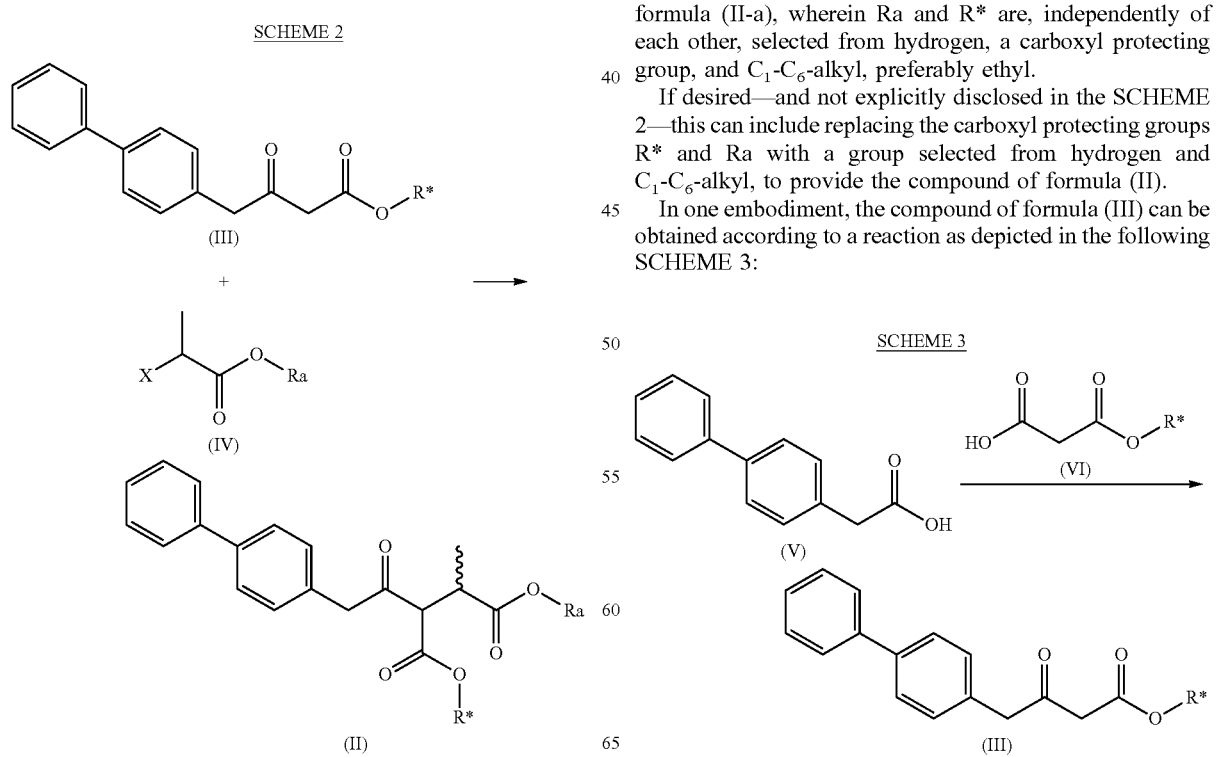

SCHEME 2-a

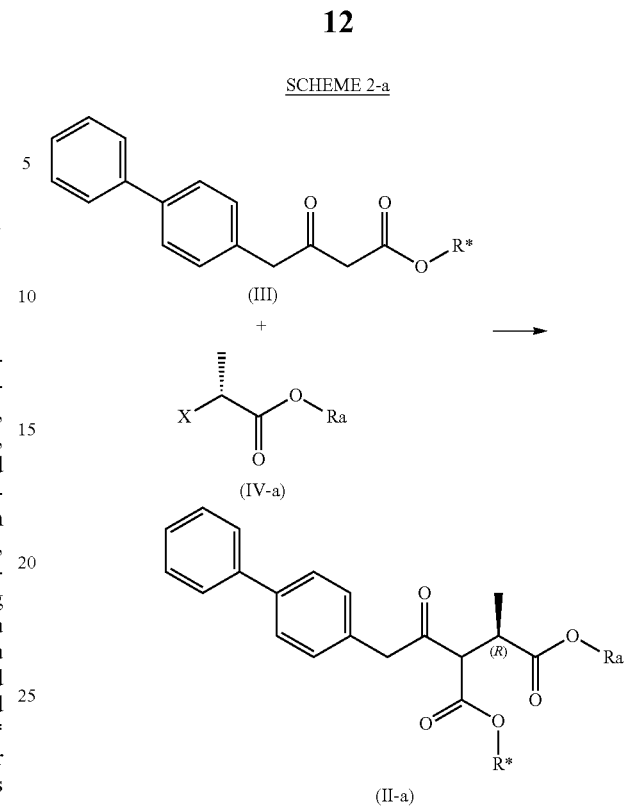

SCHEME 2 and SCHEME 2-a, both depict a process comprising reacting a compound of formula (III), with a propionate derivative of formula (IV), preferably of formula (IV-a), wherein X is a leaving group and Ra is selected from a carboxyl protecting group and $C_1$-$C_6$-alkyl, preferably ethyl, to obtain a compound of formula (II), preferably of formula (II-a), wherein Ra and R* are, independently of each other, selected from hydrogen, a carboxyl protecting group, and $C_1$-$C_6$-alkyl, preferably ethyl.

If desired—and not explicitly disclosed in the SCHEME 2—this can include replacing the carboxyl protecting groups R* and Ra with a group selected from hydrogen and $C_1$-$C_6$-alkyl, to provide the compound of formula (II).

In one embodiment, the compound of formula (III) can be obtained according to a reaction as depicted in the following SCHEME 3:

SCHEME 3 depicts a process comprising reacting a compound of formula (V), or a reactive derivative thereof, with a salt of a malonic acid half ester of formula (VI), wherein R* is selected from a carboxyl protecting group and $C_1$-$C_6$-alkyl, preferably ethyl, to obtain a compound of formula (III).

As an alternative to the process as depicted in above SCHEMEs 1 to 3, the novel compound of formula (I), in particular of formula (I-a), or a salt thereof, can also be obtained by a process as depicted in the following Scheme 3* or 3*-a, which also represents a separate embodiment of the invention.

SCHEME 3*

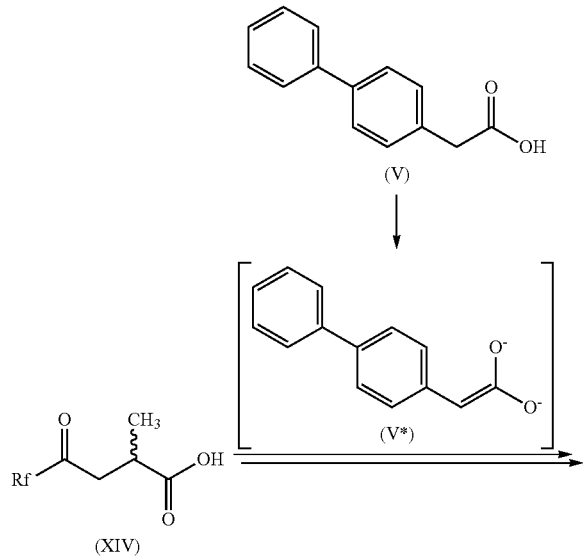

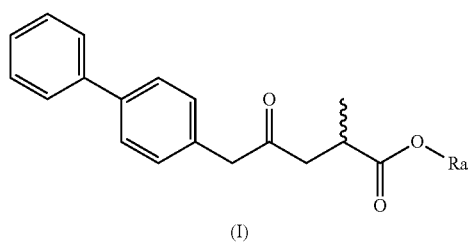

SCHEME 3*-a

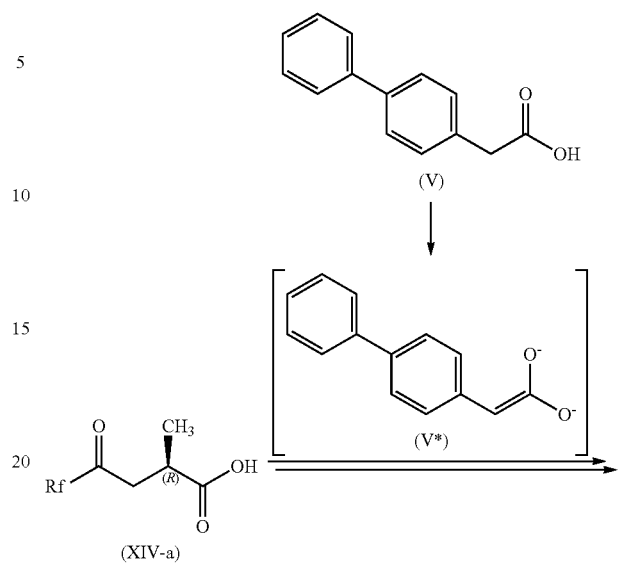

SCHEME 3* and SCHEME 3*-a depict a process comprising reacting the intermediate compound of formula (XIV), preferably of formula (XIV-a), or a salt thereof, wherein Rf is selected from a group —O—R* wherein R* is selected from a carboxyl protecting group and $C_1$-$C_6$-alkyl, preferably methyl; —N(CH3)-O(CH3), morpholinyl, and imidazolinyl, with an in situ prepared activated dianionic derivative of the compound of formula (V), or a salt thereof, namely a compound of formula (V*), in the presence of a base, and followed by a decarboxylation reaction, to obtain the compound of formula (I), or a salt thereof wherein Ra is hydrogen. Such compound of formula XIV is known in the art. If necessary or desired, the obtained compound of formula (I), or a salt thereof, wherein Ra is hydrogen, can be reacted with an agent introducing a carboxyl protecting group, to provide the compound of formula (I), wherein Ra is a carboxyl protecting group, or the obtained compound of formula (I), or a salt thereof, wherein Ra is hydrogen, is reacted with a coupling reagent in the presence of an $C_1$-$C_6$-alkanol, especially ethanol, to provide the compound of formula (I), wherein Ra is $C_1$-$C_6$-alkyl, preferably ethyl.

In one embodiment, the compound of formula (V) as used as starting compound in SCHEMEs 3 and 3* can be obtained according to a reaction as depicted in the following SCHEME 4:

SCHEME 4

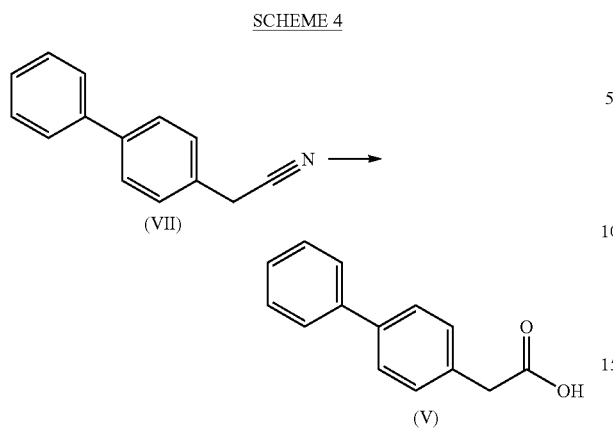

SCHEME 4 depicts a process comprising hydrolysing a cyanide compound of formula (VII) to obtain a compound of formula (V).

In a preferred embodiment, the reactions as depicted in SCHEMEs 1 to 4 above are carried out sequentially as one step after the other:
SCHEME 4->SCHEME 3->SCHEME 2->SCHEME 1, or
SCHEME 4->SCHEME 3*.

In another embodiment, the reaction sequence starts from SCHEME 3:
SCHEME 3->SCHEME 2->SCHEME 1.

In another embodiment, the reaction sequence starts from SCHEME 2:
SCHEME 2->SCHEME 1.

In a third aspect, the present invention provides a new process for the manufacture of a compound of the formula (VIII), in particular of formula (VIII-a), more preferably of formula (VIII-aa), or a salt thereof, as depicted below and as defined herein, by various reactions all starting from the novel compound of formula (I), in particular of formula (I-a), or a salt thereof, as defined herein. The overall reaction is depicted in the following SCHEMEs 5, 5-a and 5-aa:

SCHEME 5

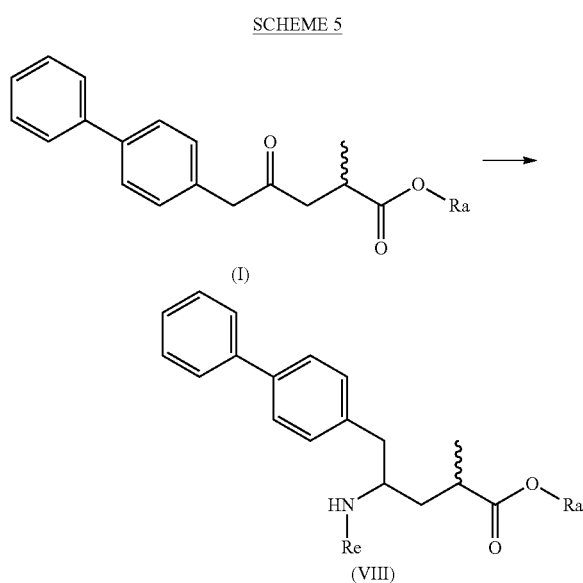

SCHEME 5-a

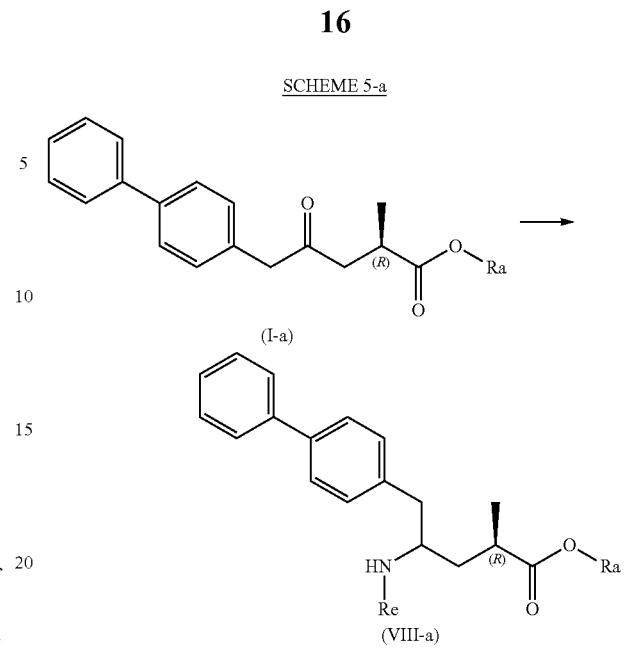

SCHEME 5-aa

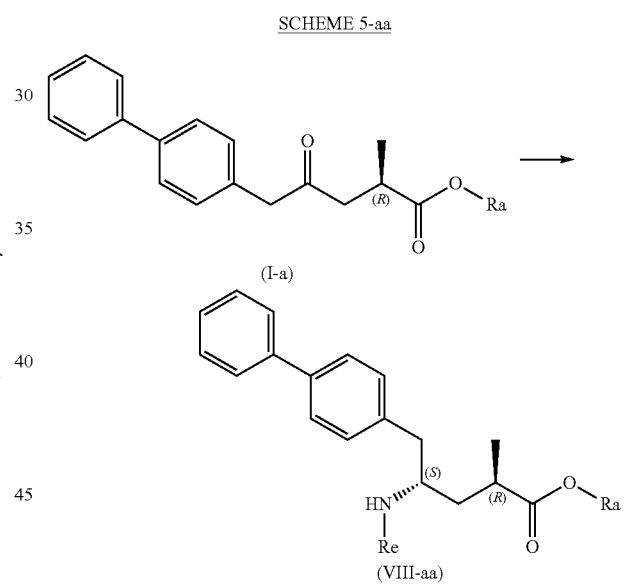

This reaction can be achieved by a variety of reactions depicted in the following Schemes 6 to 10, respectively, wherein the process depicted in each SCHEME 5, 6, 7, 8, 9 and 10 represents a separate, alternative embodiment of the invention.

In one embodiment, the novel compound of formula (I) can be converted into a compound of formula (VIII) according to a reaction ("Reaction with ammonia, a primary or a secondary amine, or salts thereof") as depicted in SCHEMES 5, 5-A and 5-aa above (therefore not shown separately).

In this embodiment, SCHEMEs 5, 5-A and 5-aa depict the process comprising reacting the novel intermediate compound of formula (I), preferably of formula (I-a), or a salt thereof, wherein Ra is hydrogen, with ammonia, a primary or secondary amine, or salts thereof, and optionally cleaving off any undesired substituents of the amine, to provide a compound of formula (VIII), in particular of formula (VIII-a), more preferably of formula (VIII-aa), or a salt thereof, wherein Ra and Re are hydrogen, or if the primary amine has the formula NH₂—Re, with Re being a nitrogen protecting group, to provide a compound of formula (VIII), in particular of formula (VIII-a), more preferably of formula (VIII-aa), or a salt thereof, wherein Ra is hydrogen and Re is a nitrogen protecting group, and optionally reacting the obtained compound of formula (VIII), in particular of formula (VIII-a), more preferably of formula (VIII-aa), or a salt thereof, wherein Ra and Re are hydrogen, with an agent introducing an amino protecting group, to provide the compound of formula (VIII), in particular of formula (VIII-a), more preferably of formula (VIII-aa), wherein Ra is hydrogen, and Re is a nitrogen protecting group, and/or optionally followed by reacting the optionally amino protected analog of the compound of the formula (VIII), in particular of formula (VIII-a), more preferably of formula (VIII-aa), with a coupling reagent in the presence of an $C_1$-$C_6$-alkanol, especially ethanol, to provide the compound of formula (VIII), in particular of formula (VIII-a), more preferably of formula (VIII-aa), or a salt thereof, wherein Ra is $C_1$-$C_6$-alkyl, preferably ethyl, and Re is hydrogen or a nitrogen protecting group.

In one embodiment of SCHEME 5, 5-a or 5-aa, the compound of formula (I) is obtained by a process as depicted in SCHEME 1, optionally including the reaction steps as depicted in SCHEMEs 2 to 4, or by a process as depicted in SCHEME 3*, optionally including the reaction steps as depicted in SCHEME 4.

In one embodiment, the novel compound of formula (I) can be converted into a compound of formula (VIII) according to a reaction as depicted in the following SCHEMES 6, 6-1, 6-A and 6-aa ("Reaction using a transaminase"):

SCHEME 6

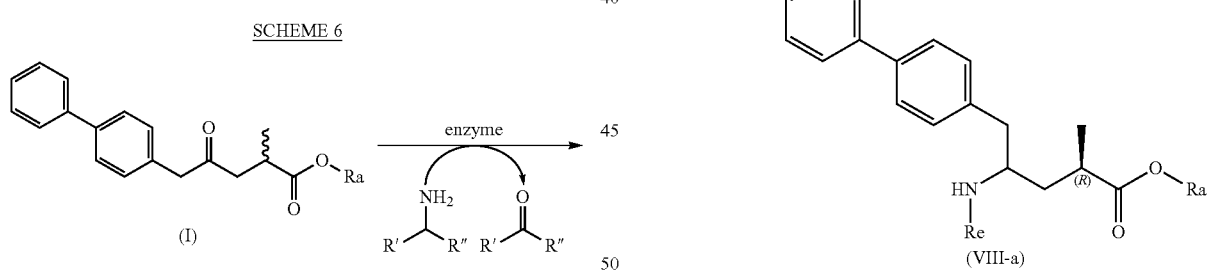

SCHEME 6-1

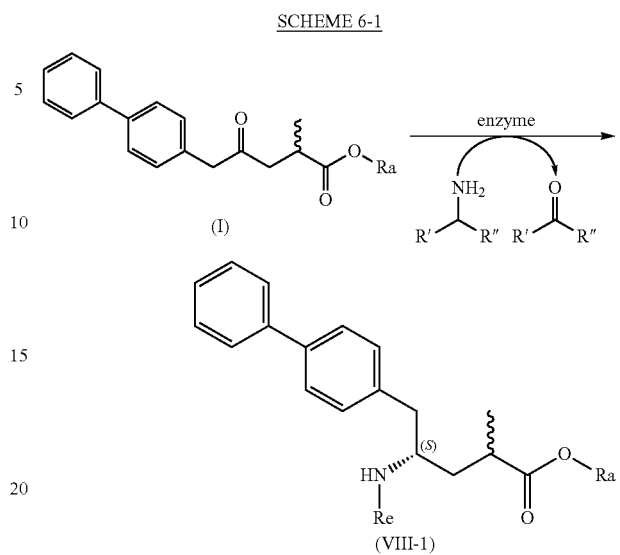

SCHEME 6-a

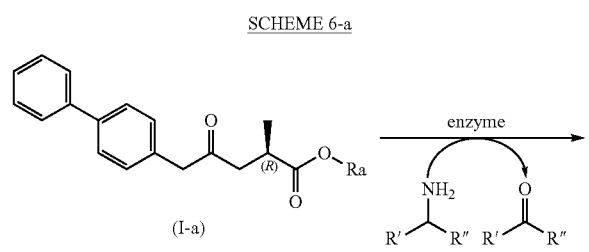

SCHEME 6-aa

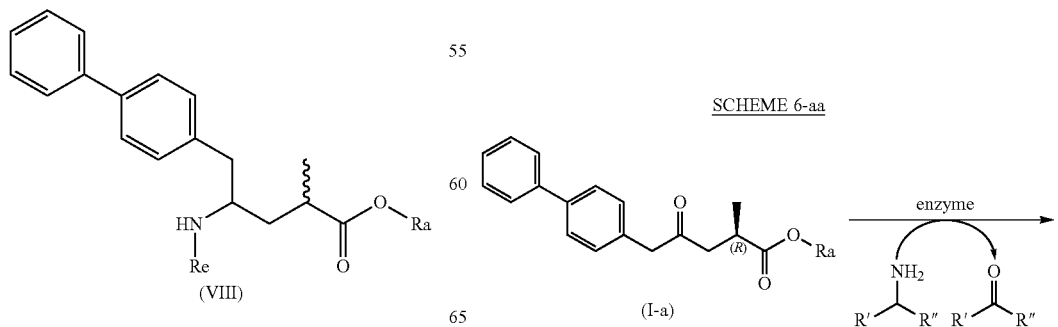

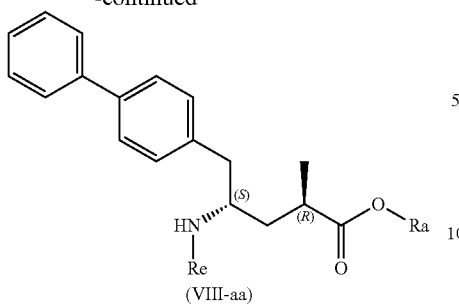

(VIII-aa)

SCHEMEs 6, 6-1, 6-A and 6-aa ("Reaction using a transaminase") depict the process comprising converting the novel intermediate compound of formula (I) or formula (I-a), or a salt thereof, wherein Ra is selected from hydrogen and $C_1$-$C_6$-alkyl, preferably hydrogen, into the compound of formula (VIII), preferably of formula (VIII-1), or of formula (VIII-a), more preferably of formula (VIII-aa), wherein Ra is selected from hydrogen and $C_1$-$C_6$-alkyl, preferably hydrogen, and Re is hydrogen, or a salt thereof, by bringing it in contact with an (S)-selective ω-transaminase in the presence of an amine donor of the general formula R'R''CH—$NH_2$ and a coenzyme, wherein the conversion rate from the compound of formula (I) to the compound of formula (VIII), preferably of formula (VIII-1), in particular the conversion rate from the compound of formula (I-a) to the compound of formula (VIII-a), preferably of formula (VIII-aa), is more than 50%.

This is optionally followed by reacting the obtained compound of formula (VIII), in particular of formula (VIII-a), or of formula (VIII-a), preferably of formula (VIII-aa), or a salt thereof, wherein Ra and Re are hydrogen, with an agent introducing an amino protecting group, to provide the compound of formula (VIII), in particular of formula (VIII-1), or of formula (VIII-a), preferably of formula (VIII-aa), wherein Ra is hydrogen, and Re is a nitrogen protecting group.

Subsequently or alternative, the optionally amino protected analog of the compound of the formula (VIII), in particular of formula (VIII-1), or of formula (VIII-a), preferably of formula (VIII-aa), wherein Ra is hydrogen, is optionally reacted with a coupling reagent in the presence of an $C_1$-$C_6$-alkanol, especially ethanol, to provide the compound of formula (VIII), in particular of formula (VIII-1), or of formula (VIII-a), preferably of formula (VIII-aa), or a salt thereof, wherein Ra is $C_1$-$C_6$-alkyl, preferably ethyl, and Re is hydrogen or a nitrogen protecting group.

In one embodiment of SCHEME 6, 6-1, 6-a or 6-aa, the compound of formula (I) is obtained by a process as depicted in SCHEME 1, optionally including the reaction steps as depicted in SCHEMEs 2, 2 to 3, or 2 to 4, or by a process as depicted in SCHEME 3*, optionally including the reaction steps as depicted in SCHEME 4.

In one embodiment, the novel compound of formula (I) can be converted into a compound of formula (VIII) according to a reaction as depicted in the following SCHEMES 7, 7-a and 7-aa ("reaction via the novel sulfinimide compound of the formula (X)"):

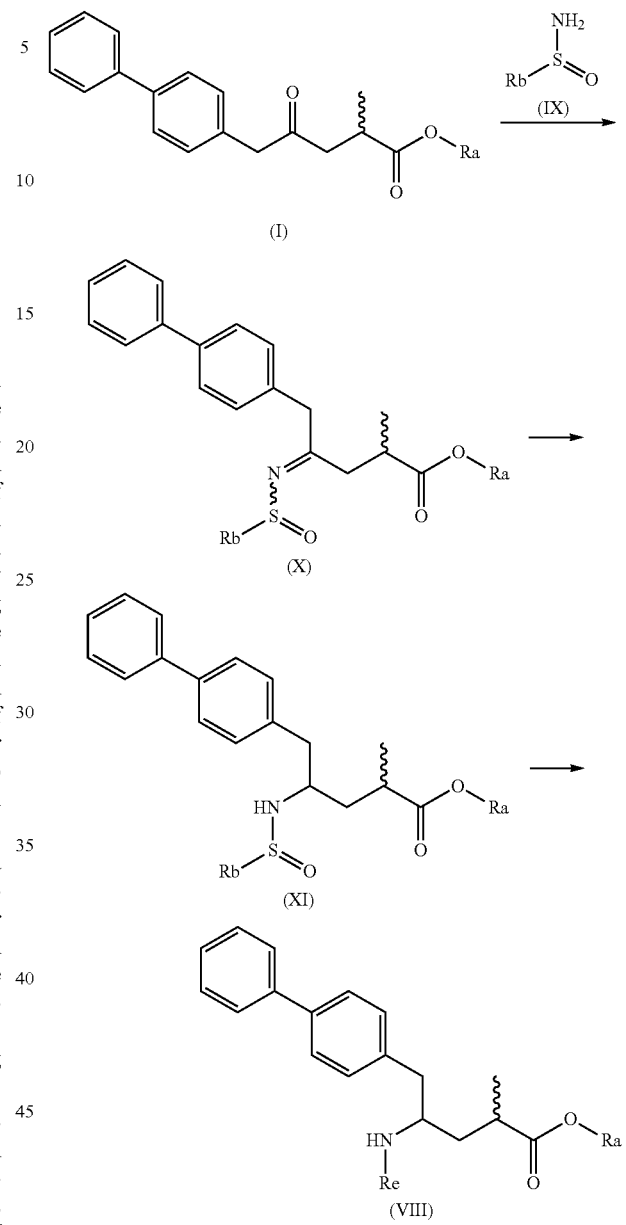

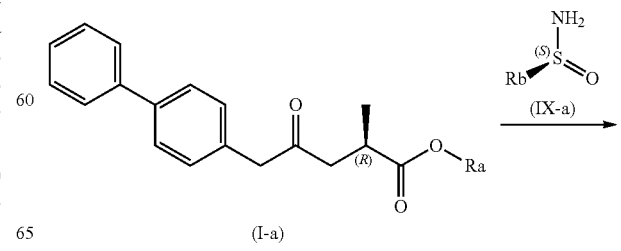

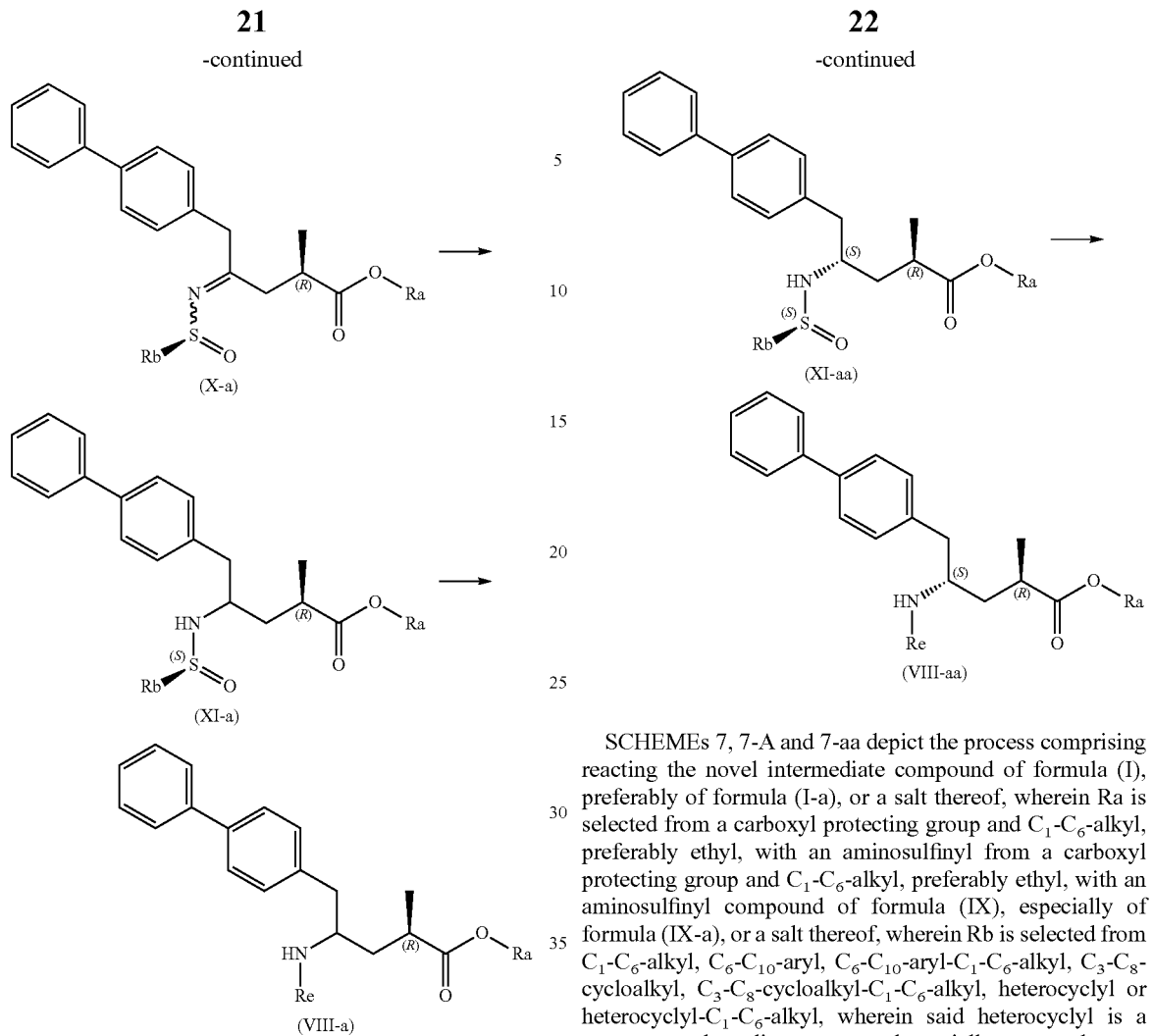

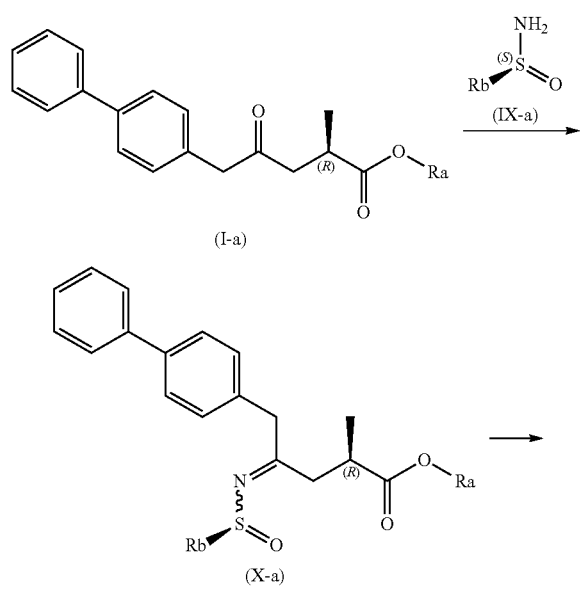

SCHEMEs 7, 7-A and 7-aa depict the process comprising reacting the novel intermediate compound of formula (I), preferably of formula (I-a), or a salt thereof, wherein Ra is selected from a carboxyl protecting group and $C_1$-$C_6$-alkyl, preferably ethyl, with an aminosulfinyl from a carboxyl protecting group and $C_1$-$C_6$-alkyl, preferably ethyl, with an aminosulfinyl compound of formula (IX), especially of formula (IX-a), or a salt thereof, wherein Rb is selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl, to give a sulfinimide compound of the formula (X), preferably of formula (X-a), or a salt thereof, wherein Rb is selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl, and Ra is selected from a carboxyl protecting group and $C_1$-$C_6$-alkyl, preferably ethyl, then reducing the obtained compound of formula (X), preferably of formula (X-a), or a salt thereof, in the presence of a reducing agent to give a sulfinamide compound of the formula (XI), preferably of formula (XI-a), more preferably of formula (XI-aa), or a salt thereof, wherein Rb is selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl, and Ra is selected from a carboxyl protecting group and $C_1$-$C_6$-alkyl, preferably ethyl, then reacting the obtained sulfinamide compound of formula (XI), preferably of formula (XI-a), more preferably of formula (XI-aa), or a salt thereof, by hydrolyzing the sulfonamide group in the presence of an acid to provide a compound of formula (VIII), in particular of formula (VIII-a), more preferably of formula (VIII-aa), or a salt thereof, wherein Ra is selected from a carboxyl protecting group and $C_1$-$C_6$-alkyl, preferably ethyl, and Re is hydrogen, and optionally removing any carboxyl protecting group from the obtained compound of formula (VIII), preferably of formula (VIII-a), more preferably of formula (VIII-aa), or a salt thereof, to provide a compound of formula (VIII), preferably of formula (VIII-a), more preferably of formula (VIII-aa), or a salt thereof, wherein Ra is hydrogen and Re is hydrogen, and/or optionally reacting the obtained compound of formula (VIII), preferably of formula (VIII-a), more preferably of formula (VIII-aa), or a salt thereof, wherein Re is hydrogen, with an agent introducing an amino protecting group, to provide the compound of formula (VIII), preferably of formula (VIII-a), more preferably of formula (VIII-aa), or a salt thereof, wherein Ra is hydrogen, and Re is a nitrogen protecting group, optionally followed by reacting the optionally amino protected analogue of the compound of the formula (VIII) preferably of formula (VIII-a), more preferably of formula (VIII-aa), or a salt thereof, with a coupling reagent in the presence of an $C_1$-$C_6$-alkanol, especially ethanol, to provide the compound of formula (VIII), preferably of formula (VIII-a), more preferably of formula (VIII-aa), or a salt thereof, wherein Ra is $C_1$-$C_6$-alkyl, preferably ethyl, and Re is hydrogen or a nitrogen protecting group.

In one embodiment of SCHEME 7, 7-a or 7-aa, the compound of formula (I) is obtained by a process as depicted in SCHEME 1, optionally including the reaction steps as depicted in SCHEMEs 2 to 4, or by a process as depicted in SCHEME 3*, optionally including the reaction steps as depicted in SCHEME 4.

In another embodiment, the novel compound of formula (I) can be converted into a compound of formula (VIII) according to a reaction as depicted in the following SCHEMES 8, 8-a and 8-aa ("reaction with hydroxylamine via the novel compounds of formula (XVII) and of formula (XVIII)"):

SCHEME 8

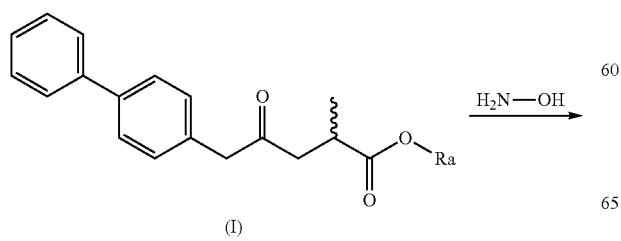

-continued

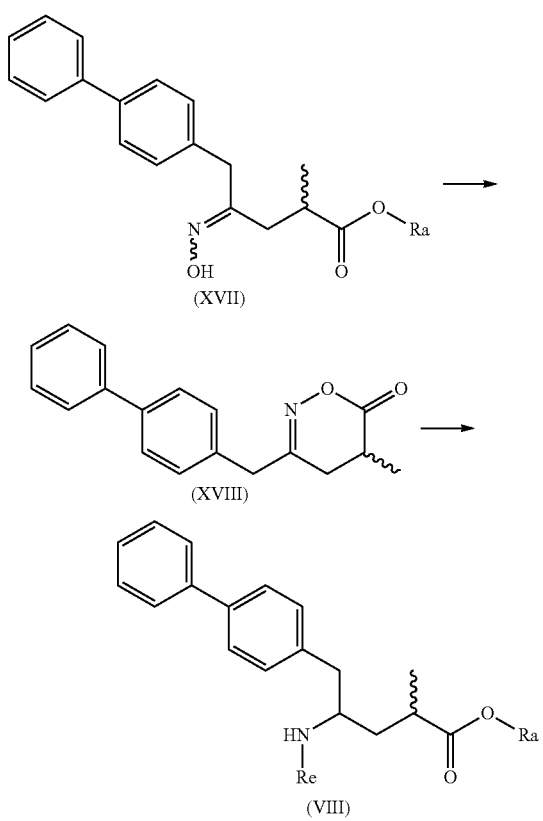

SCHEME 8-A

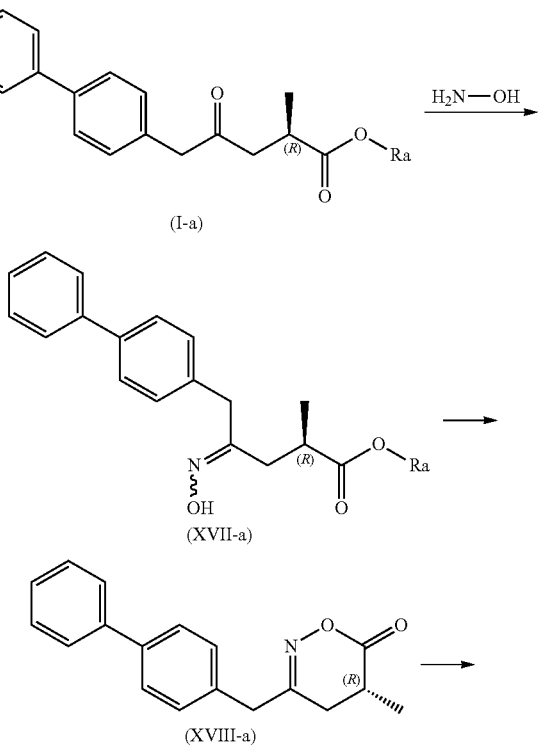

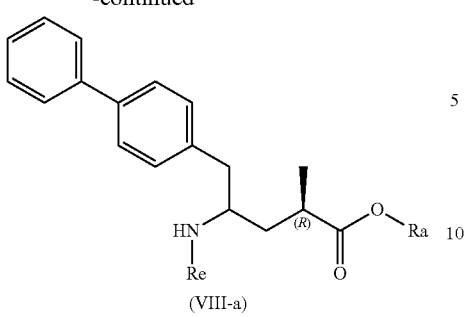

(VIII-a)

SCHEME 8-AA

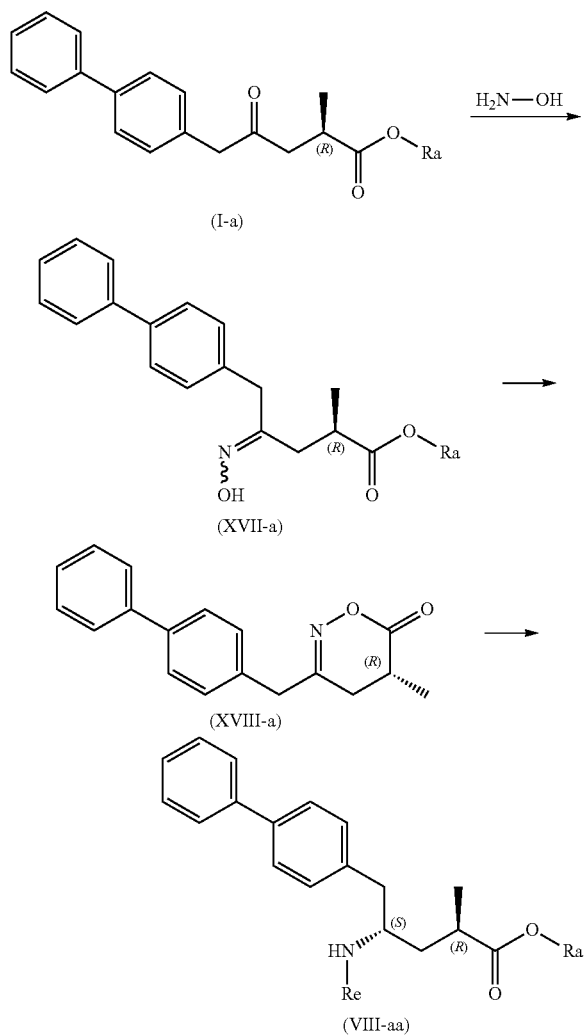

SCHEMEs 8, 8-A and 8-AA depict the process comprising reacting the novel intermediate compound of formula (I), preferably of formula (I-a), or a salt thereof, wherein Ra is hydrogen, with hydroxylamine or a salt thereof, to provide a compound of formula (XVII), preferably of formula (XVII-a), or a salt thereof, wherein Ra is hydrogen, subsequently cyclizing the obtained compound of formula (XVII), preferably of formula (XVII-a), or a salt thereof, to give the corresponding compound of the formula (XVIII), preferably of formula (XVIII-a), or a salt thereof, then reducing the obtained compound of formula (XVIII), preferably of formula (XVIII-a), or a salt thereof, in the presence of a reducing agent, to obtain the compound of formula (VIII), preferably of formula (VIII-a), more preferably of formula (VIII-aa), or a salt thereof, wherein Ra and Re are both hydrogen, and optionally reacting the obtained compound of formula (VIII), preferably of formula (VIII-a), more preferably of formula (VIII-aa), or a salt thereof, wherein Ra and Re are hydrogen, with an agent introducing an amino protecting group, to provide the compound of formula (VIII), preferably of formula (VIII-a), more preferably of formula (VIII-aa), or a salt thereof, wherein Ra is hydrogen, and Re is a nitrogen protecting group, optionally followed by reacting the amino protected analog of the compound of the formula (VIII), preferably of formula (VIII-a), more preferably of formula (VIII-aa), or a salt thereof, with a coupling reagent in the presence of an $C_1$-$C_6$-alkanol, especially ethanol, to provide the compound of formula (VIII), preferably of formula (VIII-a), more preferably of formula (VIII-aa), or a salt thereof, wherein Ra is $C_1$-$C_6$-alkyl, preferably ethyl, and Re is hydrogen or a nitrogen protecting group.

In one embodiment of SCHEME 8, 8-A or 8-AA, the compound of formula (I) is obtained by a process as depicted in SCHEME 1, optionally including the reaction steps as depicted in SCHEMEs 2 to 4, or by a process as depicted in SCHEME 3*, optionally including the reaction steps as depicted in SCHEME 4.

In another embodiment, the novel compound of formula (I) can be converted into a compound of formula (VIII) according to a reaction as depicted in the following SCHEMES 9, 9-a and 9-aa ("reaction with ammonia or an ammonium via the novel compounds of formula (XIX) and (XX):

SCHEME 9

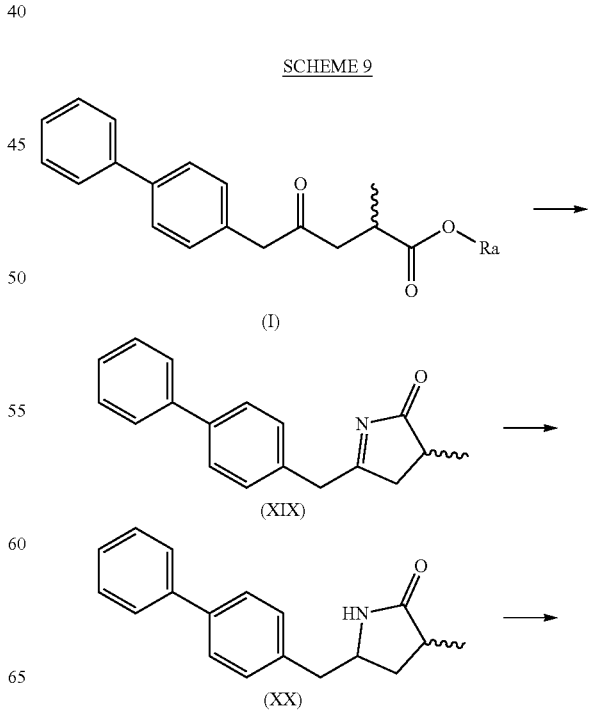

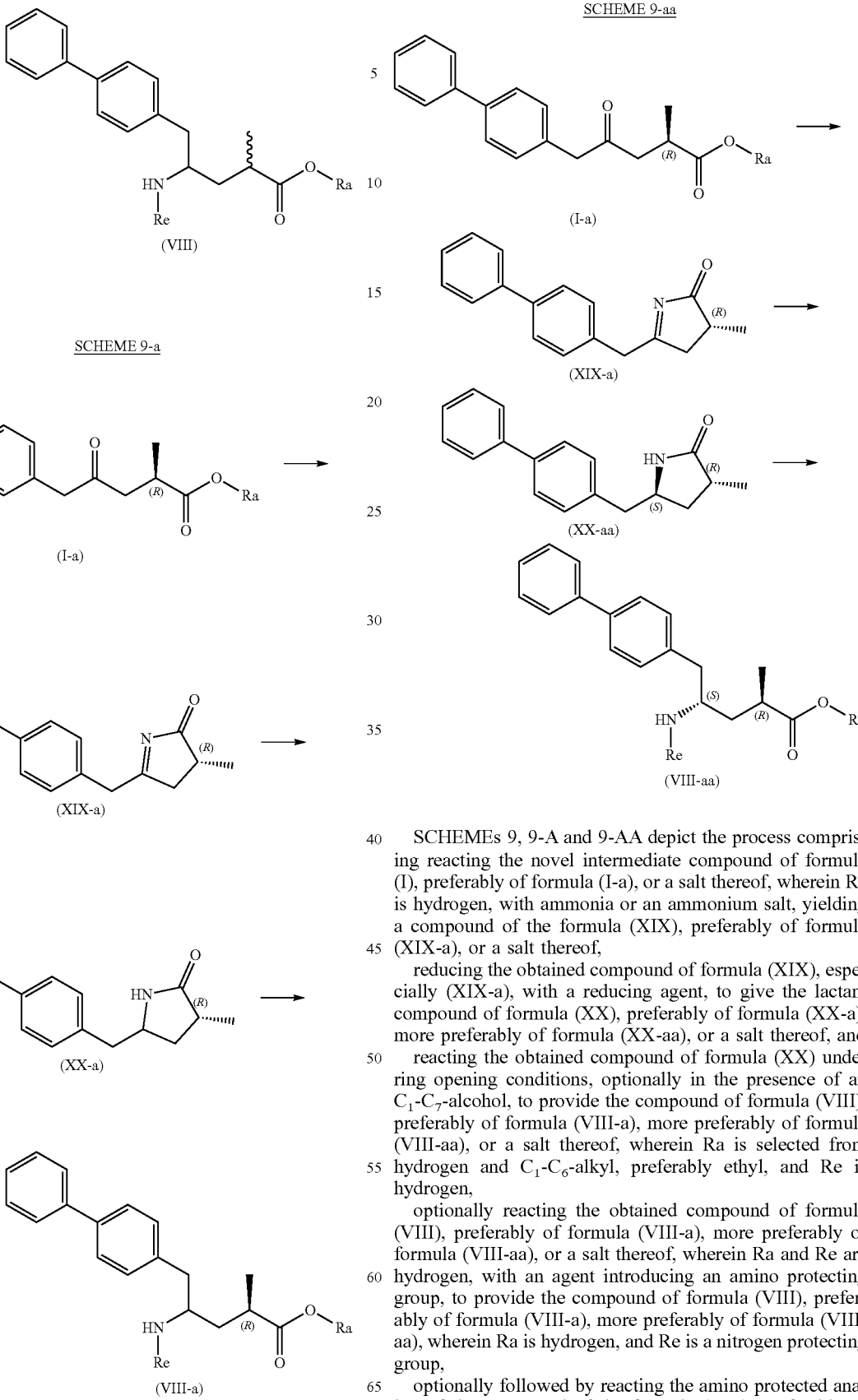

SCHEMEs 9, 9-A and 9-AA depict the process comprising reacting the novel intermediate compound of formula (I), preferably of formula (I-a), or a salt thereof, wherein Ra is hydrogen, with ammonia or an ammonium salt, yielding a compound of the formula (XIX), preferably of formula (XIX-a), or a salt thereof, reducing the obtained compound of formula (XIX), especially (XIX-a), with a reducing agent, to give the lactam compound of formula (XX), preferably of formula (XX-a), more preferably of formula (XX-aa), or a salt thereof, and reacting the obtained compound of formula (XX) under ring opening conditions, optionally in the presence of an $C_1$-$C_7$-alcohol, to provide the compound of formula (VIII), preferably of formula (VIII-a), more preferably of formula (VIII-aa), or a salt thereof, wherein Ra is selected from hydrogen and $C_1$-$C_6$-alkyl, preferably ethyl, and Re is hydrogen, optionally reacting the obtained compound of formula (VIII), preferably of formula (VIII-a), more preferably of formula (VIII-aa), or a salt thereof, wherein Ra and Re are hydrogen, with an agent introducing an amino protecting group, to provide the compound of formula (VIII), preferably of formula (VIII-a), more preferably of formula (VIII-aa), wherein Ra is hydrogen, and Re is a nitrogen protecting group, optionally followed by reacting the amino protected analog of the compound of the formula (VIII), preferably of formula (VIII-a), more preferably of formula (VIII-aa), or a salt thereof, with a coupling reagent in the presence of an $C_1$-$C_6$-alkanol, especially ethanol, to provide the compound of formula (VIII), preferably of formula (VIII-a), more preferably of formula (VIII-aa), or a salt thereof, wherein Ra is $C_1$-$C_6$-alkyl, preferably ethyl, and Re is hydrogen or a nitrogen protecting group.

In one embodiment of SCHEME 9, 9-A or 9-AA, the compound of formula (I) is obtained by a process as depicted in SCHEME 1, optionally including the reaction steps as depicted in SCHEMEs 2 to 4, or by a process as depicted in SCHEME 3*, optionally including the reaction steps as depicted in SCHEME 4.

In one embodiment, the novel compound of formula (I) can be converted into a compound of formula (VIII) according to a reaction as depicted in the following SCHEMES 10, 10-a and 10-aa ("reaction with an O-substituted hydroxylamine via the novel compounds of formula (XVII***), especially of formula (XVII*) and of formula (XVII**)"):

SCHEME 10

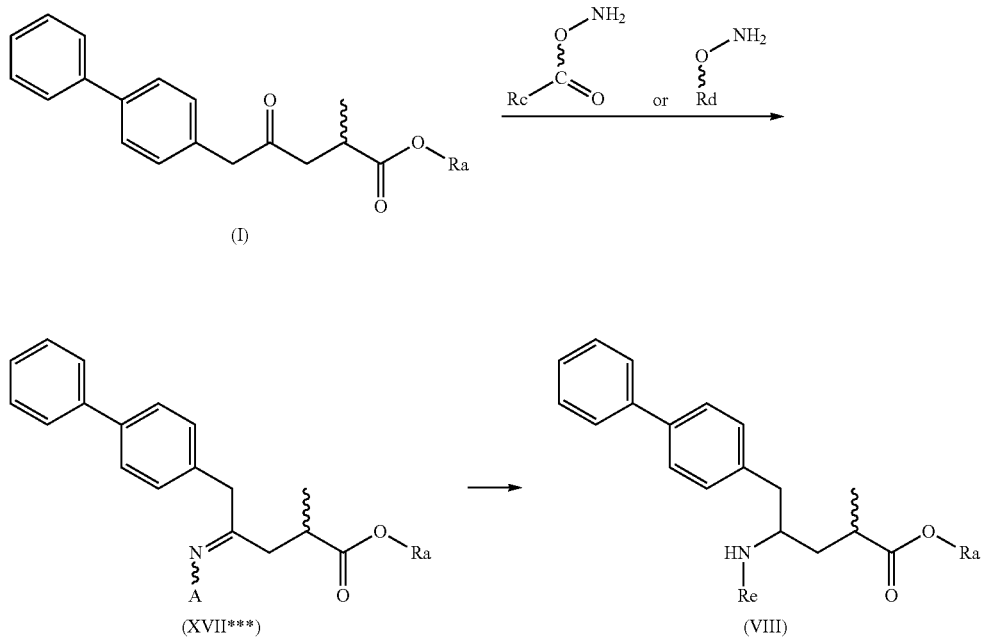

SCHEME 10-a

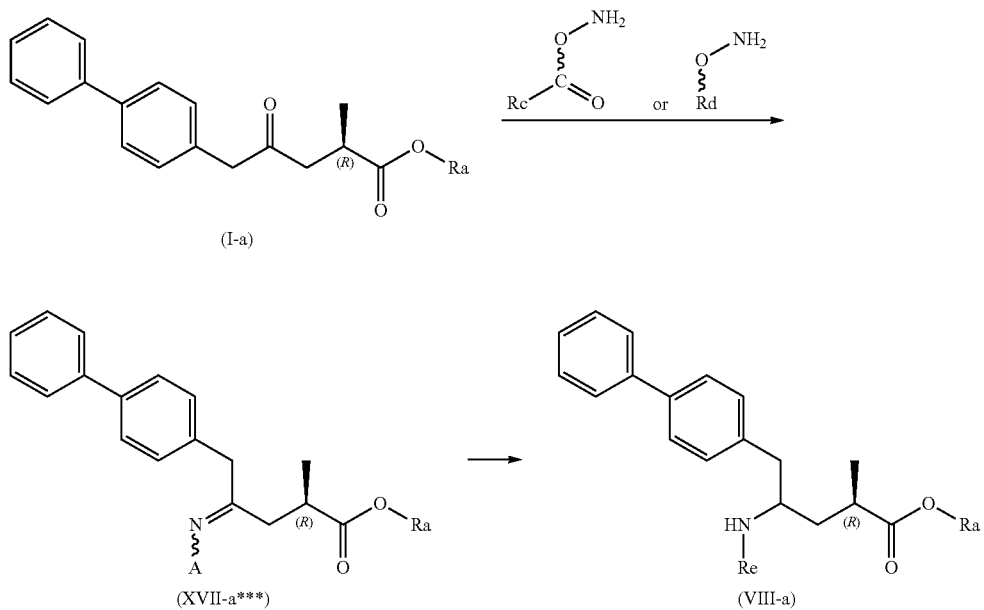

SCHEME 10-aa

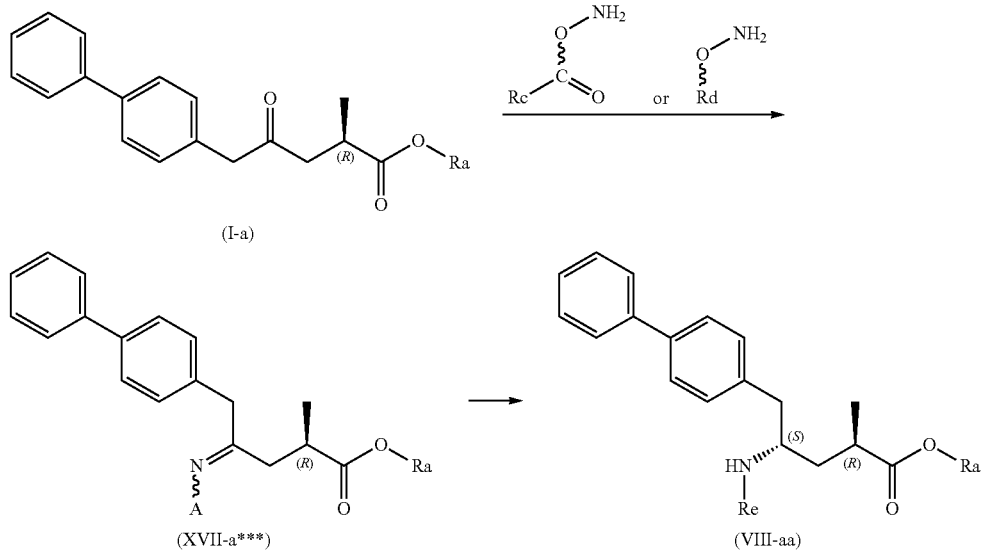

SCHEMEs 10, 10-A and 10-AA depict the process comprising reacting the novel intermediate compound of formula (I), preferably of formula (I-a), or a salt thereof, wherein Ra is selected from hydrogen, a carboxyl protecting group and $C_1$-$C_6$-alkyl, preferably ethyl, with a O-substituted hydroxylamine selected from

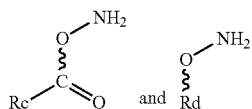

or in each case a salt thereof, wherein Rc and Rd are independently selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl, to provide a compound of formula (XVII*), preferably of formula (XVII*-a), or a salt thereof, wherein Ra is selected from hydrogen, a carboxyl protecting group, and $C_1$-$C_6$-alkyl, preferably ethyl, and A is —O—C(=O)—Rc or —O-Rd, wherein Rc and Rd are independently selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl, reducing the obtained compound of formula (XVII*), preferably of formula (XVII*-a), or a salt thereof to provide the compound of formula (VIII), preferably of formula (VIII-a), more preferably of formula (VIII-aa), or a salt thereof, wherein Ra is selected from hydrogen, a carboxyl protecting group and $C_1$-$C_6$-alkyl, preferably ethyl, and Re is hydrogen, and optionally removing any carboxyl protecting group from the obtained compound of formula (VIII), preferably of formula (VIII-a), more preferably of formula (VIII-aa), or a salt thereof, and/or optionally reacting the obtained compound of formula (VIII), preferably of formula (VIII-a), more preferably of formula (VIII-aa), or a salt thereof, wherein Re is hydrogen, with an agent introducing an amino protecting group, to provide the compound of formula (VIII), preferably of formula (VIII-a), more preferably of formula (VIII-aa), or a salt thereof, wherein Ra is hydrogen, and Re is a nitrogen protecting group, optionally followed by reacting the amino protected analog of the compound of the formula (VIII), preferably of formula (VIII-a), more preferably of formula (VIII-aa), or a salt thereof, with a coupling reagent in the presence of an $C_1$-$C_6$-alkanol, especially ethanol, to provide the compound of formula (VIII), preferably of formula (VIII-a), more preferably of formula (VIII-aa), or a salt thereof, wherein Ra is $C_1$-$C_6$-alkyl, preferably ethyl, and Re is hydrogen or a nitrogen protecting group.

In one embodiment of SCHEME 9, 9-A or 9-AA, the compound of formula (I) is obtained by a process as depicted in SCHEME 1, optionally including the reaction steps as depicted in SCHEMEs 2 to 4, or by a process as depicted in SCHEME 3*, optionally including the reaction steps as depicted in SCHEME 4.

In a further embodiment, the process as depicted in SCHEMEs 5 to 10 is continued by transforming the obtained compound of formula (VIII) or a salt thereof (VIII)

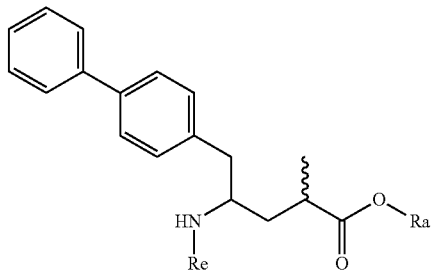

preferably of formula (VIII-a), or a salt thereof (VIII-a)

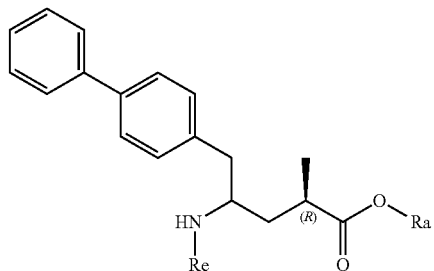

more preferably of formula (VIII-aa), or a salt thereof (VIII-aa)

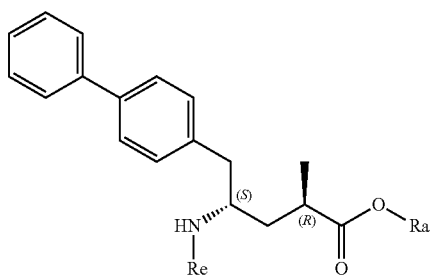

wherein Ra is selected from hydrogen and $C_1$-$C_6$-alkyl, preferably ethyl, and Re is selected from hydrogen and a nitrogen protecting group,
into a compound of formula (10)

preferably of formula (10-a)

(10-a)

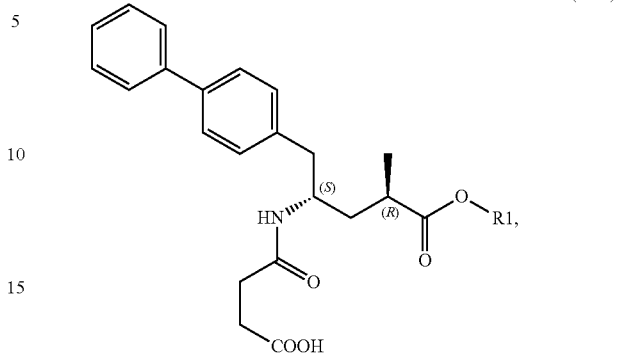

wherein R1 is hydrogen or $C_1$-$C_6$-alkyl, preferably ethyl, in particular to the compound N-(3-carboxy-1-oxopropyl)-(4S)-p-phenylphenylmethyl)-4-amino-(2R)-methylbutanoic acid or a salt thereof, or N-(3-carboxy-1-oxopropyl)-(4S)-p-phenylphenylmethyl)-4-amino-(2R)-methylbutanoic acid ethyl ester or a salt thereof, by optionally removing—if present—any nitrogen protecting group Re, optionally reacting the obtained compound of formula (VIII) wherein Ra and Re are hydrogen with a coupling reagent in the presence of a $C_1$-$C_6$-alkanol, preferably ethanol, to provide the compound of formula (VIII), wherein Ra is selected from $C_1$-$C_6$-alkyl, preferably ethyl, and Re is hydrogen, and reacting the compound of formula (VIII) wherein Ra is selected from hydrogen and $C_1$-$C_6$-alkyl, preferably ethyl, and Re is hydrogen, with succinic acid anhydride.

In a fourth aspect, the present invention provides the use of a novel compound of formula (XV), in particular of formula (I) or (II), of a novel compound of formula (XVI), in particular of formula (X), (XVII), (XVII*), (XVII**), (XVIII), and (IX), or the preferred stereoisomer thereof, as depicted above, in the manufacture of a compound of formula (10)

(10)

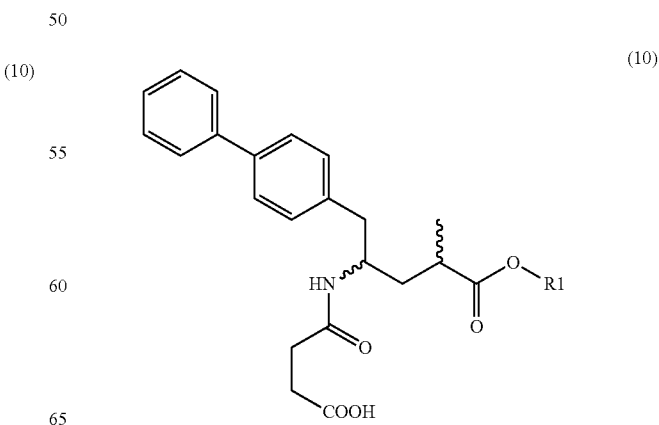

preferably of formula (10-a)

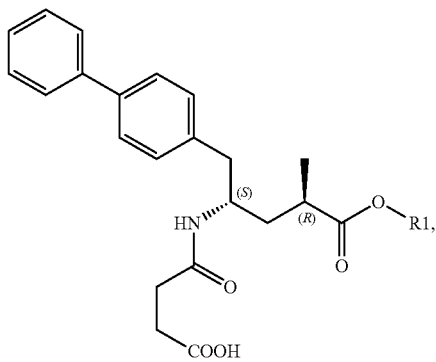

(10-a)

wherein R1 is hydrogen or $C_1$-$C_6$-alkyl, preferably ethyl, preferably in the manufacture of N-(3-carboxyl-1-oxopropyl)-(4S)-(p-phenylphenylmethyl)-4-amino-(2R)-methyl butanoic acid, or salts thereof, or N-(3-carboxyl-1-oxopropyl)-(4S)-(p-phenylphenylmethyl)-4-amino-(2R)-methyl butanoic acid ethyl ester (known in the art as AHU377 or sacubitril) or salts thereof.

In further embodiments, the invention relates to any one or more of the novel compounds, processes and uses as represented in the claims, which are incorporated here by reference.

The invention also relates to any sequential combination of the process steps described above and below.

In its above mentioned aspects which are also given in more detail below the present invention provides the following advantages: The synthesis route is suitable for industrial scale processing. The synthesis route is economically and environmentally favorable. The compounds of formula (I) and (XVI) which are intermediates desired for the synthesis of sacubitril can be produced with high yield and high stereo-selectivity.

DETAILED DESCRIPTION OF THE INVENTION

General Terms

The general definitions used above and below, unless defined differently, have the following meanings, where replacement of one or more or all expressions or symbols by the more specific definitions can be made independently for each invention embodiment and lead to more preferred embodiments.

Where the plural form is used for compounds, starting materials, intermediates, salts, pharmaceutical preparations, diseases, disorders and the like, this intends to mean one (preferred) or more single compound(s), salt(s), pharmaceutical preparation(s), disease(s), disorder(s) or the like, where the singular or the indefinite article ("a", "an") is used, this does not intend to exclude the plural, but only preferably means "one".

Chiral Compounds

The term "chiral" refers to molecules which have the property of non-superimposability on their mirror image partner, while the term "achiral" refers to molecules which are superimposable on their mirror image partner.

In the formulae of the present application the term " $\sim\sim\sim$ " on a C-sp³ represents a covalent bond, wherein the stereochemistry of the bond is not defined. This means that the term " $\sim\sim\sim$ " on a C-sp³ comprises an (S) configuration as well as an (R) configuration of the respective chiral centre. Furthermore, mixtures, e.g. mixtures of enantiomers such as racemates, are also encompassed by the present invention. Especially preferred are single stereoisomers of the compounds of the formula (1) or (2), especially the specific ones of formula (1-a) and (1-b).

In the formulae of the present application the term " $\sim\sim\sim$ " on a C-sp² represents a covalent bond, wherein the stereochemistry or the geometry of the bond is not defined. This means that the term " $\sim\sim\sim$ " on a C-sp² comprises a (Z) configuration as well as a (E) configuration of the respective double bond. Furthermore, mixtures, e.g., mixtures of double bond isomers are also encompassed by the present invention.

In the formulae of the present application the term " ⁄ " on a C-sp³ indicates the absolute stereochemistry, either (R) or (S).

In the formulae of the present application the term " ⁄ " on a C-sp³ indicates the absolute stereochemistry, either (R) or (S).

In the formulae of the present application, the term "-------" indicates a C-sp³-C-sp³ bond or a C-sp²-C-sp² bond.

The compounds of the present invention can possess one or more asymmetric centers. The preferred absolute configurations are as indicated herein specifically. However, any possible pure enantiomer, pure diastereoisomer, or mixtures thereof, e.g., mixtures of enantiomers, such as racemates, are encompassed by the present invention.

Compounds with a stereogenic center but without indication of a specific configuration are considered mixtures of compounds with the respective configurations, e.g. R,R; R,S; S,R and SS, or pure enantiomers/diastereomers.

Stereoisomeric, especially enantiomeric, purity, is where mentioned referring to all diastereomers of the compound taken together (100%). It is determined by chiral chromatography (examples include HPLC, uPLC and GC) or NMR (with addition of chiral entities and or metals). Specific examples of methods include: chiral HPLC equipped with chiral column Chiralpak ID 4.6 mm ø×250 mm, 5 µm (Daicel Corporation, Osaka, Japan) at 25° C.; mobile phase Hept:EtOAc:$CH_3$CN, 90:8:2.

The term "substantially optically pure" compound, as defined herein, refers to a compound obtained by a process according to the invention wherein the compound has an optical purity of at least 70% (ee=enantiomeric excess), more preferably of at least 90% (ee) and most preferably at least 95% (ee) or more, such as 100% (ee). The optical purity is given in % excess of one enantiomer over the other enantiomer. Thus, the optical purity in % is the quotient of the difference between the (R) and the (S) enantiomer concentrations and the sum of the concentrations of both enantiomers (optical purity of A in %=([A]−[B]):([A]+[B])× 100, wherein A and B represent the concentrations of the (R) and (S) enantiomers or vice versa).

Prodruqs

The term "pro-drug", as used herein, represents in particular compounds which are transformed in vivo to the parent compound, for example, by hydrolysis in blood, for example as described in T. Higuchi and V. Stella, "Pro-drugs as Novel Delivery Systems", volume 14 of the ACS Symposium Series; Edward B. Roche, editor, "Bioreversible Carriers in Drug Design", American Pharmaceutical Association and Pergamon Press, 1987; H Bundgaard, editor, "Design of Prodrugs", Elsevier, 1985; Judkins et al. *Synthetic Communications* 1996, 26, 4351-4367, and "The Organic Chemistry of Drug Design and Drug Action", second edition, R. B. Silverman (particularly chapter 8, pages 497-557), Elsevier Academic Press, 2004.

Pro-drugs therefore include drugs having a functional group which has been transformed into a reversible derivative thereof. Typically, such prodrugs are transformed to the active drug by hydrolysis. As examples may be mentioned the following:

| Functional Group | Reversible derivative |
| --- | --- |
| Carboxylic acid | Esters, including e.g. alkyl esters |
| Alcohol | Esters, including e.g. sulfates and phosphates as well as carboxylic acid esters |
| Amine | Amides, carbamates, imines, enamines, |
| Carbonyl (aldehyde, ketone) | Imines, oximes, acetals/ketals, enol esters, oxazolidines and thiazoxolidines |

Pro-drugs also include compounds convertible to the active drug by an oxidative or reductive reaction. As examples may be mentioned:
Oxidative Activation
N- and O-dealkylation
Oxidative deamination
N-oxidation
Epoxidation
Reductive Activation
Azo reduction
Sulfoxide reduction
Disulfide reduction
Bioreductive alkylation
Nitro reduction
NEP Inhibitor The term "NEP inhibitor" describes a compound which inhibits the activity of the enzyme neutral endopeptidase (NEP, EC 3.4.24.11).

In the present invention the terms "NEP-inhibitor" or "NEP-inhibitor prodrug" relates to the substances as such or to salts thereof, preferably pharmaceutically acceptable salts thereof. Examples are sodium, potassium, magnesium, calcium or ammonium salts. Calcium salts are preferred.

The NEP inhibitor prodrug N-(3-carboxy-1-oxopropyl)-(4S)-p-phenylphenylmethyl)-4-amino-(2R)-methylbutanoic acid ethyl ester optionally may be further reacted to obtain the active NEP inhibitor N-(3-carboxy-1-oxopropyl)-(4S)-p-phenylphenylmethyl)-4-amino-(2R)-methylbutanoic acid, either in vitro or in vivo.

Transaminase:

In the context of the present invention, a transaminase is a pyridoxal-phosphate-dependent enzyme catalysing the transfer of an amino group ($NH_2$) from a primary amine to a carbonyl group ($C=O$) of an acceptor molecule. Transaminases are classified in E.C. 2.6.1.X. In a particularly preferred embodiment of the present invention, the transaminase is an (R)- or (S)-selective transaminase, particularly is in a preferred embodiment an ω-transaminase, in particular a (S)-selective ω-transaminase.

In the context of the present invention a ω-transaminase is an enzyme preferably with the classification code E.C.2.6.1.18. These amino transaminases are characterised in that they mainly use amines as substrates. These enzymes are further characterised by exhibiting an equilibrium constant of ω-transaminase catalysed reactions which is greater than 1.

The present invention also understands under the term transaminase, in particular ω-transaminase, an extract of an organism, such as a microorganism or a cell, containing a transaminase, in particular an ω-transaminase, or a living or dead cell or microorganism itself comprising a transaminase, in particular an ω-transaminase. Such a microorganism or cell or extract or transaminase enzyme may be used in immobilised or non-immobilised form.

The transaminase, in particular the ω-transaminase, may also be a recombinantly produced naturally occurring (wild-type) or genetically modified transaminase, in particular an ω-transaminase, which is coded partially or completely by a nucleic acid sequence or a derivative thereof contained in one of the above-identified organisms or being equivalent thereto.

A recent overview of ω-transaminases which may be used and/or optimized to be used according to the present invention are described for instance in Koszelewski et al. (2010) Trends in Biotechnology, 28(6):324-332, and Malik at al (2012) Appl Microbiol Biotechnol.; 94(5):1163-71. Such transaminases can be obtained e.g. from microorganisms like *Chromobacterium violaceum, Vibrio fluvialis, Alcaligenes denitrificans, Klebsiella pneumoniae*, and *Bacillus thuringiensis* and others.

In one embodiment, the ω-transaminases used in the present invention were obtained from Codexis Inc. under the reference numbers ATA-217 (part of the Codex® ATA Screening Kit), as well as further genetically modified ω-transaminases variants thereof (also obtained from Codexis Inc.). Such genetically modified ω-transaminases are described e.g. in U.S. Pat. No. 8,470,564.

Coenzyme

Transaminases require the coenzyme Pyridoxal-5'-phosphate (PLP). "Pyridoxal-phosphate," "PLP," "pyridoxal-5'-phosphate," "PYP," and "P5P" are used interchangeably herein to refer to the compound that acts as a coenzyme in transaminase reactions.

In some embodiments, pyridoxal phosphate is defined by the structure 1-(4'-formyl-3'-hydroxy-2'-methyl-5'-pyridyl) methoxyphosphonic acid, CAS number [54-47-7], Pyridoxal-5'-phosphate can be produced in vivo by phosphorylation and oxidation of pyridoxol (also known as Vitamin B6). In transamination reactions using transaminase enzymes, the amine group of the amino donor is transferred to the coenzyme to produce a keto byproduct, while pyridoxal-5'-phosphate is converted to pyridoxamine phosphate. Pyridoxal-5'-phosphate is regenerated by reaction with a different keto compound (the amino acceptor). The transfer of the amine group from pyridoxamine phosphate to the amino acceptor produces a chiral amine and regenerates the coenzyme.

In some embodiments, the pyridoxal-5'-phosphate can be replaced by other members of the vitamin B6 family, including pyridoxine (PN), pyridoxal (PL), pyridoxamine (PM), and their phosphorylated counterparts; pyridoxine phosphate (PNP), and pyridoxamine phosphate (PMP).

Amine Donor

In the context of the present invention an amine donor is a molecule capable of providing an amino group to an amine acceptor using a transaminase, in particular an ω-transaminase. In a particular preferred embodiment the amine donor is an amine or amino acid.

In some embodiments, amino donors are molecules of the following general formula,

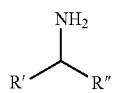

in which each of R' and R", when taken independently, is an alkyl, cycloalkyl, heterocycloalkyl, aryl, or heteroaryl, which is unsubstituted or substituted with one or more enzymatically non-inhibiting groups. R' can be the same or different from R" in structure or chirality. In some embodiments, R' and R", taken together, may form a ring that is unsubstituted, substituted, or fused to other rings. Typical amino donors that can be used include chiral and achiral amino acids, and chiral and achiral amines. Amino donors that can be used include, by way of example and not limitation, isopropylamine (2-aminopropane), 1-alanine, alanine, in particular D,L-alanine, L-alanine or D-alanine, α-methylbenzylamine (α-MBA), glutamate, phenylalanine, glycin, 3-aminobutyrate, 2-aminobutane, γ-aminobutyrate and a salt, for instance a chloride, of any one thereof. In a preferred embodiment thereof, isopropylamine (2-aminopropane) is the amine donor.

In such an embodiment, the obtained ketone product will be acetone, phenylpyruvic acid, a salt thereof, pyruvic acid, a salt thereof, glyoxylic acid, a salt thereof, acetophenone, 2-ketoglutarate, 3-oxobutyrate, 2-butanone, 3-oxopyrrolidine (3-OP), 3-pyridylmethylketone (3-PMK), 3-oxobutyric acid ethyl ester (3-OBEE), 3-oxopentanoic acid methyl ester (3-OPME), N-1-boc-3-oxopiperidinone and N-1-boc-3-oxopyrrolidine (B3OP) or a salt, for instance a chloride, of any one thereof. In a preferred embodiment thereof, the obtained ketone product is acetone.

Enzymatic Reaction Conditions:

"Suitable reaction conditions" refer to those conditions in the transaminase catalyzed reaction solution (e.g., ranges of enzyme loading, substrate loading, cofactor loading, temperature, pH, buffers, co-solvents, etc.) under which the selected transaminase is capable of converting a substrate compound to a product compound (e.g., conversion of the compound of formula (I), preferably (I-a), to the compound of formula (VIII), preferably (VIII-a), in particular (VIII-aa)). Exemplary "suitable reaction conditions" are provided in the present disclosure and illustrated by the Examples.

"Loading", such as in "compound loading" or "enzyme loading" or "cofactor loading" refers to the concentration or amount of a component in a reaction mixture at the start of the reaction.

"Substrate" in the context of the transaminase catalyzed reaction process refers to the compound or molecule acted on by the enzyme. For example, an exemplary substrate for the transaminase in the process disclosed herein is compound (I).

"Product" in the context of the transaminase catalyzed reaction process refers to the compound or molecule resulting from the action of the enzyme. For example, an exemplary product for the transaminase in the process disclosed herein is compound (VIII).

In the context of the present invention, the transaminase reaction is enantioselective, i.e. produces the desired enantiomer in excess of the undesired enantiomer (in the context of the present invention, the term enantiomer refers to the specific stereogenic centre where the amine group is introduced; since the preferred substrate already contains a stereogenic center, in practice the desired compound should have diastereomeric purity). In some embodiments, the desired enantiomer is formed in at least 70%, 80%, 85%, 90%, 91%, 92%, 93%, 94%, 95%, 96%, 97%, 98%, 99% or greater enantiomeric excess (ee).

In the present invention it is preferred that the amino acceptor is converted to the desired chiral amine compound in a conversion rate of more than 50%, or at least 60, 70, 80, 90, 95, 99, in particular 100%.

Substituent Definitions

Alkyl is defined as a radical or part of a radical as a straight or branch (one or, if desired and possible, more times) carbon chain, and is especially $C_1$-$C_7$-alkyl, preferably $C_1$-$C_6$-alkyl, more preferably $C_1$-$C_4$-alkyl.

The terms "$C_1$-$C_7$-", "$C_1$-$C_6$-" and "$C_1$-$C_4$-", respectively, define a moiety with up to and including maximally 7, especially up to and including maximally 6 and 4 respectively, carbon atoms, said moiety being branched (one or more times) or straight-chained and bound via a terminal or a non-terminal carbon.

Cycloalkyl is, for example, $C_3$-$C_7$-cycloalkyl and is, for example, cyclopropyl, cyclobutyl, cyclopentyl, cyclohexyl and cycloheptyl. Cyclopentyl and cyclohexyl are preferred.

Alkoxy is, for example, $C_1$-$C_7$-alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$-$C_4$-alkoxy is preferred.

Alkanoyl is, for example, $C_2$-$C_8$-alkanoyl and is, for example, acetyl [—C(═O)Me], propionyl, butyryl, isobutyryl or pivaloyl. $C_2$-$C_5$-Alkanoyl is preferred, especially acetyl.

Halo or halogen is preferably fluoro, chloro, bromo or iodo, most preferably, chloro, bromo, or iodo.

Halo-alkyl is, for example, halo-$C_1$-$C_7$-alkyl and is in particular halo-$C_1$-$C_4$-alkyl, such as trifluoromethyl, 1,1,2-trifluoro-2-chloroethyl or chloromethyl. Preferred halo-$C_1$-$C_7$-alkyl is trifluoromethyl.

Alkenyl may be linear or branched alkyl containing a double bond and comprising preferably 2 to 12 carbon atoms, 2 to 10 carbon atoms being especially preferred. Particularly preferred is a linear $C_2$-$C_7$-alkenyl, more preferably $C_2$-$C_4$-alkenyl. Some examples of alkyl groups are ethyl and the isomers of propyl, butyl, pentyl, hexyl, heptyl, octyl, nonyl, decyl, undecyl, dodecyl, tetradecyl, hexadecyl, octacyl and eicosyl, each of which containing a double bond. Especially preferred is allyl.

Alkylene is a bivalent radical derived from $C_{1-7}$-alkyl and is especially $C_2$-$C_7$-alkylene or $C_2$-$C_7$-alkylene and, optionally, can be interrupted by one or more, e.g. up to three oxygen, NR14 or sulfur, wherein R14 is alkyl, each of which can be unsubstituted or substituted, by one or more substituents independently selected from for example, $C_1$-$C_7$-alkyl, $C_1$-$C_7$-alkoxy-$C_1$-$C_7$-alkyl or $C_1$-$C_7$-alkoxy.

Alkenylene is a bivalent radical derived from $C_{2-7}$-alkenyl and can be interrupted by one or more, e.g. up to three oxygen, NR14 or sulfur, wherein R14 is alkyl, and is unsubstituted or substituted by one or more, e.g. up to three substitutents, preferably independently selected from the substituents mentioned above for alkylene.

Aryl being a radical or part of a radical is, for example $C_{6-10}$-aryl, and is preferably a mono- or polycyclic, especially monocyclic, bicyclic or tricyclic aryl moiety with 6 to 10 carbon atoms, such as phenyl, naphthyl or fluorenyl preferably phenyl, and which can be unsubstituted or substituted, by one or more substituents, independently selected from, e.g. $C_1$-$C_7$-alkyl, $C_1$-$C_7$-alkoxy-$C_1$-$C_7$-alkyl or $C_1$-$C_7$-alkoxy.

The term arylalkyl refers to aryl-$C_1$-$C_7$-alkyl, wherein aryl is as defined herein and is for example benzyl.

The term carboxyl refers to —$CO_2H$.

Aryloxy refers to an aryl-O— wherein aryl is as defined above.

Unsubstituted or substituted heterocyclyl is a mono- or polycyclic, preferably a mono-, bi- or tricyclic-, most preferably mono-, unsaturated, partially saturated, saturated or aromatic ring system with preferably 3 to 14 (more preferably 5 to 14) ring atoms and with one or more, preferably one to four, heteroatoms, independently selected from nitrogen, oxygen, sulfur, S(=O)— or S—(=O)$_2$, and is unsubstituted or substituted by one or more, e.g. up to three substitutents, preferably independently selected from the group consisting of halo, $C_1$-$C_7$-alkyl, halo-$C_1$-$C_7$-alkyl, $C_1$-$C_7$-alkoxy, halo-$C_1$-$C_7$-alkoxy, such as trifluoromethoxy and $C_1$-$C_7$-alkoxy-$C_1$-$C_7$-alkoxy. When the heterocyclyl is an aromatic ring system, it is also referred to as heteroaryl. Heterocyclyl is preferably imizazolyl, pyrazolyl, oxazolyl, isoxazolyl, thiazolyl, isothiazolyl, pyridinyl, pyranyl, diazionyl, oxazinyl, thiazinyl, dioxinyl, dithiinyl, azepanyl, oxepanyl, thiepanyl, indolyl, isoindoly, quinolinyl, isoquinolinyl, benzazepinyl, carbazolyl, imidazolidinyl, pyrazolidinyl, oxazolidinyl, isoxazolinidyl, thiazolidy, dioxolanyl, dithiolanyl, furazanyl, oxadiazolyl, thiadiazolyl, dithiazolyl, tetrazolyl, piperidinyl, piperazinyl, morpholinyl, thiomorpholinyl, oxothiomorpholinyl, dioxothiomorpholinyl, dioxanyl, dithianyl, azepanyl, oxepanyl, thiepanyl, or benzo-fused variants thereof.

In heterocyclylalkyl, the heterocyclyl is preferably as just defined and is attached to an alkyl as defined for alkyl. Examples are imidazolylmethyl, pyridylmethyl or piperidinylmethyl.

Acetyl is —C(=O)$C_1$-$C_7$-alkyl, preferably —C(=O)Me.

Sulfonyl is (unsubstituted or substituted)$C_1$-$C_7$-alkylsulfonyl, such as methylsulfonyl, (unsubstituted or substituted) phenyl- or naphthyl-$C_1$-$C_7$-alkylsulfonyl, such as phenylmethanesulfonyl, or (unsubstituted or substituted) phenyl- or naphthyl-sulfonyl; wherein if more than one substituent is present, e.g. one to three substitutents, the substituents are selected independently from cyano, halo, halo-$C_1$-$C_7$-alkyl, halo-$C_1$-$C_7$-alkyloxy- and $C_1$-$C_7$-alkyloxy. Especially preferred is $C_1$-$C_7$-alkylsulfonyl, such as methylsulfonyl, and (phenyl- or naphthyl)-$C_1$-$C_7$-alkylsulfonyl, such as phenylmethanesulfonyl.

Sulfenyl is (unsubstituted or substituted) $C_{6-10}$-aryl-$C_1$-$C_7$-alkylsulfenyl or (unsubstituted or substituted) $C_{6-10}$-arylsulfenyl, wherein if more than one substituent is present, e.g. one to four substitutents, the substituents are selected independently from nitro, halo, halo-$C_1$-$C_7$-alkyl and $C_1$-$C_7$-alkyloxy.

Imide refers to a (unsubstituted or substituted) functional group consisting of two acyl groups bound to nitrogen, preferably a cyclic group derived from dicarboxylic acids. Especially preferred is succinimidyl derived from succinic acid or phthalimidyl derived from phthalic acid. The imidyl group may be substituted by one or more substituents independently selected from for example, $C_1$-$C_7$-alkyl, $C_1$-$C_7$-alkoxy-$C_1$-$C_7$-alkyl, $C_1$-$C_7$-alkoxy or halo.

Azide refers to a group —N=$N^+$=$N^-$. Silyl, as used herein, refers to a group according to the formula —SiR11R12R13, wherein R11, R12 and R13 are, independently of each other, $C_1$-$C_7$-alkyl, $C_6$-$C_{10}$-aryl or phenyl-$C_1$-$C_4$-alkyl. Preferred examples for R11, R12 and R13 are methyl, ethyl, isopropyl, tert-butyl, phenyl or phenyl-$C_{14}$-alkyl.

Salts

Salts are especially pharmaceutically acceptable salts or generally salts of any of the intermediates mentioned herein, except if salts are excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, any of the intermediates mentioned herein may also form internal salts.

For isolation or purification purposes of any of the intermediates mentioned herein it is also possible to use pharmaceutically unacceptable salts, for example picrates or perchlorates.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter is to be understood as referring also to one or more salts thereof or a mixture of a corresponding free compound, intermediate or starting material and one or more salts thereof, each of which is intended to include also any solvate or salt of any one or more of these, as appropriate and expedient and if not explicitly mentioned otherwise. Different crystal forms may be obtainable and then are also included.

Nitrogen Protecting Groups

The term "nitrogen protecting group" comprises any group which is capable of reversibly protecting a nitrogen functionality, preferably an amine and/or amide functionality. Preferably the nitrogen protecting group is an amine protecting group and/or an amide protecting group. Suitable nitrogen protecting groups are conventionally used e.g. in peptide chemistry and are described e.g. in the relevant chapters of standard reference works such as J. F. W. McOmie, "Protective Groups in Organic Chemistry", Plenum Press, London and New York 1973, in P. G. M. Wuts and T. W. Greene, "Greene's Protective Groups in Organic Synthesis', fourth edition, Wiley, New Jersey, 2007, and "The Peptides"; volume 3 (editors: E. Gross and J. Meienhofer), Academic Press, London and New York 1981, and "Methoden der organischen Chemie" (Methods of Organic Chemistry), Houben Weyl, fourth edition, volume 15/I, Georg Thieme Verlag, Stuttgart 1974.

Preferred nitrogen protecting groups generally comprise: unsubstituted or substituted $C_1$-$C_6$-alkyl, preferably $C_1$-$C_4$-alkyl, more preferably $C_1$-$C_2$-alkyl, most preferably $C_1$-alkyl, unsubstituted or substituted $C_{2-4}$-alkenyl, wherein each $C_1$-$C_6$-alkyl and $C_{2-4}$-alkenyl is optionally mono-, di- or tri-substituted by trialkylsilyl-$C_1$-$C_7$-alkoxy (e.g. trimethylsilylethoxy), cycloalkyl, aryl, preferably phenyl, or a heterocyclic group, preferably pyrrolidinyl, wherein the cycloalkyl group, the aryl ring or the heterocyclic group is unsubstituted or substituted by one or more, e.g. two or three residues, e.g. selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$; aryl-$C_1$-$C_2$-alkoxycarbonyl (preferably phenyl-$C_1$-$C_2$-alkoxycarbonyl e.g. benzyloxycarbonyl); $C_1$-10-alkenyloxycarbonyl; $C_{1-6}$-alkylcarbonyl (e.g. acetyl or pivaloyl); $C_{6-10}$-arylcarbonyl; $C_{1-6}$-alkoxycarbonyl (e.g. tert-butoxycarbonyl); $C_{6-10}$-aryl-$C_{1-6}$-alkoxycarbonyl; allyl or cinnamyl; sulfonyl or sulfenyl; a succinimidyl group, substituted silyl, e.g. triarylsilyl or trialkylsilyl (e.g. triethylsilyl).

Examples of preferred nitrogen protecting groups are acetyl, benzyl, cumyl, benzhydryl, trityl, benzyloxycarbonyl (Cbz), 9-fluorenylmethyloxycarbony (Fmoc), benzyloxymethyl (BOM), pivaloyl-oxy-methyl (POM), trichloroethxoycarbonyl (Troc), 1-adamantyloxycarbonyl (Adoc), allyl, allyloxycarbonyl, trimethylsilyl, tert-butyl-dimethylsilyl (TBDMS), triethylsilyl (TES), triisopropylsilyl (TIPS), trimethylsilylethoxymethyl (SEM), tert-butoxycarbonyl (BOC), tert-butyl, 1-methyl-1,1-dimethylbenzyl, (phenyl)methylbenzene, pyrridinyl and pivaloyl. Most preferred nitrogen protecting groups are acetyl, benzyl, benzyloxycarbonyl (Cbz), triethylsilyl (TES), trimethylsilyethoxymethyl (SEM), tert-butoxycarbonyl (BOC), pyrrolidinylmethyl and pivaloyl.

Examples of more preferred nitrogen protecting groups are, pivaloyl, pyrrolidinylmethyl, t-butoxycarbonyl, benzyl and silyl groups, particularly silyl groups according to the formula SiR11R12R13 group, wherein R11, R12 and R13 are, independently of each other, $C_1$-$C_7$-alkyl, $C_6$-$C_{10}$-aryl or phenyl-$C_1$-$C_4$-alkyl. Preferred examples for R11, R12 and R13 are methyl, ethyl, isopropyl, t-butyl and phenyl.

Examples of most preferred nitrogen protecting groups are tert-butoxycarbonyl (BOC), benzoyl, styryl, 1-butenyl, benzyl, p-methoxybenzyl (PMB) and pyrrolidinylmethyl, in particular pivaloyl and tert-butoxycarbonyl (BOC).

In one embodiment the term nitrogen protecting group refers to a group which is selected from the group consisting of $C_1$-$C_6$-alkyl, which is unsubstituted or mono-, di- or tri-substituted by tri-$C_1$-$C_6$-alkylsilyl$C_1$-$C_7$-alkoxy, $C_6$-$C_{10}$-aryl, or a heterocyclic group being a mono-, bi- or tricyclic ring system with 5 to 14 ring atoms and 1 to 4 heteroatoms independently selected from N, O, S, S(O) or $S(O)_2$, wherein the aryl ring or the heterocyclic group is unsubstituted or substituted by one, two or three residues, selected from the group consisting of $C_1$-$C_7$-alkyl, hydroxyl, $C_1$-$C_7$-alkoxy, $C_2$-$C_8$-alkanoyl-oxy, halogen, nitro, cyano, and $CF_3$;

$C_6$-$C_{10}$-aryl-$C_1$-$C_2$-alkoxycarbonyl; $C_1$-$C_{10}$-alkenyloxycarbonyl; $C_1$-$C_6$-alkylcarbonyl; $C_6$-$C_{10}$-arylcarbonyl; $C_1$-$C_6$-alkoxycarbonyl; $C_6$-$C_{10}$-aryl-$C_1$-$C_6$-alkoxycarbonyl; allyl; cinnamyl; sulfonyl; sulfenyl; succinimidyl, and silyl, wherein each silyl group is a SiR11R12R13 group, wherein R11, R12 and R13 are, independently of each other, $C_1$-$C_7$-alkyl, $C_6$-$C_{10}$-aryl or phenyl-$C_1$-$C_4$-alkyl.

Generally, in the present application the term "nitrogen protecting group" comprises any group which is capable of reversibly protecting an amino functionality.

If an embodiment requires the removal of the nitrogen protecting group, as defined above, the removal usually can be carried out by using known methods. e.g. as described in the references cited above. Preferably, the nitrogen protecting group, as defined above, is removed by using acidic or basic conditions. Examples for acidic conditions are hydrochloric acid, trifluoroacetic acid, sulphuric acid. Examples of basic conditions are lithium hydroxide, sodium ethoxide. Nucleophiles such as sodium borohydride can be used. In the case of N-benzyl as amino protecting group it can be removed by hydrogenation or by the use of some suitable oxidizing agents, e.g. ceric ammonium nitrate (CAN) or 2,3-dichloro-5,6-dicyano-p-benzoquinone (DDQ).

Carboxyl Protecting Groups

A carboxyl protecting group (e.g. Ra or R* in this disclosure) can be any group known in the art, especially $C_1$-$C_6$-alkyl, e.g. ethyl, methyl, allyl or tert-butyl, or $C_6$-$C_{10}$-aryl-$C_1$-$C_6$-alkyl, e.g. benzyl, or a silyl group SiR11R12R13, wherein R11, R12, and R13 are, independently of each other, $C_1$-$C_7$-alkyl, $C_6$-$C_{10}$-aryl or phenyl-$C_1$-$C_4$-alkyl. Preferred examples for R11, R12 and R13 are methyl, ethyl, isopropyl, tert-butyl, phenyl or phenyl-$C_{1-4}$-alkyl. The carboxyl protecting groups themselves, their introduction reactions, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosauren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

For example, an $C_1$-$C_6$-alkyl, e.g. ethyl, protecting group R* or Ra can be removed by hydrolysis, e.g. in the presence of a base, such as an alkaline metal hydroxide, e.g. lithium hydroxide, in the presence of an appropriate solvent, e.g. a cyclic ether, such as tetrahydrofuran, and water, e.g. at a temperature in the range from 0 to 50° C., such as from 10 to 30° C.

Generally this implies that wherever the term "protecting group" is used in the present specification, a protecting group is only used as such if it is removed for the next to follow product—if it remains, the protecting group is becoming a substituent. Thus, alkyl, such as ethyl, if removed, is a protecting group, if it remains, it becomes a permanent moiety.

Where protecting groups are mentioned, it is their characteristic that, in contrast to groups that remain in a molecule, they are cleaved off in a following reaction step; therefore alkyl, such as ethyl, as protecting group, based on this function, is to be distinguished from alkyl, such as ethyl, that is to stay in a reaction product.

Embodiments

The following sections describes in more detail, as necessary the individual process steps as laid out in SCHEMES 1 to 10 above.

Reaction According to Schemes 1 and 1-A

In one embodiment of the invention, the deprotection and decarboxylation reactions preferably take place in the presence of an acid such as an inorganic acid, e.g. a hydrohalic acid, such as hydrochloric acid, in an appropriate solvent or solvent mixture, e.g. in a mixture of an organic acid, such as acetic acid, and water, e.g. at elevated temperatures from 50° C. to the reflux temperature of the reaction mixture, such as from 90 to 120° C.; or with an alkali hydroxide, such as sodium hydroxide, in an appropriate solvent or solvent mixture, such as an alcohol, e.g. ethanol, or an ether, e.g. tetrahydrofurane or 1,4-dioxane at temperatures e.g. in the range of from 30° C. to the reflux temperature of the reaction mixture, e.g. from 40 to 90° C., followed by acidification, e.g. with HCl, for decarboxylation; or with an alkali chloride, such as sodium chloride, in the presence of an appropriate solvent, e.g. DMSO e.g. at elevated temperatures from 50° C. to the reflux temperature of the reaction mixture, such as from 90 to 160° C. (Krapcho decarboxylation); or in the case that R* is tert-butyl and Ra is a (not removed) ethyl, in the presence of an acid, such as trifluoroacetic acid in an appropriate solvent or solvent mixture and at customary temperatures; or if R* is benzyl or allyl, by hydrogenation in the presence of a hydrogenation catalyst, such as a noble metal, e.g. Pd or Pd on charcoal, in an appropriate solvent or solvent mixture, e.g. an alcohol, such as methanol or ethanol.

The introduction of a moiety Ra other than hydrogen into a deprotected and decarboxylated compound (wherein instead of the moiety Ra a hydrogen is present) can preferably be conducted from the corresponding resulting compound of the formula (I), especially (I-a) wherein Ra is hydrogen by reaction with an alcohol of the formula Ra—OH, wherein Ra is as defined for a compound of the formula (I), especially Ra is $C_1$-$C_6$-alkyl, such as ethyl, in the presence of an activating agent, e.g. an agent to transform the acid into an acyl halide or acid anhydride.

Suitable reagents for formation of an acyl halide are for example selected from thionyl chloride, thionyl bromide, $PCl_3$, $PCl_5$, oxalyl chloride, $Me_2C=C(Cl)NMe_2$, PhCOCl, $PBr_3$, $PBr_5$, $Ph_3PBr_2$, oxalyl bromide or $Me_2C=C(Br)NMe_2$.

The reaction preferably takes place in a customary solvent, such as an $C_1$-$C_6$-alkyl-alcohol, e.g. methanol or ethanol, and at appropriate temperatures, e.g. in the range from 0 to 100° C., e.g. from 10 to 90° C.

Reaction According to Schemes 2 and 2-A

In one embodiment of the invention, for the propionate derivative of the formula (IV), preferably of formula (IV-a), the leaving group X is preferably halo, e.g. bromo, iodo or chloro, or an activated alcohol group, e.g. mesylate or tosylate.

This reaction preferably takes place in the presence of a tetraalkylammonium halogenide, e.g. tetrabutylammonium iodide, and a base, e.g. an alkali metal carbonate, such as potassium carbonate, in an appropriate solvent, e.g. acetone, preferably at temperatures in the range from −10 to 50° C., e.g. at −5 to 30° C. Alternative conditions for this transformation are e.g. (a) tetrabutylammonium hydrogen sulfate in toluene at reflux (c.f. e.g. Monatshefte fir Chemie 1990, 121, 173-187), (b) sodium alkoxide in alcohols at elevated temperatures (e.g. sodium methoxide in methanol at reflux) (c.f. e.g. (a) J. Org. Chem. 1989, 54, 1876-1883; (b) Tetrahedron Lett. 1984, 25, 1047-1048; (c) J. Org. Chem. 1998, 63, 3677-3679), potentially in the presence of copper(I) salts (e.g. bromide) and a trialkylamine (e.g. triethylamine) (c.f. e.g. Synthesis 1985, 1043-1047) or (c) sodium hydride in THF (c.f. e.g. J. Org. Chem. 1995, 60, 5107-5113; (b) Tetrahedron Lett. 1993, 34, 2051-2054). These and other transformation conditions for alkylations of 1-dicarbonyl compounds are well-known to the person skilled in the art.

Reaction According to Scheme 3

The compound of the formula (III) can, in a further embodiment of the invention, preferably be obtained by a process comprising reaction of an acetic acid compound of the formula (V), or a reactive derivative thereof, with a salt of a malonic acid half ester of the formula (VI), wherein R* is a carboxyl protecting group.

Appropriate reaction conditions are well-known in the art. The reaction preferably takes place in the presence of a coupling reagent, such as N,N-carbonylimidazole, in an appropriate solvent or solvent mixture, e.g. an ether, such as tetrahydrofuran, and/or a nitrile, such as acetonitrile, in the presence of an alkaline earth metal salt, such as magnesium chloride, and a base, e.g. a tertiary nitrogen base, such as trimethylamine, at preferred temperatures in the range from −20 to 50° C., e.g. from −10 to 30° C. Alternative conditions (where the conditions can also be combined, that is, the modes for preparation of an activated acylating agent and for an activated methylene anion can be mixed)) for this transformation are e.g. (a) use of the corresponding acid chloride, e.g. prepared by treatment of the corresponding acid with oxalyl chloride or thionyl chloride, instead of the acyl imidazolide under otherwise identical conditions, or potentially in combination with the use of an trialkylamine or a pyridine base and Meldrum's acid (c.f. e.g. Bioorg. Med. Chem. 2015, 23, 149-159; (b) J. Am. Chem. Soc. 2006, 128, 6938-6946), (b) use of a coupling reagent, e.g. dicyclohexyl diimidazole in combination with Meldrum's acid in dichloromethane at 0-20° C. and subsequent opening of the intermediate product with an alcohol, e.g. ethanol, potentially in the presence of an acid catalyst, e.g. p-toluene sulfonic acid (c.f. e.g. US 2004/2508 A1), or (c) use of an activated mixed anhydride, e.g. prepared by treatment of the acid with an alkyl chloroformate, e.g. ethyl chloroformate, potentially in combination with an alkyl magnesium halide or an alkyl lithium reagent as base for deprotonation of the monoalkyl malonate alkali salt (c.f. e.g. J. Chem. Soc., Perkin Trans. 1, 2002, 1663-1671; (b) WO2008/36420 A2) in THF at reduced temperature, e.g. −30° C.

Reaction According to Schemes 3* and 3*-a

The compound of the formula (III) can, in a further embodiment of the invention, preferably be obtained by a process comprising reacting an intermediate compound of formula (XIV), preferably of formula (XIV-a), or a salt thereof, wherein Rf is selected from a group —O—R* wherein R* is selected from a carboxyl protecting group and $C_1$-$C_6$-alkyl, preferably methyl; —N(CH3)-O(CH3) (Weinreb-amide), morpholinyl, and imidazolinyl, with an in situ prepared activated dianionic derivative of the compound of formula (V), or a salt thereof, namely a compound of formula (V*), in the presence of a base, and followed by a decarboxylation reaction, to obtain the compound of formula (I), or a salt thereof wherein Ra is hydrogen.

The starting compound of formula (XIV) or (XIV-a) is known in the art and commercially available, or can be easily obtained from a compound of the following formula

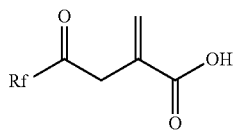

by methods known in the art; in particular the starting compound of formula (XIV-a) can be obtained e.g. by asymmetric hydrogenation in the presence of a chiral catalyst. Processes for the introduction of a particular preferred group Rf, e.g. a methoxy group, a Weinreb amide or secondary amide group are also well known in the art.

The activated dianionic derivative of the compound of formula (V), a so-called Ivanov-reagent (V*), can be prepared in situ by bis-deprotonation of the compound of formula (V) by treatment with very strong bases, e.g. alkyl lithium reagents, lithium amide bases or Grignard reagent (*Synthesis* 1982, 521-578 and references cited therein). The deprotonation is preferably performed by addition of a Grignard reagent, such as isopropyl magnesium chloride or sec-butyl magnesium bromide, preferably in the presence of LiCl (e.g. i-PrMgCl.LiCl, so-called TurboGrignard, available from Sigma-Aldrich, Cat No 656984), in an appropriate solvent, e.g. an ether, such as tetrahydrofuran, at preferred temperatures in the range from −20 to 50° C., e.g. from −10 to 40° C.

The activated dianionic derivative of formula (V*) is then added to the compound of formula (XIV) in the presence of a base, or alternative to a salt of the compound of formula (XIV). Suitable bases are e.g. a Grignard reagent, such as isopropyl magnesium chloride or sec-butyl magnesium bromide, or strong bases like sodium hydride. The addition is preferably performed in an appropriate solvent, e.g. an ether, such as tetrahydrofuran, at preferred temperatures in the range from −20 to 70° C., e.g. from −20 to 30° C., for a period of 1 h to 24 h.

The subsequent decarboxylation reaction then preferably takes place in the presence of an acid such as an inorganic acid, e.g. a hydrohalic acid, such as hydrochloric acid, in an appropriate solvent or solvent mixture, e.g. in a mixture of an organic acid, such as acetic acid, and water, or in an organic solvent, e.g. tetrahydrofuran, and is carried out at temperatures from 0° C. to room temperature. Alternatively, decarboxylation can also be achieved by heating to the reflux temperature of the solvent.

If necessary or desired, the obtained compound of formula (I), or a salt thereof, wherein Ra is hydrogen, can be reacted with an agent introducing a carboxyl protecting group, to provide the compound of formula (I), wherein Ra is a carboxyl protecting group, or the obtained compound of formula (I), or a salt thereof, wherein Ra is hydrogen, is reacted with a coupling reagent in the presence of an $C_1$-$C_6$-alkanol, especially ethanol, to provide the compound of formula (I), wherein Ra is $C_1$-$C_6$-alkyl, preferably ethyl, according to procedures as e.g. described for SCHEME 1 above or in the general part for carboxyl protectin groups.

Reaction According to Scheme 4

The compound of the formula (V) can, for example, in a further embodiment of the invention preferably be obtained by a process comprising hydrolysing a cyanide of the formula (VII).

The hydrolysis can preferably take place in the presence of a base, e.g. an alkali metal hydroxide, such as potassium hydroxide, in an appropriate solvent, e.g. an alcohol, such as a diol, e.g. ethylene glycol, at elevated temperatures, e.g. from 30° C. to the reflux temperature of the reaction mixture.

Alternatively, the compound of formula V (biphenyl acetic acid) is also available commercially (Sigma-Aldrich, catalogue no. 196487, CAS no. 5728-52-9).

Reaction According to Schemes 5 to 10:

As described above and also below, the processes forming embodiments of the invention, all in sequence, individually or in any combination, can be used in the synthesis of NEP inhibitors or prodrugs thereof, in particular NEP-inhibitors, or prodrugs thereof, such as sacubitril.

The compound of the formula (I), especially (I-a), can thus be used (in a further invention embodiment, alone or with the immediately or other preceding and following step or steps) in the manufacture of a compound of the formula (VIII), especially of the formula (VIII-a), or a salt thereof, respectively.

This transformation can be carried out in a number of different ways as detailed in SCHEMES 6 to 10.

Reaction According to Schemes 5, 5-a, and 5-Aa:

In one embodiment, the transformation comprises a process (forming an invention embodiment, alone or with the immediately or other preceding and following step or steps) which comprises reacting a compound of the formula (I), especially (I-a), wherein Ra is hydrogen, or a salt thereof, with ammonia, a primary or secondary amine, or salts thereof, yielding a compound of the formula (VIII), wherein Ra is hydrogen, if starting from a compound of the formula (I), especially (I-a), wherein Ra is hydrogen, or a salt thereof. Alternatively, the compound of the formula (VIII) can also be obtained from the compound of formula (I), especially formula (I-a), with a primary or secondary amine such as benzyl amine or a chiral benzyl amine, e.g. phenethylamine, to obtain the corresponding (benzyl-) protected amine, which is then transformed into the amino acid (VIII) by hydrogenolytic cleavage of the respective (benzyl-) protected amine.

Appropriate reaction conditions are well-known in the art. The reaction preferably takes place with an ammonium salt, e.g. ammonium formate, ammonium acetate or ammonium hydroxide, ammonia itself alone or in combination with titanium alkoxides, e.g. titanium isopropoxide, or hydroxylamine salts, such as the hydroxylamine hydrochloride, can also be used, the latter in combination with hydrogenation, with an appropriate reducing agent, such as sodium borohydride, sodium tris(acetoxy)borohydride or sodium cyanoborohydride, or reduction can also occur by hydrogenation, usually with Pd-catalysts (e.g. 10% Pd/C) or Raney-Ni; in an appropriate solvent or solvent mixture, e.g. in water, an alcohol, such as ethanol, and/or an ether, such as tetrahydrofuran, or a mixture of two or more thereof, at preferred temperatures in the range from 10 to 50° C. or up to 100° C., e.g. from 20 to 40 or up to 80° C.

This compound of the formula (VIII), especially (VIII-a), or a salt thereof, can then be used, in a further invention embodiment, for the manufacture of a corresponding compound of the formula (VIII), especially (VIII-a), wherein Ra is $C_1$-$C_6$-alkyl, e.g. by reacting a compound of the formula (VIII), especially (VIII-a), wherein Ra is hydrogen, with an agent introducing an amino protecting group, e.g. tert-butoxycarbonyl, followed by reaction of the amino protected analogue of the compound of the formula (VIII), especially (VIII-a), with an activating reagent, e.g. thionyl chloride, in the presence of an alcohol, especially ethanol, to yield the corresponding compound of the formula (VIII), especially (VIII-a), wherein Ra is $C_1$-$C_6$-alkyl, especially ethyl, e.g. at temperatures in the range from 50 to 80° C., e.g. 65 to 75° C.

Appropriate conditions and reagents that can be used for this sequence of steps directly or in an analogous way can, for example, be found in WO 2008/083967A, especially Examples 8 and 9 therein.

Reaction According to Schemes 6, 6-1, 6-a, and 6-aa:

In one embodiment, the transformation comprises a process (forming an invention embodiment, alone or with the immediately or other preceding and following step or steps), which comprises converting a compound of the formula (I), especially (I-a), or a salt thereof, wherein Ra is selected from hydrogen and $C_1$-$C_6$-alkyl, preferably hydrogen, into a compound of formula (VIII), in particular (VIII-a), preferably to the compound of formula (VIII-a), in particular (VIII-aa), wherein Ra is selected from hydrogen and $C_1$-$C_6$-alkyl, preferably hydrogen, and Re is hydrogen, or a salt thereof, by bringing it in contact with an (S)-selective ω-transaminase in the presence of an amine donor and a coenzyme.

The conversion rate from the compound of formula (I) to the compound of formula (VIII), preferably to the compound of formula (VIII-1), especially the conversion rate from the compound of formula (I-a) to the compound of formula (VIII-a), more preferably of formula (VIII-aa), is more than 50%, at least about 60%, at least about 70%, at least about 80%, at least about 90%, at least about 95%, at least about 98%, or at least about 99%., or even 100%.

In some embodiments, the transaminase is capable of converting the substrate compound of formula (I) and (I-a), respectively, in particular compound (R)-5-([1,1'-biphenyl]-4-yl)-2-methyl-4-oxopentanoic acid, to the product compound of formula (VIII-1) and (VIII-aa), respectively, in particular compound (2R,4S)-5-([1,1'-biphenyl]-4-yl)-4-amino-2-methylpentanoic acid, in enantiomeric excess (with regard to the stereogenic centre of the transamination) of greater than 80%, 85%, 90%, 91%, 92%, 93%, 94%, 95%, 96%, 97%, 98%, 99%, 99.5% or greater over the corresponding compound of formula (VIII-1b)

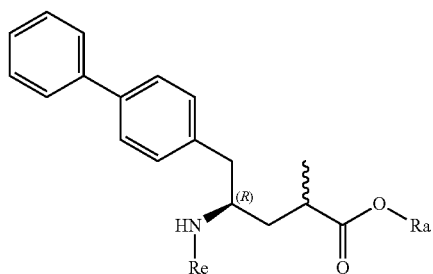

and (VIII-ab), respectively, (VIII-ab)

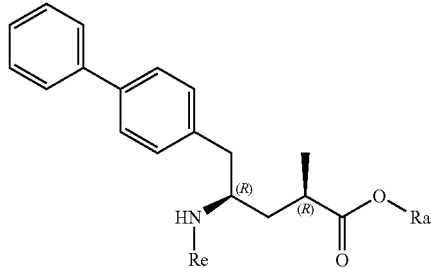

wherein Ra is selected from hydrogen and $C_1$-$C_6$-alkyl, preferably hydrogen, and Re is hydrogen, in particular over the compound (2R,4R)-5-([1,1'-biphenyl]-4-yl)-4-amino-2-methylpentanoic acid under suitable reaction conditions.

In some embodiments, the transaminases used in the instant disclosure are capable of converting compound (I) to compound (VIII-1) and compound (I-a) to compound (VIII-aa), respectively, with increased tolerance for the presence of substrate under suitable reaction conditions. Thus, in some embodiments the transaminases are capable of converting the substrate compound (I) and (I-a) to product compound (VIII-1) and (VIII-aa), respectively, in the presence of a substrate loading concentration of at least about 1 g/L, about 5 g/L, about 10 g/L, about 20 g/L, about 30 g/L, about 40 g/L, about 50 g/L, about 70 g/L, about 100 g/L, about 125 g/L, about 150 g/L, about 175 g/L or about 200 g/L or more. Such substrate loading still achieves a percent conversion of at least about 50%, at least about 60%, at least about 70%, at least about 80%, at least about 90%, at least about 95%, at least about 98%, or at least about 99%, or 100%, in a reaction time of about 120 h or less, about 96 h or less, about 72 h or less, about 48 h or less, about 36 h or less, or about 24 h or less, under suitable reaction conditions.

The suitable reaction conditions to achieve such conversion rates can be determined with respect to concentrations or amounts of transaminase, substrate, cofactor, buffer, co-solvent, pH, and/or conditions including temperature and reaction time, as further described below and in the Examples.

Detailed Methods of Using Transaminase Enzymes

For the foregoing processes, preferably the ω-transaminases obtainable from Codexis Inc. under the reference number ATA-217 (part of the Codex® ATA Screening Kit), as well as further genetically modified ω-transaminases variants thereof (also obtainable from Codexis Inc.) were used. Such genetically modified ω-transaminases are described e.g. in U.S. Pat. No. 8,470,564.

In the embodiments herein and illustrated in the Examples, various ranges of suitable reaction conditions that can be used in the processes, including but not limited, to ranges of amino donor, pH, temperature, buffer, solvent system, substrate loading, enzyme (transaminase) loading, cofactor loading, pressure, and reaction time. Further suitable reaction conditions for carrying out the claimed transaminase process can be readily optimized in view of the guidance provided herein by routine experimentation that includes, but is not limited to, contacting the transaminase and substrate compound under experimental reaction conditions of concentration, pH, temperature, solvent conditions, and detecting the product compound.

In one embodiment of the invention, the transaminase uses isopropylamine (also referred to herein as "IPM") as amine donor. Suitable reaction conditions comprise the amine donor, in particular IPM, present at a concentration of at least about 0.1 to about 3.0 M, 0.2 to about 2.5 M, about 0.5 to about 2 M or about 1 to about 2 M. In some embodiments, the amino donor is present at a concentration of about 0.1, 0.2, 0.3, 0.4, 0.5, 0.6, 0.7, 0.8, 1.0, 1.5, 2.0, 2.5 or 3.0 M. Higher concentrations of amine donor, e.g., IPM, can be used to shift the equilibrium towards amine product formation.

Suitable reaction conditions also typically comprise a cofactor. In one embodiment, the cofactors is pyridoxal-5'-phosphate (also known as pyridoxal-phosphate, PLP, P5P). In some embodiments, the cofactor PLP is present naturally in the cell extract and does not need to be supplemented. In other embodiments, the suitable reaction conditions comprise cofactor added to the enzyme reaction mixture, for example, when using partially purified, or purified transaminase enzyme. Suitable reaction conditions can comprise the presence of a cofactor preferably PLP, at a concentration of about 0.1 g/L to about 10 g/L, about 0.2 g/L to about 5 g/L, about 0.5 g/L to about 2.5 g/L. In some embodiments, the reaction conditions comprise a PLP concentration of about 0.1 g/L or less, 0.2 g/L or less, 0.5 g/L or less, 1 g/L or less, 2.5 g/L or less, 5 g/L or less, or 10 g/L or less. In some embodiments, the cofactor can be added either at the beginning of the reaction and/or additional cofactor is added during the reaction.

The concentration of the substrate compound of formula (I) or (I-a) in the reaction mixture can be varied, taking into consideration, for example, the desired amount of product compound, the effect of substrate concentration on enzyme activity, stability of enzyme under reaction conditions, and the percent conversion of substrate to product. In some embodiments, the suitable reaction conditions comprise a substrate compound loading of at least about 0.5 to about 200 g/L, 1 to about 200 g/L, 5 to about 150 g/L, about 10 to about 100 g/L, 20 to about 100 g/L or about 50 to about 100 g/L. In some embodiments, the suitable reaction conditions comprise a substrate compound loading of at least about 0.5 g/L, at least about 1 g/L, at least about 5 g/L, at least about 10 g/L, at least about 15 g/L, at least about 20 g/L, at least about 30 g/L, at least about 50 g/L, at least about 75 g/L, at least about 100 g/L, at least about 150 g/L or at least about 200 g/L, or even greater.

Suitable reaction conditions comprise a transaminase concentration of about 0.01 to about 50 g/L; about 0.05 to about 50 g/L; about 0.1 to about 40 g/L; about 1 to about 40 g/L; about 2 to about 40 g/L; about 5 to about 40 g/L; about 5 to about 30 g/L; about 0.1 to about 10 g/L; about 0.5 to about 10 g/L; about 1 to about 10 g/L; about 0.1 to about 5 g/L; about 0.5 to about 5 g/L; or about 0.1 to about 2 g/L. In some embodiments, the transaminase concentration at about 0.01, 0.05, 0.1, 0.2, 0.5, 1, 2, 5, 10, 15, 20, 25, 30, 35, 40, or 50 g/L.

During the course of the transamination reactions, the pH of the reaction mixture may change. The pH of the reaction mixture may be maintained at a desired pH or within a desired pH range. This may be done by the addition of an acid or a base, before and/or during the course of the reaction. Alternatively, the pH may be controlled by using a buffer. In some embodiments, the suitable reaction conditions comprise a solution pH comprise a pH from about 6 to about 12, pH from about 6 to about 10, pH from about 6 to about 8, pH from about 7 to about 10, pH from about 7 to about 9, or pH from about 7 to about 8. In some embodiments, the reaction conditions comprise a solution pH of about 6, 6.5, 7, 7.5, 8, 8.5, 9, 9.5, 10. 10.5, 11, 11.5 or 12.

Accordingly, in some embodiments, the reaction condition comprises a buffer. Suitable buffers to maintain desired pH ranges are known in the art and include, by way of example and not limitation, borate, carbonate, phosphate, triethanolamine buffer, and the like. In some embodiments, the buffer is borate. In some embodiments of the process, the suitable reaction conditions comprise a buffer solution of triethanolamine, where the triethanolamine concentration is from about 0.01 to about 0.4 M, 0.05 to about 0.4 M, 0.1 to about 0.3 M, or about 0.1 to about 0.2 M. In some embodiments, the reaction condition comprises a triethanolamine concentration of about 0.01, 0.02, 0.03, 0.04, 0.05, 0.07, 0.1, 0.12, 0.14, 0.16, 0.18, 0.2, 0.3, or 0.4 M. In some embodiments, the reaction conditions comprise water as a suitable solvent with no buffer present.

In the embodiments of the transamination process, a suitable temperature can be used for the reaction conditions, for example, taking into consideration the increase in reaction rate at higher temperatures, and the activity of the enzyme during the reaction time period. Accordingly, in some embodiments, the suitable reaction conditions comprise a temperature of about 10° C. to about 70° C., about 10° C. to about 65° C., about 15° C. to about 60° C., about 20° C. to about 60° C., about 20° C. to about 55° C., about 30° C. to about 55° C., or about 40° C. to about 50° C. In some embodiments, the suitable reaction conditions comprise a temperature of about 10° C., 15° C., 20° C., 25° C., 30° C., 35° C., 40° C., 45° C., 50° C., 55° C., 60° C., 65° C., or 70° C. In some embodiments, the temperature during the enzymatic reaction can be maintained at a temperature throughout the course of the reaction. In some embodiments, the temperature during the enzymatic reaction can be adjusted over a temperature profile during the course of the reaction.

The processes of the disclosure are generally carried out in a solvent. Suitable solvents include water, aqueous buffer solutions, organic solvents, polymeric solvents, and/or co-solvent systems, which generally comprise aqueous solvents, organic solvents and/or polymeric solvents. The aqueous solvent (water or aqueous co-solvent system) may be pH-buffered or unbuffered. In some embodiments, the transaminase processes are generally carried out in an aqueous co-solvent system comprising an organic solvent (e.g., ethanol, isopropanol (IPA), dimethyl sulfoxide (DMSO), ethyl acetate, butyl acetate, 1-octanol, heptane, octane, methyl t butyl ether (MTBE), toluene, and the like), ionic or polar solvents (e.g., 1-ethyl-4-methylimidazolium tetrafluoroborate, 1-butyl-3-methylimidazolium tetrafluoroborate, 1-butyl-3-methylimidazolium hexafluorophosphate, glycerol, polyethylene glycol, and the like). In some embodiments, the co-solvent can be a polar solvent, such as a polyol, dimethylsulfoxide, DMSO, or lower alcohol. The non-aqueous co-solvent component of an aqueous co-solvent system may be miscible with the aqueous component, providing a single liquid phase, or may be partly miscible or immiscible with the aqueous component, providing two liquid phases. Exemplary aqueous co-solvent systems can comprise water and one or more co-solvents selected from an organic solvent, polar solvent, and polyol solvent. In general, the co-solvent component of an aqueous co-solvent system is chosen such that it does not adversely inactivate the transaminase enzyme under the reaction conditions. Appropriate co-solvent systems can be readily identified by measuring the enzymatic activity of the specified transaminase enzyme with a defined substrate of interest in the candidate solvent system, utilizing an enzyme activity assay, such as those described herein.

In some embodiments of the process, the suitable reaction conditions comprise an aqueous co-solvent, where the co-solvent comprises a polyol solvent, particularly glycols. Examples of suitable polyol solvents include, by way of example and not limitation, polyethylene glycol, polyethylene glycol methyl ether, diethylene glycol dimethyl ether, triethylene glycol dimethyl ether, and polypropylene glycol. In some embodiments, the aqueous co-solvent comprises polyethylene glycol, which is available in different molecular weights. Particularly useful are lower molecular weight glycols, such as PEG200 to PEG600. Accordingly, in some embodiments, the aqueous co-solvent comprises PEG200 of about 1% to about 40% v/v; about 1% to about 40% v/v; about 2% to about 40% v/v; about 5% to about 40% v/v; 2% to about 30% v/v; 5% to about 30% v/v; 1 to about 20% v/v; about 2% to about 20% v/v; about 5% to about 20% v/v; about 1% to about 10% v/v; about 2% to about 10% v/v. In some embodiments, the suitable reaction conditions comprises an aqueous co-solvent comprising PEG200 at about 1%, 2%, 5%, 10%, 15%, 20%; 25%; 30%; 35%; 35% or about 40% v/v.

In embodiments of the process, the suitable reaction conditions comprise an aqueous co-solvent, where the co-solvent comprises DMSO at about 1% to about 80% (v/v), about 1 to about 70% (v/v), about 2% to about 60% (v/v), about 5% to about 40% (v/v), 10% to about 40% (v/v), 10% to about 30% (v/v), or about 10% to about 20% (v/v). In some embodiments of the process, the suitable reaction conditions comprise an aqueous co-solvent comprising DMSO at least about 1%, 5%, 10%, 15%, 20%, 25%, 30%, 35%, 40%, 45%, 50%, 55%, 60%, 65%, 70%, 75%, or 80% (v/v).

The quantities of reactants used in the transamination reaction will generally vary depending on the quantities of product desired, and concomitantly the amount of transaminase substrate employed. Those having ordinary skill in the art will readily understand how to vary these quantities to tailor them to the desired level of productivity and scale of production.

In some embodiments, the order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor, transaminase, and transaminase substrate may be added first to the solvent.

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a pre-chilled lyophilization chamber, followed by the application of a vacuum.

For improved mixing efficiency when an aqueous co-solvent system is used, the transaminase, and cofactor may be added and mixed into the aqueous phase first. The organic phase may then be added and mixed in, followed by addition of the transaminase substrate. Alternatively, the transaminase substrate may be premixed in the organic phase, prior to addition to the aqueous phase.

The transamination reaction is generally allowed to proceed until further conversion of ketone substrate to amine product does not change significantly with reaction time, e.g., less than 10% of substrate being converted, or less than 5% of substrate being converted. In some embodiments, the reaction is allowed to proceed until there is complete or near complete conversion of substrate ketone to product amine. Transformation of substrate to product can be monitored using known methods by detecting substrate and/or product. Suitable methods include gas chromatography, HPLC, and the like. Conversion yields of the chiral amine product generated in the reaction mixture are generally greater than about 50%, may also be greater than about 60%, may also be greater than about 70%, may also be greater than about 80%, may also be greater than 90%, and are often greater than about 97%.

Generally, the transamination reaction will proceed for a reaction time of about 120 h or less, about 96 h or less, about 72 h or less, about 48 h or less, about 36 h or less, about 24 h or less, about 18 h or less, or about 12 h or less, under suitable reaction conditions.

In some embodiments, the methods for preparing compounds of formula (VIII-1) and (VIII-aa) using a transaminase under suitable reaction conditions results in at least about 91%, 92%, 93%, 94%, 95%, 96%, 97%, 98%, 99% or greater conversion of ketone substrate, e.g., compound of formula (I) and (I-a), respectively, to the amine product compound, e.g., compound of formula (VIII-1) and (VIII-aa), respectively, in about 120 h or less, in about 96 h or less, in about 72 h or less, in about 48 h or less, in about 36 h or less, in about 24 h or less, or even less time.

In a further embodiment, the suitable reaction conditions comprise an initial substrate loading to the reaction solution which is then contacted with the transaminase. This reaction solution is the further supplemented with additional substrate of compound as a continuous addition over time at a rate of at least about 1 g/L/h, at least about 2 g/L/h, at least about 4 g/L/h, at least about 6 g/L/h, or higher. Thus, according to these suitable reaction conditions transaminase is added to a solution having an initial substrate loading of at least about 20 g/L, 30 g/L, or 40 g/L. This addition of transaminase is then followed by continuous addition of further substrate to the solution at a rate of about 2 g/L/h, 4 g/L/h, or 6 g/L/h until a much higher final substrate loading of at least about 30 g/L, 40 g/L, 50 g/L, 60 g/L, 70 g/L, 100 g/L, 150 g/L, 200 g/L or more, is reached. Accordingly, in some embodiments of the method, the suitable reaction conditions comprise addition of the transaminase to a solution having an initial substrate loading of at least about 20 g/L, 30 g/L, or 40 g/L followed by addition of further substrate to the solution at a rate of about 2 g/L/h, 4 g/L/h, or 6 g/L/h until a final substrate loading of at least about 30 g/L, 40 g/L, 50 g/L, 60 g/L, 70 g/L, 100 g/L or more, is reached. This substrate supplementation reaction condition allows for higher substrate loadings to be achieved while maintaining high rates of conversion of ketone substrate to amine product of at least about 91%, 92%, 93%, 94%, 95%, 96%, 97%, 98%, 99% or greater. In some embodiments of this method, the further substrate added is in a solution comprising isopropylamine or isopropylamine acetate at a concentration of at least about 0.5 M, at least about 1.0 M, at least about 2.5 M, at least about 5.0 M, at least about 7.5 M, at least about 10.0 M.

In some embodiments of the processes, the transamination reaction can comprise the following suitable reaction conditions: (a) substrate loading at about 5 g/L to 200 g/L; (b) about 0.1 to 50 g/L of transaminase; (c) about 0.1 to 4 M of isopropylamine (IPM); (d) about 0.1 to 10 g/L of pyridoxal phosphate (PLP) cofactor; (e) pH of about 6 to 10; and (f) temperature of about 30 to 60° C.

In some embodiments of the processes, the transamination reaction can comprise the following suitable reaction conditions: (a) substrate loading at about 10 to about 80 g/L; (b) about 0.5 to 25 g/L of transaminase; (c) about 0 to 10% v/v of PEG200; (d) about 0.1 to 2 M of isopropylamine (IPM); (e) about 0.1 to 1 g/L of pyridoxal phosphate (PLP) cofactor; (f) pH of about 8 to 10; (g) temperature of about 40 to 55° C., and (h) reaction times of 18 hr to 36 hr.

In some embodiments of the processes, the transamination reaction can comprise the following suitable reaction conditions: (a) substrate loading of about 25 to about 100 g/L; (b) about 0.5 to 10 g/L of transaminase; (c) about 0 to 10% v/v of PEG200; (d) about 0.1 to 2 M of isopropylamine (IPM); (e) about 0.1 to 1 g/L of pyridoxal phosphate (PLP) cofactor; (f) about 0.005 to about 0.1 M of borate (or comparable) buffer; (g) pH of about 8 to 10; and (h) temperature of about 40 to 55° C.

In some embodiments, additional reaction components or additional techniques carried out to supplement the reaction conditions. These can include taking measures to stabilize or prevent inactivation of the enzyme, reduce product inhibition, shift reaction equilibrium to product formation.

Accordingly, in some embodiments of the process for preparing an amine, such as a chiral amine, additional quantities of the amino acceptor can be added (up to saturation) and/or the amino acceptor (ketone) formed can be continuously removed from the reaction mixture. For example, a solvent bridge or a two phase co-solvent system can be used to move the amine product to an extraction solution, and thereby reduce inhibition by amine product and also shift the equilibrium towards product formation (see, e.g., Yun and Kim, 2008, Biosci. Biotechnol. Biochem. 72(11):3030-3033).

In some embodiments, where the choice of the amino donor results in a carbonyl by-product that has a vapor pressure higher than water (e.g., a low boiling co-product such as a volatile organic carbonyl compound), the carbonyl by-product can be removed by sparging the reaction solution with a non-reactive gas or by applying a vacuum to lower the reaction pressure and removing the carbonyl by-product present in the gas phase. A non-reactive gas is any gas that does not react with the reaction components. Various non-reactive gases include nitrogen and noble gases (e.g., inert gases). In some embodiments, the non-reactive gas is nitrogen gas. In some embodiments, the amino donor used in the process is isopropylamine (IPM), which forms the carbonyl by-product acetone upon transfer of the amino group to the amino group acceptor. The acetone can be removed by sparging with nitrogen gas or applying a vacuum to the reaction solution and removing the acetone from the gas phase by an acetone trap, such as a condenser or other cold trap. Alternatively, the acetone can be removed by reduction to isopropanol using a transaminase.

In some embodiments of the processes above where the carbonyl by-product is removed, the corresponding amino group donor can be added during the transamination reaction to replenish the amino group donor and/or maintain the pH of the reaction. Replenishing the amino group donor also shifts the equilibrium towards product formation, thereby increasing the conversion of substrate to product. Thus, in some embodiments wherein the amino group donor is isopropylamine and the acetone product is removed in situ, isopropylamine can be added to the solution to replenish the amino group donor lost during the acetone removal.

In further embodiments, any of the above described processes for the conversion of substrate compound to product compound can further comprise one or more steps selected from: extraction; isolation; purification; and crystallization of product compound. Methods, techniques, and protocols for extracting, isolating, purifying, and/or crystallizing the product amine from biocatalytic reaction mixtures produced by the above disclosed methods are known to the ordinary artisan and/or accessed through routine experimentation. Additionally, illustrative methods are provided in the Examples below.

After the transamination reaction, the obtained compound of formula (VIII) or (VIII-a), especially (VIII-1) or (VIII-aa), or a salt thereof, wherein Ra and Re are hydrogen, can then be used, in a further invention embodiment, for the manufacture of a corresponding compound of the formula (VIII) or (VIII-a), especially (VIII-1) and (VIII-aa), wherein Ra is hydrogen and Re is a nitrogen protecting group such as tert-butoxycarbonyl, e.g. by reacting the compound of the formula (VIII), especially (VIII-1) or (VIII-aa), wherein Ra is hydrogen, with an agent introducing such an amino protecting group, e.g. tert-butoxycarbonyl.

Alternatively or subsequently, the optionally amino protected analogue of the compound of the formula (VIII) or (VIII-a), especially (VIII-1) or (VIII-aa), wherein Ra is hydrogen and Re is hydrogen or a nitrogen protecting group, preferably hydrogen, can then be reacted with an activating reagent, e.g. thionyl chloride, in the presence of an alcohol, especially ethanol, to yield the corresponding compound of the formula (VIII) or (VIII-a), especially (VIII-1) or (VIII-aa), wherein Ra is $C_1$-$C_6$-alkyl, especially ethyl, e.g. at temperatures in the range from 50 to 80° C., e.g. 65 to 75° C.

Appropriate conditions and reagents that can be used for this sequence of steps directly or in an analogous way can, for example, be found in WO 2008/083967A, especially Examples 8 and 9 therein.

Reaction According to Schemes 7, 7-a, and 7-aa:

In another embodiment, the transformation comprises a process (forming an invention embodiment, alone or with the immediately or other preceding and following step or steps) which comprises reacting a compound of the formula (I), especially (I-a), wherein Ra is a carboxyl protecting group or especially $C_1$-$C_6$-alkyl, e.g. ethyl, with a sulfinamide compound of the formula (IX), Rb—S(=O)—$NH_2$, especially (IX-a), and/or the enantiomer thereof, or a salt thereof, respectively, wherein Rb is an organic moiety, preferably selected from the group consisting of $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—$(=O)_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl; especially a bulky moiety, such as a tert-alkyl, e.g. tert-butyl, or an aryl, e.g. p-tolyl, moiety; to give a sulfinimide compound of the formula (X), especially of the formula (X-a), wherein Rb is as just defined for a compound of the formula (IX) and Ra is as just defined.

This reaction preferably takes place e.g. under the conditions of the Ellman reaction (cf. e.g. F. Chemla, F. Ferreira, J. Org. Chem. 2004, 69, 8244), especially in an appropriate solvent or solvent mixture, e.g. a halogenated hydrocarbon, such as dichloromethane, or an ether, such as tetrahydrofuran, preferably in the presence of a weekly active acidic catalyst, such as pyridinium p-toluenesulfonate, Ti(OiPr)$_4$ or Ti(OEt)$_4$ as Lewis acid (cf. e.g. T. Boultwood, D. P. Affron, A. D. Trowbridge, J. A. Bull, *J. Org. Chem.* 2013, 78, 6632), for example at a temperature in the range from 0 to 100° C., e.g. from 15 to 70° C.

The reaction is preferably followed by a method (also, alone or with the immediately or other preceding and following step or steps, forming an invention embodiment) comprising reduction of the compound of the formula (X), especially (X-a), to give a sulfinamide compound of the formula (XI), or a salt thereof, especially of the formula (XI-a), more preferably of formula (XI-aa) or a salt thereof, wherein Rb and Ra are as defined for a compound of the formula (X) above, in the presence of a reducing agent.

As a reducing agent, preferably hydrogen in the presence of a catalyst such as Ru, e.g. under transfer catalysis conditions with e.g. isopropanol as solvent at a preferred temperature of 40-90° C., a complex hydride, such as an alkali metal borohydride, e.g. sodium borohydride (if desired in the presence of an acid, e.g. boric acid, toluene sulfonic acid or benzoic acid), an alkali metal aluminium hydride, such as lithium aluminium hydride is used.

The reaction preferably takes place in a customary solvent, e.g. an ether, such as diethylether or tetrahydrofuran, and at appropriate temperatures, e.g. in the range from −78° C. to 40° C., e.g. from −78° C. to 20° C.

Alternatively, diisobutylaluminium hydride, borane, L-Selectride (lithium tri-sec.butyl(hydrido)borate-(1-)) or LiBEt$_3$H (lithiumtriethylborohydride) may be used in an appropriate solvent, such as an ether, e.g. tetrahydrofurane, at low temperatures, e.g. in the range from −100 to 0° C., e.g. at −78° C.

The compound of the formula (XI), especially (XI-a), can then be further reacted to result in a compound of the formula (VIII), especially (VIII-a), or a salt thereof: In this reaction, the sulfinamide compound of the formula (XI), or a salt thereof, especially of the formula (XI-a), or a salt thereof, wherein Rb is as defined for a compound of the formula (X) and Ra is selected from hydrogen, a carboxyl protecting group, and C$_1$-C$_6$-alkyl, preferably ethyl or hydrogen, more preferably ethyl, is hydrolyzed in the presence of an acid.

A suitable acid is an organic, such as acetic acid or citric acid, or preferably an inorganic acid, e.g. a hydrohalic acid, such as hydrochloric acid, sulfuric acid, phosphoric acid or a mixture of two or more thereof, preferably in aqueous solution in particular comprising a further organic solvent, such as an alcohol, e.g. methanol, ethanol or isopropanol, or an ether, e.g. 1,4-dioxane, tetrahydrofurane, tert-butyl methyl ether or diethylether, or mixtures of two or more of these solvents, preferably at temperatures in the range e.g. from 0 to 60° C., e.g. from 20 to 25° C., or up to reflux.

This preferably results in a salt of a compound of the formula (VIII), especially (VIII-a), with the acid(s) used.

If desired, a salt of a compound of the formula (VIII), especially (VIII-a), can then be converted into the free compound of the formula (VIII), especially (VIII-a), using customary processes, or into a different salt, e.g. using ion exchange chromatography, neutralization with a base, e.g. an alkali metal hydroxide, or the like.

Compound (XI), especially compound (XI-a), can alternatively be transformed into compound (VIII), especially compound (VIII-a), wherein Ra is C$_1$-C$_6$-alkyl, preferably ethyl, in the absence of water, e.g. by use of an anhydrous inorganic acid, e.g. a hydrohalic acid, such as hydrochloric acid, either used as gas or generated in situ using a suitable reagent, in the presence of an alcohol of the formula Ra—OH wherein Ra is selected from a carboxyl protecting group, and C$_1$-C$_6$-alkyl, especially ethyl, respectively.

Suitable reagents for generation of inorganic acids in situ are for example selected from thionyl chloride, thionyl bromide, PCl$_3$, PCl$_5$, oxalyl chloride, Me$_2$C=C(Cl)NMe$_2$, PhCOCl, PBr$_3$, PBr$_5$, Ph$_3$PBr$_2$, oxalyl bromide or Me$_2$C=C(Br)NMe$_2$.

The reaction preferably takes place in a customary solvent, such as an alcohol, e.g. methanol or ethanol, and at appropriate temperatures, e.g. in the range from 0 to 50° C., e.g. from 10 to 30° C.

An example for appropriate reaction conditions can be found in *Org. Lett.* 2012, 14, 2062-2065 (deprotection of sulfinyl amine and concomitant esterification; thionyl chloride in methanol).

The sulfinamide compound of the formula (IX) Rb—S(=O)—NH$_2$, especially (IX-a), wherein Rb is tert-butyl, is well known in the art and commercially available in both stereoisomeric forms (see e.g. Sigma-Aldrich, catalogue no. 497401, CAS no. 196929-78-9 for the (R)-enantiomer; catalogue no. 513210, CAS no. 343338-28-3 for the (S)-enantiomer). Compounds with other meanings of Rb (and also the known one for Rb=tert-butyl) can be obtained, for example, by (for the manufacture of the compound of formula (IX-a) preferably asymmetric) mono-oxidation of a disulfide of the formula (XII)

(XII)

wherein Rb is as defined above for a compound of the formula (IX), especially (IX-a), followed by amidation of the resulting sulfinyl sulfide compound of the formula (XIII),

(XIII)

especially of the formula (XIII-a),

(XIII-a)

and/or the enantiomer thereof,
wherein Rb is as just defined, with a metal amide and subsequent S$_N$2 attack to yield a thiol of the formula Ra—SH and the compound of the formula (IX), especially (IX-a).

For synthesis of the compound of the formula (IX-a) via (XIII-a), the asymmetric mono-oxidation is preferably conducted in the presence of a chiral ligand, e.g. a benzocyclopentanolimine named (1S,2R)-1-[(2-hydroxy-3,5-di-tert-butyl-benzylidene)-amino]-indan-2-ol of the formula

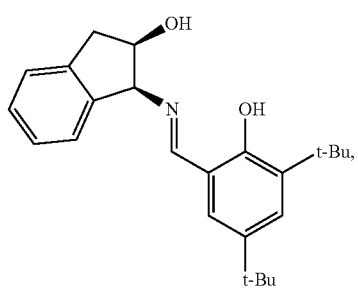 [SMILES: CC(C)(C)c1cc(/C=N/[C@H]2c3ccccc3C[C@H]2O)c(O)c(C(C)(C)C)c1]

or other ligands selected from those of the following formula:

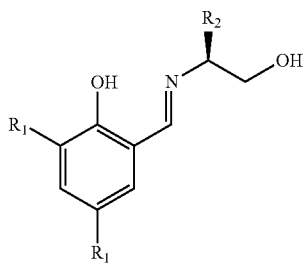

wherein $R_1$ is hydrogen, tert-butyl or methoxy; and $R_2$ is tert-butyl, isopropyl, benzyl or phenyl.

As example, the compound (with $R_1=R_2=$tert-butyl) with the name N-(3,5-di-tert-butylsalicylmethylene)-tert-leucinol may be mentioned.

The mono-oxidation is preferably achieved with a peroxide, especially hydrogen peroxide, in an appropriate solvent, such as a ketone, e.g. acetone, e.g. under conditions described by Ellman et al. (cf. D. J. Weix, J. A. Ellman, Org. Lett. 2003, 5, 1317) in the presence of a vanadyl complex, especially vanadyl-bis-acetylacetonate, in an appropriate solvent or solvent mixture, e.g. a ketone, such as acetone, preferably at lower temperatures e.g. in the range from −20 to 20° C., e.g. from −5 to 5° C.

The resulting sulfinylsulfide compound of the formula (XIII), especially (XIII-a), is then reacted under $S_N2$ substitution with a metal amide, especially an alkaline metal amide, such as lithium amide, in an appropriate solvent or solvent mixture, e.g. in $NH_3$ in a cyclic ether, such as tetrahydrofuran, preferably at low temperatures, e.g. in the range from −100 to 0° C., e.g. from −80 to −50° C., resulting in the sulfinamide of the formula (IX), especially (IX-a).

Reaction According to Schemes 8, 8-a, and 8-aa:

In another embodiment, the transformation comprises a process (forming an invention embodiment, alone or with the immediately or other preceding and following step or steps) which comprises reacting a compound of the formula (I), especially (I-a), wherein Ra is hydrogen, or a salt thereof, with hydroxylamine or a salt thereof, yielding a compound of the formula (XVII), especially of formula (XVII-a), wherein Ra is hydrogen, if starting from a compound of the formula (I), especially (I-a), wherein Ra is hydrogen, or a salt thereof.

The reaction preferably takes place with a hydroxylamine salt, e.g. hydroxylamine hydrochloride, in an appropriate solvent or solvent mixture, e.g. in an alcohol, such as ethanol, in the presence of a base, e.g. pyridine, at preferred temperatures in the range from 0 to 100° C., e.g. in the range from 20 to 90° C.

The reaction is preferably followed by a method (also forming a separate invention embodiment) comprising cyclization of the compound of the formula (XVII), especially of formula (XVII-a), to give a cyclic O-acyl oxime compound of formula (XVIII), especially of the formula (XVIII-a).

The cyclization preferably takes place in the presence of an acid such as an organic acid, e.g. a sulfonic acid, such as p-toluene sulfonic acid, present in stoichiometric or catalytic amounts, preferably in catalytic amounts, e.g. 0.05 to 0.5 equiv., in an appropriate solvent or solvent mixture, e.g. in toluene, e.g. at elevated temperatures from 50° C. to the reflux temperature of the reaction mixture, such as from 70 to 90° C.

The compound of the formula (XVIII), especially (XVIII-a), can then be further converted (in a further method according to the invention, either as single step or with the preceding reactions above) by a process comprising the reduction of the cyclic O-acyl oxime to provide a compound of formula (VIII), especially of the formula (VIII-a), or a salt thereof, respectively, wherein Ra is hydrogen or a carboxyl protecting group or especially $C_1$-$C_6$-alkyl, more especially ethyl. Reduction of the cyclic oxime derivatives to the corresponding amines is generally achieved using metal-catalyzed hydrogenation reactions (e.g. Pd or Rh on solid supports like activated carbon or aluminum oxide or Raney-Ni) or complex hydrides (e.g. sodium borohydride or lithium aluminum hydride).

The alternative direct reduction of the free oxime of formula (XVII), preferably of formula (XVII-a) to the corresponding amines of formula (VIII) can be generally achieved using metal-catalyzed hydrogenation reactions (e.g. Pd or Rh on solid supports like activated carbon or aluminum oxide or Raney-Ni) or complex hydrides (e.g. sodium borohydride or lithium aluminum hydride).

The reduction can be achieved using hydrogen in the presence of a transition metal catalyst, such as RhCl(PPh3)3, [Ru(S)-BINAP(p-cymene)Cl]Cl, Pd/C or Pt/C (if desired in the presence of an acid, e.g. benzoic acid), e.g. under elevated pressure up to 30 bar, in an appropriate solvent or solvent mixture, e.g. THF, methanol or THF/water, e.g. at temperatures from 20° C. to 80° C., such as from 25 to 70° C.; or by reduction in a two-step approach, consisting of (1) reduction of the C—N double bond using a hydrogenating agent, e.g. sodium borohydride, followed by (2) reduction of the N—O bond using hydrogen and a catalyst, e.g. a noble metal catalyst with or without carrier, such as Pt or Pd or Pd or Pt on charcoal, e.g. in an appropriate solvent, such as an alcohol, e.g. methanol or ethanol, at temperatures e.g. in the range from 0° C. to reflux temperature, e.g. from 20 to 50° C.

Reaction According to Schemes 9, 9-a, and 9-aa:

In another embodiment, the transformation comprises a process (forming an invention embodiment, alone or with the immediately or other preceding and following step or steps) which comprises reacting a compound of the formula (I), especially (I-a), wherein Ra is hydrogen, or a salt thereof, with ammonia or an ammonium salt, yielding a compound of the formula (XIX), especially (XIX-a). The compound may also be present as a mixture of double bond isomers in any relative ratio.

The reaction preferably takes place with an ammonium salt, e.g. ammonium acetate, in an appropriate solvent or solvent mixture, e.g. in an organic acid, such as acetic acid, at preferred temperatures in the range from 50 to 150° C., e.g. in the range from 100 to 140° C.

The reaction is preferably followed by a method comprising reduction of the compound of the formula (XIX), especially (XIX-a), to give a cyclic lactam compound of the formula (XX), especially of the formula (XX-a).

The reduction preferably takes place using hydrogen in the presence of a transition metal catalyst, such as Pd/C, e.g. under elevated pressure up to 10 bar, e.g. in the range 3-8 bar, in an appropriate solvent or solvent mixture, e.g. methanol, e.g. at temperatures from 20° C. to 150° C., such as from 80 to 140° C. Other possible reduction methods comprise the reduction of the C—N double bond using a hydrogenating agent other than hydrogen, e.g. a hydride salt, such as lithium aluminum hydride. (see e.g. (Chem. Ber. 1971, 104, 2134-2142).

Compound (XX), especially compound (XX-a), can then be converted to compound (VIII), especially to compound (VIII-a), as described, for example, in WO 2008/083967A, especially Examples 7 and 13 therein. Compound (VIII) with Ra=H can be obtained by treatment of compound (XX) under aqueous acidic conditions, e.g. by heating compound (XX) in a mixture of acetic acid and concentrated hydrochloric acid at reflux. Compound (VIII) with Ra=$C_1$-$C_6$-alkyl can be obtained by treatment of compound (XX) with an inorganic acid (e.g. sulfuric acid or hydrochloric acid) or an organic acid (e.g. p-toluenesulfonic acid) in the presence of an alcohol, potentially used as reaction solvent, at elevated temperature (e.g. 80-120° C.).

Reaction According to Schemes 10, 10-a, and 10-aa:

In another embodiment, the transformation comprises a process (forming an invention embodiment, alone or with the immediately or other preceding and following step or steps) which comprises reacting a compound of the formula (I), especially (I-a), wherein Ra is hydrogen or a carboxyl protecting group or especially $C_1$-$C_6$-alkyl, more especially ethyl, with an O-substituted hydroxylamine selected from

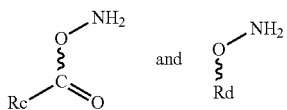

or in each case a salt thereof, wherein Rc and Rd are independently selected from $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl or heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from halo, $C_1$-$C_7$-alkyl, halo-$C_1$-$C_7$-alkyl, and $C_1$-$C_7$-alkoxy, halo-$C_1$-$C_7$-alkoxy, and $C_1$-$C_7$-alkoxy-$C_1$-$C_7$-alkyl; preferably an O—($C_1$-$C_6$-alkyl-acyl)-hydroxylamine, an O—($C_6$-$C_{10}$-aryl-$C_1$-$C_6$-alkyl)-hydroxylamine or an O—$C_1$-$C_6$-alkyl-hydroxylamine, or in each case a salt thereof, to yield a compound of the formula (XVII*), especially (XVII*-a), or a salt thereof, respectively.

The reaction with the O-substituted hydroxylamine preferably takes place in the presence of an acid such as an organic acid, e.g. a sulfonic acid, such as p-toluene sulfonic acid, present in stoichiometric or catalytic amounts, preferably in catalytic amounts, e.g. 0.05 to 0.5 equiv., in an appropriate solvent or solvent mixture, e.g. in toluene, e.g. at elevated temperatures from 50° C. to the reflux temperature of the reaction mixture, such as from 70 to 90° C.

The substituents Rc and Rd are preferably selected in a way to avoid cyclization of the compound of formula (XVII***) to a compound of the formula (XVIII) (see SCHEME 8), and/or—if desired—can be removed to yield the corresponding compound wherein A is hydroxyl, i.e. a compound of formula (XVII).

Alternatively, to avoid cyclization, the compound of formula (XVII***) Ra can have one of the meanings mentioned other than hydrogen.

The compound of the formula (XVII*), especially (XVII*-a) can then be further converted (in a further method according to the invention, either as single step or with the preceding reactions above) by a process comprising the reduction of the O-substituted oxime group to provide a compound of formula (VIII), especially of the formula (VIII-a), or a salt thereof, respectively, wherein Ra is hydrogen or a carboxyl protecting group or especially $C_1$-$C_6$-alkyl, more especially ethyl. Reduction of the oximes derivatives to the corresponding amines is generally achieved using metal-catalyzed hydrogenation reactions (e.g. Pd or Rh on solid supports like activated carbon or aluminum oxide or Raney-Ni) or complex hydrides (e.g. sodium borohydride or lithium aluminum hydride).

The reduction can be achieved using hydrogen in the presence of a transition metal catalyst, such as RhCl(PPh3)3, [Ru(S)-BINAP(p-cymene)Cl]Cl, Pd/C or Pt/C (if desired in the presence of an acid, e.g. benzoic acid), e.g. under elevated pressure up to 30 bar, in an appropriate solvent or solvent mixture, e.g. THF, methanol or THF/water, e.g. at temperatures from 20° C. to 80° C., such as from 25 to 70° C.; or by reduction in a two-step approach, consisting of (1) reduction of the C—N double bond using a hydrogenating agent, e.g. sodium borohydride, followed by (2) reduction of the N—O bond using hydrogen and a catalyst, e.g. a noble metal catalyst with or without carrier, such as Pt or Pd or Pd or Pt on charcoal, e.g. in an appropriate solvent, such as an alcohol, e.g. methanol or ethanol, at temperatures e.g. in the range from 0° C. to reflux temperature, e.g. from 20 to 50° C.

Follow on Reaction of a Compound of Formula (VIII) to Produce a NEP Inhibitor

In another embodiment of the invention, the intermediates, in particular the novel compounds of formula (XV), in particular of formula (I) or (II), and of formula (XVI), in particular of formula (X), (XVII), (XVII*), (XVII**), (XVIII), and (IX), or the preferred stereoisomer thereof, as depicted above, and the products of the process of the present invention can be used in the synthesis of NEP inhibitors or salts or pro-drugs thereof, in particular they can be used in the synthesis of NEP inhibitors comprising a γ-amino-δ-biphenyl-α-methylalkanoic acid, or acid ester, backbone. NEP inhibitors or pro-drugs thereof comprising a γ-amino-δ-biphenyl-α-methylalkanoic acid, or acid ester, backbone include, for example, the NEP inhibitor pro-drug N-(3-carboxy-1-oxopropyl)-(4S)-(p-phenylphenylmethyl)-4-amino-(2R)-methylbutanoic acid ethyl ester and the corresponding NEP inhibitor N-(3-carboxy-1-oxopropyl)-(4S)-(p-phenylphenylmethyl)-4-amino-(2R)-methylbutanoic acid.

The term "NEP inhibitor" describes a compound which inhibits the activity of the enzyme neutral endopeptidase (NEP, EC 3.4.24.11).

Compounds of formula (VIII) or salts thereof, preferably of formula (VIII-a), or salts thereof, more preferably of formula (VIII-aa), or salts thereof, as described herein above can be further reacted to a NEP inhibitor or salts or prodrugs thereof, in particular to the NEP inhibitor prodrug N-(3- carboxy-1-oxopropyl)-(4S)-(p-phenylphenyl-methyl)-4-amino-(2R)-methylbutanoic acid ethyl ester or the corresponding NEP inhibitor N-(3-carboxy-1-oxopropyl)-(4S)-(p-phenylphenylmethyl)-4-amino-(2R)-methylbutanoic acid as described by Ksander et al. in *J. Med. Chem.* 1995, 38, 1689-1700, or as described in WO 2008/31567.

In a preferred embodiment of the invention a compound according to formula (VIII), preferably of formula (VIII-a), more preferably of formula (VIII-aa), or salt thereof, is further reacted to obtain the NEP inhibitor pro-drug of formula (10)

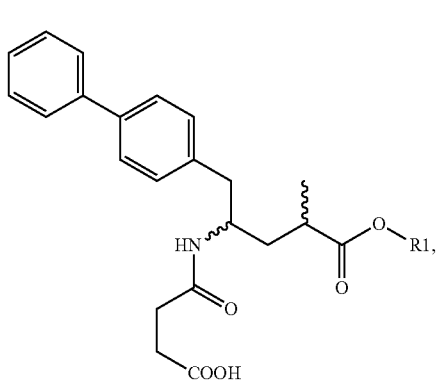

preferably of formula (10-a)

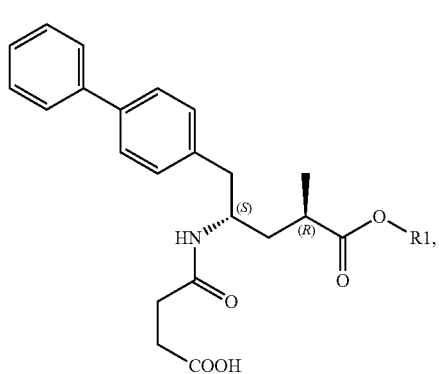

wherein R1 is hydrogen or $C_1$-$C_6$-alkyl, preferably ethyl, by reaction with succinic acid or a derivative thereof, preferably succinic acid anhydride.

Deprotection of the nitrogen functionality, i.e. removal of the Boc group,—if necessary—re-introduction of the ethyl ester group, and subsequent coupling with succinic anhydride delivers the desired NEP inhibitor prodrug compound. Optionally, the ester can be saponified to the free acid providing the NEP inhibitor drug compound.

In one embodiment, the compound of formula (10-a) is N-(3-carboxy-1-oxopropyl)-(4S)-(p-phenylphenylmethyl)-4-amino-(2R)-methylbutanoic acid ethyl ester (known in the art as AHU377) or a salt thereof.

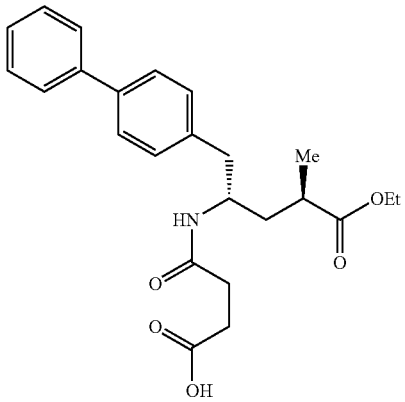 [SMILES: CCOC(=O)[C@H](C)C[C@@H](Cc1ccc(-c2ccccc2)cc1)NC(=O)CCC(=O)O]

The NEP inhibitor pro-drug N-(3-carboxy-1-oxopropyl)-(4S)-(p-phenylphenylmethyl)-4-amino-(2R)-methylbutanoic acid ethyl ester optionally is further reacted to obtain the NEP inhibitor N-(3-carboxy-1-oxopropyl)-(4S)-(p-phenylphenylmethyl)-4-amino-(2R)-methylbutanoic acid.

For example, this conversion can be performed using the Boc protected amino acid e.g. according to scheme Z below where the Boc corresponds to R' and R" is H in formula (8-a) and R1 is H and the aminoethyl ester (upper right formula in scheme Z below with R'=H, R"=H, R1=Et). If R1 is ethyl, the reaction works identically. If R1 is a different alkyl group, then transesterification or saponification is needed before.

Scheme Z

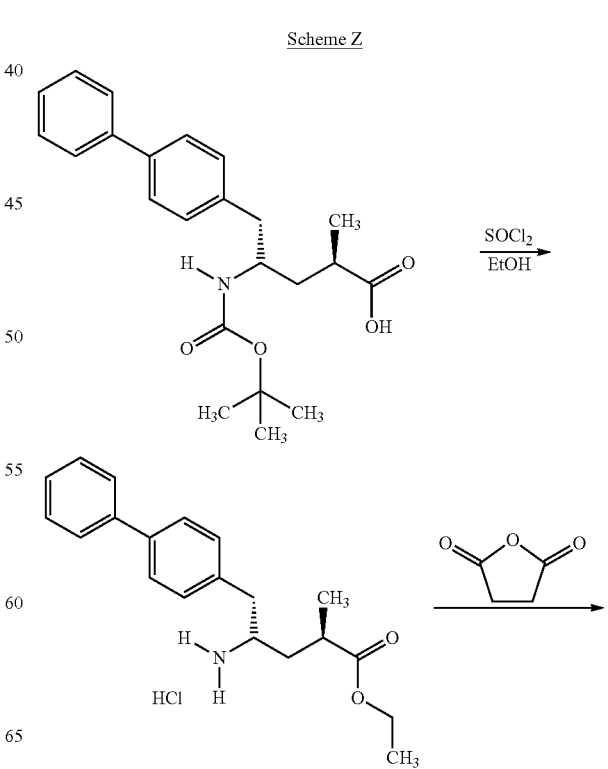

65

-continued

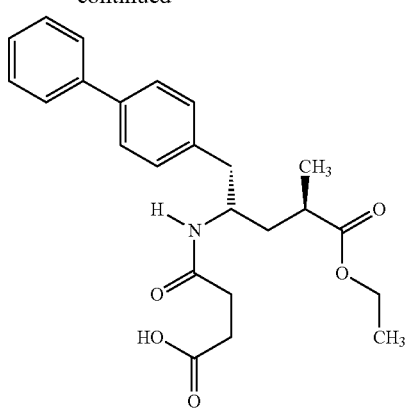

If further conversion to the respective salts is required, this can be achieved by carrying out the following additional steps:

66

-continued

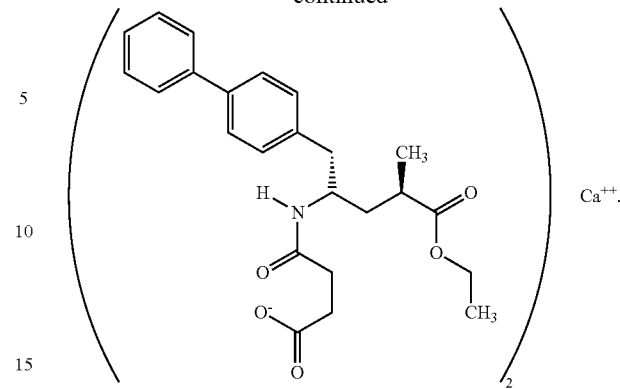

Conditions for these reactions are known to the person skilled in the art (see e.g. WO 2008/031567).

Compounds

The invention also relates to novel compounds mentioned above and below. From these compounds, those mentioned specifically in the Examples are most preferred.

EXAMPLES

The following examples serve to illustrate the invention without limiting the scope thereof, while they on the other hand represent preferred embodiments of the reaction steps, inter-mediates and/or the process of the present invention.

Abbreviations

Aq., aq. Aqueous
Ac acetyl
Bu butyl
CDI N,N-carbonyldiimidazole
Et ethyl
h hour(s)
Me methyl
min minute(s)
NMR nuclear magnetic resonance
Pd/C palladium on carbon
Ph phenyl
RT room temperature In quoting NMR data, the following abbreviations are used: s, singlet; d, doublet; t, triplet; q, quartet; quint., quintet; m, multiplet.

Note that in the Examples the numbers of compounds, such as 1 or 2, are different and separate from the compounds represented by numbers in parenthesis above and in the claims, such as (1) or (2), just to clarify paradigmatically.

Overview I

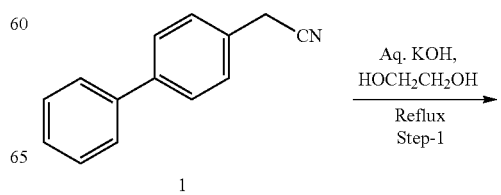

-continued

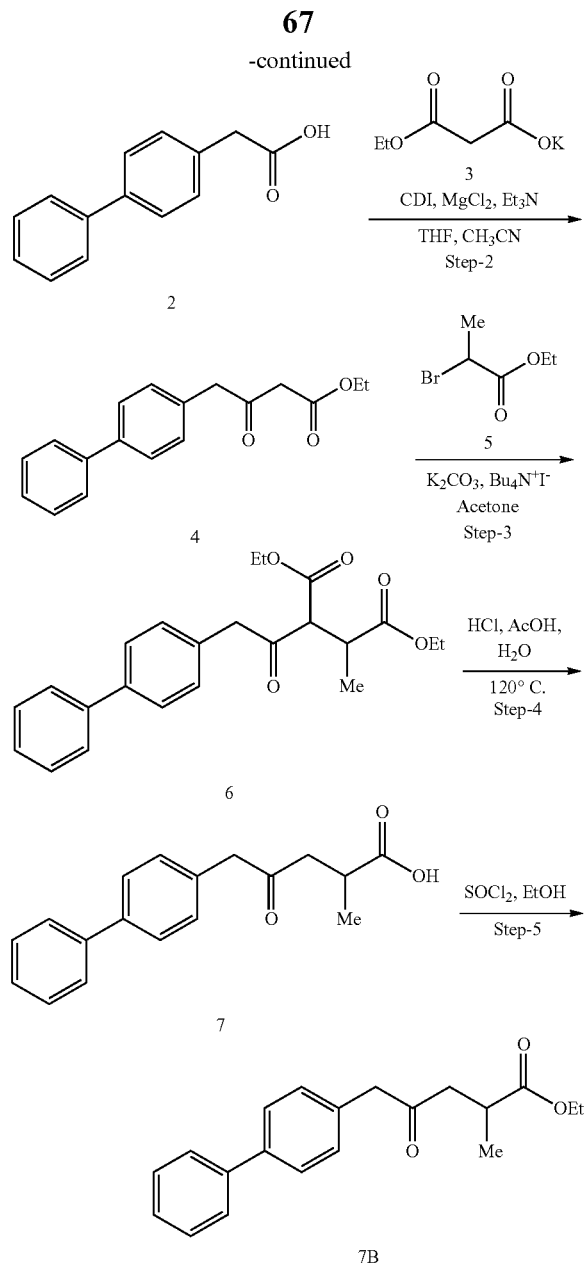

Example 1: Step-1—Manufacture of 2-([1,1'-biphenyl]-4-yl)acetic Acid 2

To a solution of 2-([1,1'-biphenyl]-4-yl) acetonitrile 1 (e.g. Sigma-Aldrich, catalogue no. 133612, CAS no. 31603-77-7) (100 g, 517.46 mmol) in ethylene glycol (1000 mL), a solution of potassium hydroxide (590 g, 10515 mmol) in water (1000 mL) was added and the resulting mixture was heated to 120° C. and stirred for 16 h. The reaction mixture was cooled to 0° C. and acidified with concentrated HCl with stirring. The solid separated out was collected by filtration, washed with water and dried. The solid was dissolved in ethyl acetate and the ethyl acetate layer was washed with water, dried over sodium sulfate and concentrated under reduced pressure to get white solid. The solid was taken in petroleum ether, stirred for ~30 min, filtered and dried to get 2-([1,1'-biphenyl]-4-yl)acetic acid 2 as white solid. (107.2 g, 97.6%).

$^1$H-NMR (400 MHz, DMSO-d6): δ 12.41 (br. s, 1H), 7.59-7.66 (m, 4H), 7.44-7.47 (m, 2H); 7.34-7.37 (m, 3H), 3.61 (s, 2H) ppm; MS (MM-ES, APCI): negative mode 257.0 [M+HCO$_2$]$^-$.

Example 2: Step-2—Manufacture of ethyl 4-([1,1'-biphenyl]-4-yl)-3-oxobutanoate 4

To a solution of 2-([1,1'-biphenyl]-4-yl)acetic acid 2 (107 g, 504.12 mmol) in tetrahydrofuran (1000 mL) at 0° C. under N$_2$, N,N-carbonyldiimidazole (64.1 g, 395.3 mmol) was added portion wise and the resulting mixture was stirred at the same temperature for 15 min and then warmed to room temperature and stirred for 16 h. In a separate flask, to a stirred suspension of ethyl potassium malonate 3 (138 g 810.76 mmol) in acetonitrile (1000 mL) at 0° C. under N$_2$, magnesium chloride (96 g, 1008.3 mmol) was added followed by triethylamine (160 mL, 1147.9 mmol) and stirred at the same temperature for 3 h and at room temperature for 2 h. The activated acid mixture was then added dropwise to the stirred magnesium salt suspension and the resulting mixture was then stirred at room temperature for 24 h. A solution of sodium hydrogen sulphate (600 g) in H$_2$O (2 L) was then added to the reaction mixture and stirred for 5 min. It was further diluted with water and extracted with ethyl acetate. The combined organic layer was washed with water, aq. 5% NaOH solution, finally with brine, dried over sodium sulfate and concentrated under reduced pressure to get brown solid. The crude product obtained was purified by column chromatography (silica gel, 230-400 mesh; eluent: 0-20% ethyl acetate in petroleum ether). The solid obtained was slurried in a mixture of petroleum ether and diethyl ether (8:2), filtered, washed with petroleum and dried to obtain ethyl 4-([1,1'-biphenyl]-4-yl)-3-oxobutanoate 4 as off-white solid (128 g, 89.9%).

$^1$H-NMR (400 MHz, DMSO-d6): δ 7.59-7.66 (m, 4H), 7.42-7.47 (m, 2H), 7.32-7.37 (m, 1H), 7.25-7.28 (m, 2H), 4.10 (q, 2H), 3.91 (s, 2H), 3.68 (s, 2H), 1.18 (t, 3H) ppm.

Example 3: Step-3—Manufacture of diethyl 2-(2-([1,1'-biphenyl]-4-yl)acetyl)-3-methylsuccinate 6

To a stirred mixture of ethyl 4-([1,1'-biphenyl]-4-yl)-3-oxobutanoate 4 (64 g, 226.68 mmol), potassium carbonate (63 g, 455.83 mmol) and tetrabutylammonium iodide (17 g, 46.02 mmol) in acetone (1800 mL) at 0° C. under N$_2$, ethyl 2-bromopropionate 5 (26.5 mL, 204.06 mmol) was added drop wise and the resulting mixture was stirred at room temperature for 48 h. The reaction mixture was concentrated under reduced pressure to remove acetone and the residue was diluted with water and extracted with ethyl acetate. The combined organic layer was washed with water and brine, dried over anhydrous Na$_2$SO$_4$ and concentrated under reduced pressure to get the crude product 6 as wine red color viscous oil (159 g).

The crude product obtained was taken for the next step without further purification.

Example 4: Step-4—Manufacture of 5-([1,1'-biphenyl]-4-yl)-2-methyl-4-oxopentanoic Acid 7

A mixture of diethyl 2-(2-([1,1'-biphenyl]-4-yl)acetyl)-3-methylsuccinate 6 (159 g, 415.73 mmol), acetic acid (1500 mL), concentrated hydrochloric acid (1500 mL) and water (750 mL) was heated to 120° C. and stirred for 6 h.

The reaction mixture was concentrated under reduced pressure and the residue was diluted with water and extracted with ethyl acetate. The combined organic layer was washed with water and brine, dried over anhydrous Na₂SO₄ and concentrated under reduced pressure to obtain the crude product.

The crude product obtained was purified by column chromatography (two times) (silica gel, 230-400 mesh; eluent: 0-35% ethyl acetate in petroleum ether) and then the solid obtained was washed with petroleum ether and dried to get 5-([1,1'-biphenyl]-4-yl)-2-methyl-4-oxopentanoic acid 7 as white solid (55.3 g, 47.1%).

¹H-NMR (400 MHz, DMSO-d6): δ 12.13 (br. s, 1H), 7.61-7.67 (m, 4H), 7.45-7.48 (m, 2H), 7.34-7.38 (m, 1H), 7.27-7.29 (m, 2H), 3.82 (s, 2H), 2.88 (dd, 1H), 2.72 (ddq, 1H), 2.57 (dd, 1H), 1.06 (d, 3H) ppm; MS (MM-ES, APCI): negative mode 281.0 [M−H]⁻.

Example 5: Step-5—Manufacture of 5-([1,1'-biphenyl]-4-yl)-2-methyl-4-oxopentanoic Acid ethyl ester 7B To a solution of 5-([1,1'-biphenyl]-4-yl)-2-methyl-4-oxopentanoic acid 7 (55 g, 194.8 mmol) in ethanol (500 mL), thionyl chloride (43 mL, 589.5 mmol) was added and the resulting mixture was stirred at 80° C. for 3 h.

The reaction mixture was concentrated under reduced pressure to remove the volatiles and the residue was diluted with water and extracted with ethyl acetate. The combined organic layer was washed with water and brine, dried over anhydrous Na₂SO₄ and concentrated under reduced pressure to obtain the crude product.

The crude product obtained was mixed with the product obtained in another batch (~14.1 g) and purified by column chromatography (twice) (silica gel, 230-400 mesh; eluent: 0-3% ethyl acetate in petroleum ether). The product 7B was collected in two fractions as pale yellow viscous oils. (Both the fractions were dissolved in dichloromethane and concentrated under reduced pressure at 45° C.). Fraction-1: 50.5 g (>99% pure); Fraction-2: 17 g (~95% pure).

¹H-NMR (400 MHz, DMSO-d6): δ 7.56-7.61 (m, 4H), 7.43-7.47 (m, 2H), 7.34-7.38 (m, 1H), 7.27-7.30 (m, 2H), 4.13 (q, 2H), 3.77 (s, 2H), 2.93-3.01 (m, 2H), 2.50-2.57 (ddq, 1H), 1.25 (t, 3H), 1.17 (d, 3H) ppm; ¹³C-NMR (100 MHz, DMSO-d6): δ 206.3, 175.7, 140.7, 140.0, 133.0, 129.9, 128.8, 127.5, 127.3, 127.1, 60.6, 49.8, 45.1, 34.9, 17.1, 14.2 ppm; MS (MM-ES, APCI): positive mode 311.0 [M+H]⁺; IR: 3029, 2977, 2361, 1717, 1603, 1519, 1486, 1458, 1403, 1375, 1338, 1262, 1184, 1041, 925, 837, 760, 737, 697 cm⁻¹.

Overview II:

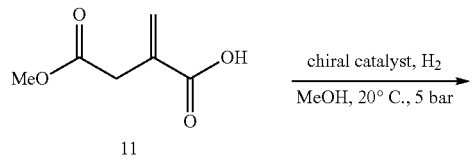

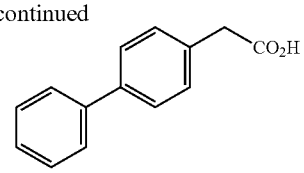

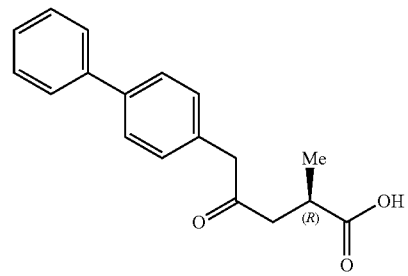

Example 6: Synthesis of (R)-4-methoxy-2-methyl-4-oxobutanoic acid 12

Compound 12 is commercially available and can be prepared according to literature procedures (e.g. *Adv. Synth. Catal.* 2003, 345, 308-322; *Adv. Synth. Catal.* 2004, 346, 1263-1266; *Chem. Eur. J.* 2009, 15, 3983-4010; *Chem. Eur. J.* 2012, 18, 14267-14271) from 4-methoxy-2-methylene-4-oxobutanoic acid 11.

Example 7: Synthesis of (R)-5-([1,1'-biphenyl]-4-yl)-2-methyl-4-oxopentanoic acid 7

A solution of 4-biphenylacetic acid 2 (10.0 g, 45.70 mmol, 1.00 equiv.) in THF (36 mL) at 35° C. is treated with a 20% solution of ⁱPrMgCl·LiCl in THF (100 g, 137.7 mmol, 3.00 equiv.) over 20 min. After stirring for 1.5 h, the solution is cooled to 0° C. In a separate flask, a solution of compound 12 (8.45 g, 54.83 mmol, 1.20 equiv.) in THF (48 mL) at −15° C. is treated with a 20% solution of ⁱPrMgCl·LiCl in THF (41.8 g, 57.56 mmol, 1.25 equiv.) over 20 min. After stirring at −15° C. for 10 min, the solution is warmed to room temperature and further stirred at this temperature for 45 min before being added over 1 h to the previously prepared solution of the dianion of 4-biphenylacetic acid 2. The solution is warmed to 5° C. and stirred for 15 h before being quenched by addition to 1 M aqueous HCl (240 mL). The reaction mixture is stirred for 30 min, then extracted with isopropyl acetate (2×200 mL). The organic layer is dried over sodium sulfate, filtered and concentrated in vacuo to provide compound 7 as crude product.

Overview III:

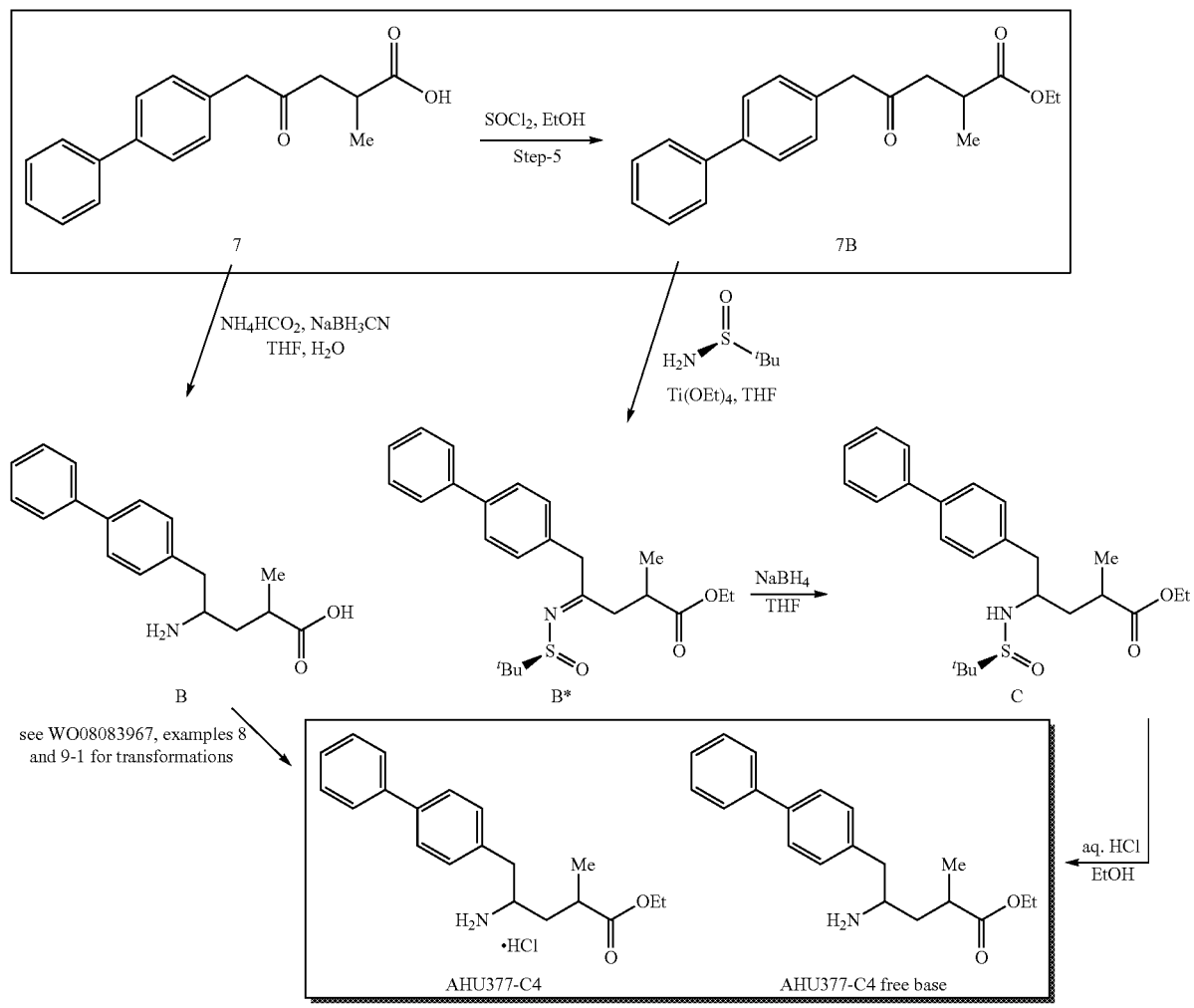

Example 8: Manufacture of 5-([1,1'-biphenyl]-4-yl)-4-amino-2-methylpentanoic Acid B Ammonium acetate (1.45 g, 18.81 mmol) was added to a solution of 5-([1,1'-biphenyl]-4-yl)-2-methyl-4-oxopentanoic acid 7 (242 mg, 0.857 mmol) in a mixture of THF and water (1:1 V/V, 2.5 mL) at room temperature. The yellow suspension was treated with sodium cyanoborohydride (58 mg, 0.923 mmol) and stirred at 40° C. over night. Aqueous 6 M hydrochloric acid (5 mL) was added slowly to control the gas evolution, followed by addition of ethyl acetate (8 mL). The phases were separated, and the organic layer was concentrated under reduced pressure. Ethyl acetate was added to the residue, and the solvent was removed under reduced pressure to give the corresponding hydrochloride salt of 5-([1,1'-biphenyl]-4-yl)-4-amino-2-methylpentanoic acid B as a beige solid (250 mg, 91.2%, dr 45:55 favoring the syn-isomer).

$^1$H-NMR (400 MHz, DMSO-d6, syn-isomer): δ 12.35 (br. s, 1H), 8.24 (br. s, 3H), 7.64-7.68 (m, 4H), 7.44-7.48 (m, 2H), 7.33-7.37 (m, 3H), 3.09 (dd, 1H), 2.89 (dd, 1H), 2.65 (ddq, 1 H), 1.93 (ddd, 1H), 1.48 (ddd, 1H), 1.01 (d, 3H);
$^1$H-NMR (500 MHz, DMSO-d6, anti-isomer): δ 12.31 (br. s, 1H), 8.19 (br. s, 3H), 7.64-7.68 (m, 4H), 7.44-7.48 (m, 2H), 7.34-7.38 (m, 3H), 3.42 (br. s, 1H), 3.05 (dd, 1H), 2.89 (dd, 1H), 2.65 (ddq, 1H), 1.86 (ddd, 1H), 1.58 (ddd, 1H), 1.06 (d, 3H) ppm; MS (ES-API): positive mode 284.1 [M+H]$^+$.

Example 9: (2R,4S)-ethyl 5-([1,1'-biphenyl]-4-yl)-4-amino-2-methylpentanoate (AHU377-C$_4$)

To a solution of (R)-ethyl 5-([1,1'-biphenyl]-4-yl)-2-methyl-4-oxopentanoate (100 mg, 0.322 mmol) in THF (5 mL) at room temperature was added (S)-2-methylpropane-2-sulfinamide (43 mg, 0.355 mmol, Sigma-Aldrich, catalogue no. 497401), followed by titanium ethoxide (294 mg, 1.289 mmol). The reaction mixture was stirred at reflux for 12 h, then cooled and added dropwise at 0° C. to a suspension of sodium borohydride (37 mg, 0.978 mmol) in THF (5 mL). The reaction mixture was further stirred at room temperature for 1 h, then cooled to 0° C. Aqueous 3 M hydrochloric acid (20 mL) was added, and the phases were separated. The organic layer was dried over Na$_2$SO$_4$, filtered and concentrated in vacuo. The residue was dissolved in ethanol (3 mL), followed by addition of aqueous 6 M hydrochloric acid (2 mL). The reaction mixture was subsequently heated to 120° C. in the microwave for 30 min. After concentration in vacuo, the residue was taken up in water and dichloromethane. The phases were separated, and the organic layer was purified by preparative TLC to provide ethyl 5-([1,1'-biphenyl]-4-yl)-4-amino-2-methylpentanoate (AHU377-C₄) (20 mg, 19.9%; (2R,4S):(2S,4R):(2S,4S):(2R,4R) 52:10:11:27) as a mixture of diastereoisomers, with the desired (2R,4S)-ethyl 5-([1,1'-biphenyl]-4-yl)-4-amino-2-methylpentanoate as the major isomer.

¹H-NMR (400 MHz, DMSO-d6, (2R,4S)-isomer as hydrochloride salt): δ 8.30 (br. s, 3H), 7.64-7.68 (m, 4H), 7.44-7.48 (m, 2H), 7.34-7.37 (m, 3H), 3.98 (q, 2H), 3.38 (dddd, 1H), 3.09 (dd, 1H), 2.82 (dd, 1H), 2.76 (ddq, 1H), 1.86 (ddd, 1H), 1.62 (ddd, 1H), 1.09 (t, 3H), 1.07 (d, 3H) ppm; MS (ES-API): positive mode 312.4 [M+H]⁺.

Overview IV:

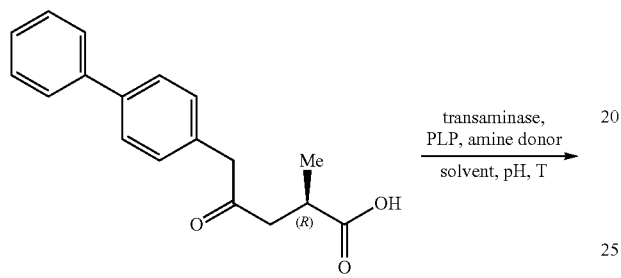

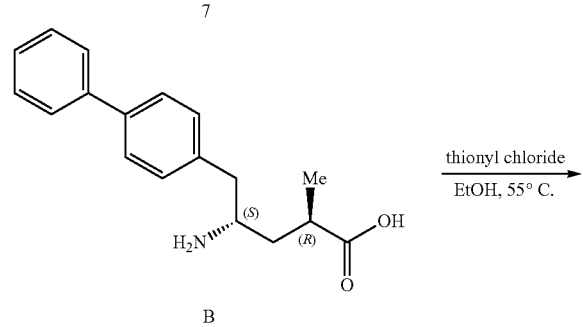

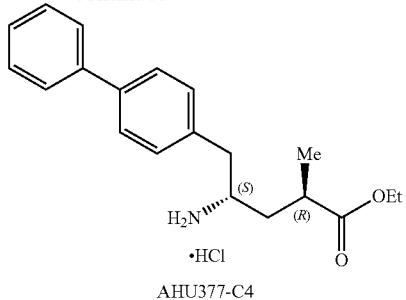

Example 10: (2R,4S)-5-([1,1'-biphenyl]-4-yl)-4-amino-2-methylpentanoic Acid B Isopropylamine hydrochloride (19.95 g, 208.8 mmol) were dissolved in aqueous 0.1 M K₂HPO₄ solution (100 mL; pH 9.36), then pyridoxal 5'-phosphate (PLP) (27 mg) was added. The pH value was adjusted to pH 9.00 by addition of isopropylamine. (R)-5-([1,1'-Biphenyl]-4-yl)-2-methyl-4-oxopentanoic acid 7 (40 mg, 0.142 mmol) was suspended in 1800 μL of this buffer solution and suspended using ultrasound for 2 min, followed by adjustment to pH 9.00 by addition of isopropylamine. The transaminase ATA-447 (30 mg; Codexis Inc., Redwood City, Calif., USA) was dissolved in 200 μL of the buffer solution and shaken for 5 min, then added to the reaction mixture. The reaction mixture was shaken at 50° C. and 180 rpm for 5 d, providing 78% conversion to the desired product B with >99:1 dr.

Overview V:

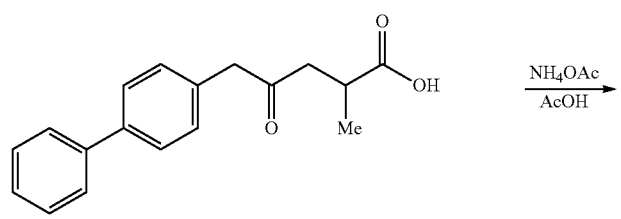

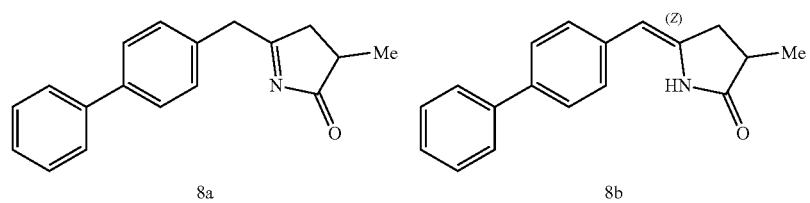

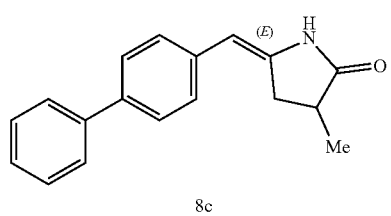 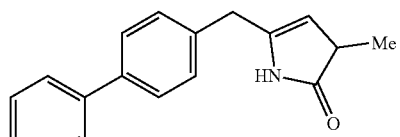

8c                    8d mixture of double bond isomers,
structures assigned based on LCMS analysis Pd/C, H$_2$
MeOH

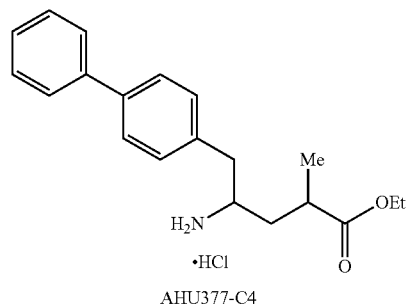

AHU377-C4

WO 08/083967 A,
Examples 7 and 13

9

Example 11: Manufacture of 5-([1,1'-biphenyl]-4-ylmethyl)-3-methylpyrrolidin-2-one Ammonium acetate (3.32 g, 43.07 mmol) was added to a solution of 5-([1,1'-biphenyl]-4-yl)-2-methyl-4-oxopentanoic acid (1.52 g, 5.38 mmol) in acetic acid (18 mL) to provide a suspension in a pressure-resistant microwave vial which was immediately sealed. The vial was placed in an oil bath at room temperature and was subsequently heated to 130° C. After 17 h, the vial was cooled back to room temperature prior to opening, and the yellow solution was separated between methylene dichloride (30 mL) and 0.1 M dipotassium hydrogen phosphate solution (30 mL of a solution of 1.74 g in 100 mL water). The aqueous phase was washed with methylene dichloride and the combined organic phases extracted twice with 1 M dipotassium hydrogen phosphate solution (30 mL of a solution of 17.4 g in 100 mL water). The organic phase was dried over solid sodium sulphate and the solvent stripped by rotary evaporation to give a yellow solid (1.35 g, 95% crude yield).

$^1$H-NMR (400 MHz, CDCl$_3$-d) ppm 1.20-1.40 (m, 5H) 1.93 (t, 3H) 2.62 (s, 1H) 2.69-2.85 (m, 3H) 2.94 (dd, 2H) 3.37 (ddd, 1H) 4.25-4.31 (m, 1H) 5.96 (t, 1H) 6.59 (br. s, 1H) 6.75 (s, 1H) 7.27-7.49 (m, 14H) 7.52-7.67 (m, 11H) 8.32 (br. s, 1H)

LC-MS (column: ACQUITY UPLC® HSS T3 1.8 µm; column temperature: 60.0° C.; 1.0 mL/min flow rate; gradient from 5% to 98% B in 9.4 min; eluent A: water+0.05% formic acid+3.75 mM acetic acid; eluent B: acetonitrile+0.04% formic acid); three major signals, all m/z correspond to pyrrolidone product mass: 3.92 min (27%); 4.34 min (64%); 4.66 min (9%).

Palladium on charcoal (4 mg, 10% Johnson-Matthey DLR 0462) was added to a solution of the crude mixture from the prior experiment (0.2 g, 0.76 mmol) in methanol (2 mL). The suspension was sealed and the headspace flushed repeatedly with nitrogen followed by hydrogen gas, finally attaining a pressure of 4 bar. The reaction was left to stir for 4.5 h at room temperature, followed by a period of 24 h at 130° C. Upon release of pressure and flushing the headspace with nitrogen the product mixture was filtered to remove catalyst, and then subjected to HPLC analysis.

HPLC (ReproShell C18, 75 mm×3 mm; column temperature 35° C.; 0.8 mL/min flow rate; eluent A: 5 mmol NaH$_2$PO$_4$, adjusted with H$_3$PO$_4$ to pH 3; eluent B: acetonitrile/methanol 2:3; gradient from 15% to 95% B). The relative stereoselectivity was compared to available reference compounds, indicating a ratio of 56:44 for trans- to cis-isomer of compound 9.

Overview IV:

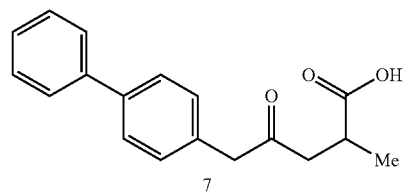

7

1. H$_2$NOH•HCl, pyridine
ethanol, reflux
2. cat. TsOH•H$_2$O
toluene, 80° C.

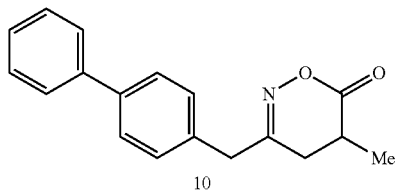

10

H$_2$, homogeneous or
heterogenous catalyst

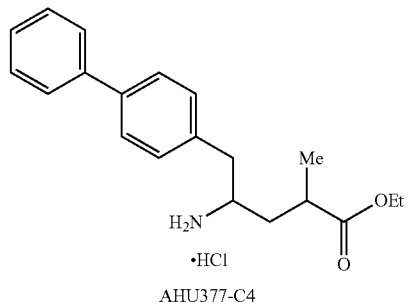

AHU377-C4

←WO 08/083967 A,
Examples 8 and 9-1

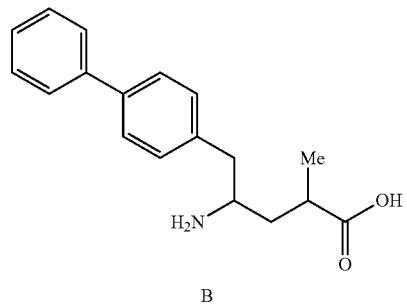

B

Example 12: Manufacture of 3-([1,1'-biphenyl]-4-ylmethyl)-5-methyl-4H-1,2-oxazin-6(5H)-one Pyridine (10.4 mL, 128.3 mmol) was added to a suspension of 5-([1,1'-biphenyl]-4-yl)-2-methyl-4-oxopentanoic acid (10.02 g, 35.12 mmol) and hydroxylamine hydrochloride (7.00 g, 98.65 mmol) in absolute ethanol (120 mL). The reaction mixture was heated to reflux and kept at reflux for 30 min. After cooling to room temperature, the reaction mixture was concentrated in vacuo. The residue was treated with water (80 mL) and ethyl acetate (150 mL), and the phases were separated. The water layer was extracted with ethyl acetate (2×80 mL), and the combined organic layers were dried over $Na_2SO_4$, filtered and concentrated in vacuo. The residue was co-evaporated with toluene (100 mL and 50 mL) to remove residual pyridine, giving a beige-brown oil that solidified upon standing. The crude product was used directly in the next step without purification.

p-Toluenesulfonic acid monohydrate (0.756 g, 3.97 mmol) was added to a suspension of the product from the previous step in toluene (120 mL). Activated molecular sieves 4 Å (6 g), and the reaction mixture was heated to 80° C., followed by stirring at 80° C. for 2 h. Further p-toluenesulfonic acid monohydrate (0.653 g, 3.43 mmol) was added, and the reaction mixture was further stirred at 80° C. for 4 h. After cooling to room temperature, the solids were filtered off. Ethyl acetate (100 mL) was added to the filtrate, and the solution was extracted with water (3×100 mL). The combined water layers were back-extracted with ethyl acetate (80 mL). The combined organic layers were dried over $Na_2SO_4$, filtered and concentrated in vacuo to give a yellow-brownish oil. The product was recrystallized from ethyl acetate/heptane 1:1 to give 3-([1,1'-biphenyl]-4-ylmethyl)-5-methyl-4H-1,2-oxazin-6(5H)-one as a light beige solid (3.17 g, 32.0%).

$^1$H-NMR (400 MHz, DMSO-d6): δ 7.64-7.67 (m, 4H), 7.44-7.48 (m, 2H), 7.34-7.41 (m, 3H), 3.75 (s, 2H), 2.70 (ddq, 1H), 2.60 (dd, 1H), 2.46 (dd, 1H), 1.07 (d, 3H) ppm; MS (ES-API): positive mode 280.1 [M+H]$^+$.

Example 13: Manufacture of 5-([1,1'-biphenyl]-4-yl)-4-amino-2-methylpentanoic Acid A mixture of 3-([1,1'-biphenyl]-4-ylmethyl)-5-methyl-4H-1,2-oxazin-6(5H)-one (28 mg, 0.100 mmol) and 5% Pt/Al$_2$O$_3$ (6 mg; Johnson-Matthey type B301099, 20% dry weight) in methanol (3 mL) was hydrogenated at 40° C. and 3 bar hydrogen pressure for 3 h. The reaction mixture was cooled and analyzed by HPLC, showing 75% product by HPLC (dr 65:35, favoring the (2R,4R)-isomer).

The invention claimed is:

1. A process for the manufacture of the compound N-(3-carboxy-1-oxopropyl)-(4S)-(p-phenylphenylmethyl)-4-amino-(2R)-methylbutanoic acid or a salt thereof, or the compound N-(3-carboxy-1-oxopropyl)-(4S)-(p-phenylphenylmethyl)-4-amino-(2R)-methylbutanoic acid ethyl ester of formula

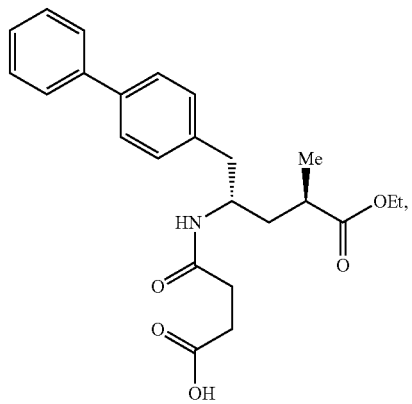 [SMILES: CCOC(=O)[C@H](C)C[C@@H](Cc1ccc(-c2ccccc2)cc1)NC(=O)CCC(=O)O]

or a salt thereof, by:

A) converting a compound of formula (I), (I)

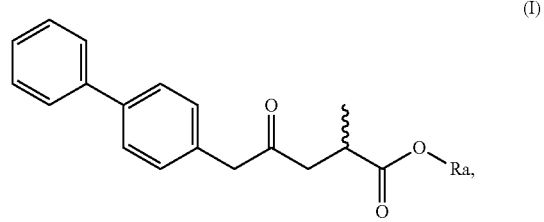

wherein:

Ra is selected from the group consisting of hydrogen, a carboxyl protecting group, and $C_1$-$C_6$-alkyl, into a compound of formula (VIII),

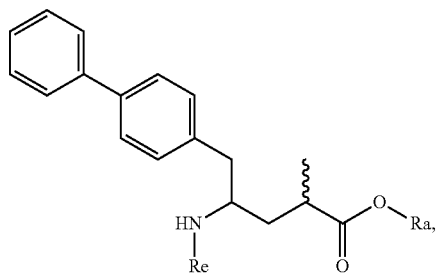

(VIII)

wherein:
Ra is selected from the group consisting of hydrogen and C$_1$-C$_6$-alkyl; and Re is selected from the group consisting of hydrogen and a nitrogen protecting group, by a process comprising any one of steps (i) to (vi):
(i) reacting a compound of formula (I), or a salt thereof;

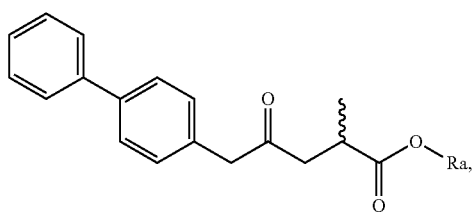

(I)

wherein: Ra is hydrogen,
with ammonia, a primary or secondary amine, or salts thereof, to provide a compound of formula (VIII), wherein Ra and Re are hydrogen, or a salt thereof; or
(ii) converting a compound of formula (I), or a salt thereof;

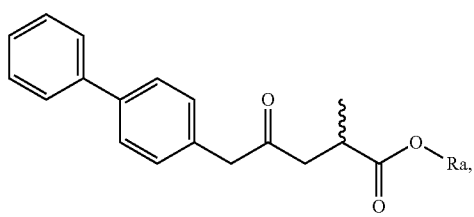

(I)

wherein:
Ra is selected from the group consisting of hydrogen and C$_1$-C$_6$-alkyl, into the compound of formula (VIII), wherein Ra is selected from hydrogen and C$_1$-C$_6$-alkyl; and Re is hydrogen, or a salt thereof, by bringing it in contact with an (S)-selective ω-transaminase in the presence of an amine donor and a coenzyme, wherein the conversion rate from the compound of formula (I) to the compound of formula (VIII), is more than 50%; or
(iii)
a) reacting a compound of formula (I), or a salt thereof;

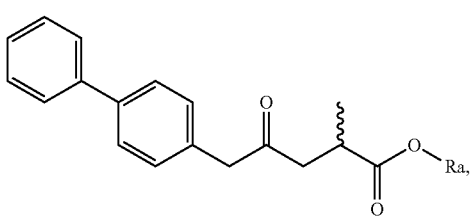

(I)

wherein:
Ra is selected from the group consisting of a carboxyl protecting group and C$_1$-C$_6$-alkyl, with an aminosulfinyl compound of formula (IX), or a salt thereof,

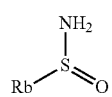

(IX)

wherein Rb is selected from the group consisting of C$_1$-C$_6$-alkyl, C$_6$-C$_{10}$-aryl, C$_6$-C$_{10}$-aryl-C$_1$-C$_6$-alkyl, C$_3$-C$_8$-cycloalkyl, C$_3$-C$_8$-cycloalkyl-C$_1$-C$_6$-alkyl, heterocyclyl, and heterocyclyl-C$_1$-C$_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)—, and S—(=O)$_2$, and wherein each aryl or heterocyclyl group can be optionally substituted by one, two or three substituents independently selected from the group consisting of halo, C$_1$-C$_7$-alkyl, halo-C$_1$-C$_7$-alkyl, C$_1$-C$_7$-alkoxy, halo-C$_1$-C$_7$-alkoxy, and C$_1$-C$_7$-alkoxy-C$_1$-C$_7$-alkyl;
to give a sulfinimide compound of the formula (X), or a salt thereof

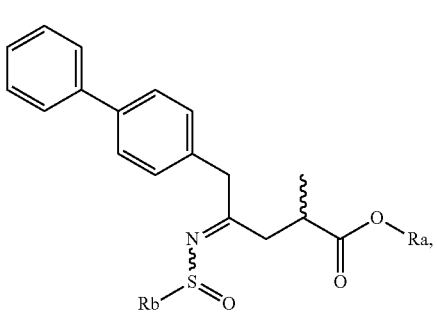

(X)

wherein:
Rb is selected from the group consisting of C$_1$-C$_6$-alkyl, C$_6$-C$_{10}$-aryl, C$_6$-C$_{10}$-aryl-C$_1$-C$_6$-alkyl, C$_3$-C$_8$-cycloalkyl, C$_3$-C$_8$-cycloalkyl-C$_1$-C$_6$-alkyl, heterocyclyl, and heterocyclyl-C$_1$-C$_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)—, and S—(=O)$_2$, and wherein each aryl or heterocyclyl group can be optionally substituted by one, two or three substituents independently selected from the group consisting halo, C$_1$-C$_7$-alkyl, halo-C$_1$-C$_7$-alkyl, and C$_1$-C$_7$-alkoxy, halo-C$_1$-C$_7$-alkoxy, and C$_1$-C$_7$-alkoxy-C$_1$-C$_7$-alkyl; and Ra is selected from a carboxyl protecting group and C$_1$-C$_6$-alkyl;

b) reducing the obtained compound of formula (X), or a salt thereof, in the presence of a reducing agent to give a sulfinamide compound of the formula (XI), or a salt thereof

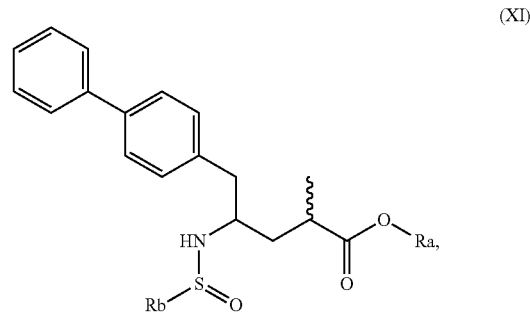

(XI)

wherein:

Rb is selected from the group consisting of C$_1$-C$_6$-alkyl, C$_6$-C$_{10}$-aryl, C$_6$-C$_{10}$-aryl-C$_1$-C$_6$-alkyl, C$_3$-C$_8$-cycloalkyl, C$_3$-C$_8$-cycloalkyl-C$_1$-C$_6$-alkyl, heterocyclyl or heterocyclyl-C$_1$-C$_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from the group consisting of halo, C$_1$-C$_7$-alkyl, halo-C$_1$-C$_7$-alkyl, C$_1$-C$_7$-alkoxy, halo-C$_1$-C$_7$-alkoxy, and C$_1$-C$_7$-alkoxy-C$_1$-C$_7$-alkyl; and Ra is selected from a carboxyl protecting group and C$_1$-C$_6$-alkyl;

c) reacting the obtained sulfinamide compound of formula (XI), or a salt thereof, by hydrolyzing the sulfonamide group in the presence of an acid to provide a compound of formula (VIII), or a salt thereof, wherein Ra is selected from the group consisting of a carboxyl protecting group and C$_1$-C$_6$-alkyl, and Re is hydrogen; and d) removing—if present—any carboxyl protecting group from the obtained compound of formula (VIII), or a salt thereof, to provide a compound of formula (VIII), or a salt thereof, wherein Ra is selected from the group consisting of hydrogen and C$_1$-C$_6$-alkyl; and Re is hydrogen; or (iv)

a) reacting a compound of formula (I), or a salt thereof;

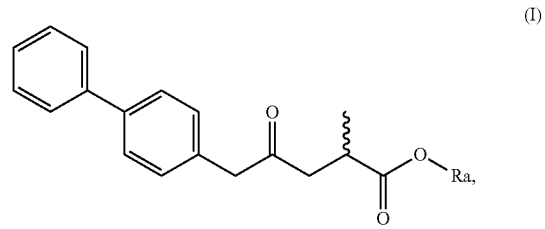

(I)

wherein Ra is hydrogen, with hydroxylamine or a salt thereof to provide a compound of formula (XVII), or a salt thereof

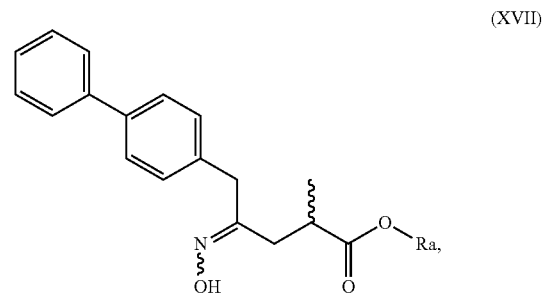

(XVII)

wherein Ra is hydrogen;

b) subsequently cyclizing the obtained compound of formula (XVII) to give the corresponding compound of the formula (XVIII)

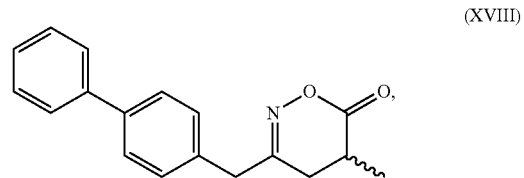 [SMILES: CC1CC(Cc2ccc(-c3ccccc3)cc2)=NOC1=O]

(XVIII)

c) reducing the obtained compound of formula (XVIII) in the presence of a reducing agent, to obtain the compound of formula (VIII), wherein Ra and Re are both hydrogen, or (v)

a) reacting a compound of formula (I), or a salt thereof;

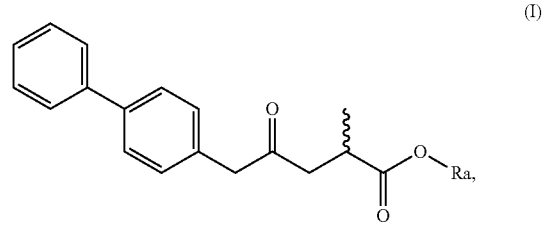

(I)

wherein Ra is hydrogen, with ammonia or an ammonium salt, yielding a compound of the formula (XIX)

83

(XIX)

b) reducing the obtained compound of formula (XIX), with a reducing agent, to give a lactam compound of formula (XX), (XX)

c) reacting the obtained compound of formula (XX) under ring opening conditions, optionally in the presence of an $C_1$-$C_7$-alcohol, to provide the compound of formula (VIII), wherein Ra is selected from the group consisting of hydrogen and $C_1$-$C_6$-alkyl; and Re is hydrogen; or (vi)
a) reacting a compound of formula (I), or a salt thereof;

(I)

wherein Ra is selected from the group consisting of hydrogen, a carboxyl protecting group and $C_1$-$C_6$-alkyl;

with an O-substituted hydroxylamine selected from or in each case a salt thereof,
wherein:
Rc and Rd are independently selected from the group consisting of $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl, and heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)—, and S—(=O)$_2$, and wherein each aryl or heterocyclyl group is optionally substituted by one, two or three substituents independently selected from the group consisting of halo, $C_1$-$C_7$-alkyl, halo-$C_1$-$C_7$-alkyl, $C_1$-$C_7$-alkoxy, halo-$C_1$-$C_7$-alkoxy, and $C_1$-$C_7$-alkoxy-$C_1$-$C_7$-alkyl;

to provide a compound of formula (XVII*), (XVII*)

wherein:
Ra is selected from the group consisting of hydrogen, a carboxyl protecting group, and $C_1$-$C_6$-alkyl; and
A is —O—C(=O)—Rc or —O-Rd;
wherein,
Rc and Rd are independently selected from the group consisting of $C_1$-$C_6$-alkyl, $C_6$-$C_{10}$-aryl, $C_6$-$C_{10}$-aryl-$C_1$-$C_6$-alkyl, $C_3$-$C_8$-cycloalkyl, $C_3$-$C_8$-cycloalkyl-$C_1$-$C_6$-alkyl, heterocyclyl, and heterocyclyl-$C_1$-$C_6$-alkyl, wherein said heterocyclyl is a mono- or polycyclic, unsaturated, partially saturated, saturated or aromatic ring system with 5 to 14 ring atoms and with one or more heteroatoms independently selected from nitrogen, oxygen, sulfur, S(=O)— or S—(=O)$_2$, and wherein each aryl or heterocyclyl group can be optionally substituted by one, two or three substituents independently selected from the group consisting of halo, $C_1$-$C_7$-alkyl, halo-$C_1$-$C_7$-alkyl, $C_1$-$C_7$-alkoxy, halo-$C_1$-$C_7$-alkoxy, and $C_1$-$C_7$-alkoxy-$C_1$-$C_7$-alkyl, b) reducing the obtained compound of formula (XVII***), or a salt thereof to provide the compound of formula (VIII) or a salt thereof, wherein Ra is selected from the group consisting of hydrogen, a carboxyl protecting group and $C_1$-$C_6$-alkyl; and Re is hydrogen; and carboxyl protecting group and $C_1$-$C_6$-alkyl, preferably ethyl, and Re is hydrogen, and c) removing—if present—any carboxyl protecting group from the obtained compound of formula (VIII), or a salt thereof;

and wherein all reaction variants (i) to (vi) are optionally followed by optionally reacting the obtained compound of formula (VIII), or a salt thereof, wherein Ra is selected from the group consisting of hydrogen and $C_1$-$C_6$-alkyl, and Re is hydrogen, with an agent introducing an amino protecting group, to provide the compound of formula (VIII), wherein Ra is selected from the group consisting of hydrogen and $C_1$-$C_6$-alkyl, and Re is a nitrogen protecting group, and/or optionally followed by reacting the compound of the formula (VIII) wherein Ra is hydrogen and Re is selected from hydrogen and a nitrogen protecting group, with a coupling reagent in the presence of an $C_1$-$C_6$-alkanol, to provide the compound of formula (VIII), wherein Ra is $C_1$-$C_6$-alkyl, and Re is a nitrogen protecting group; and B) converting the compound of formula (VIII) into the compound N-(3-carboxy-1-oxopropyl)-(4S)-(p-phenylphenylmethyl)-4-amino-(2R)-methylbutanoic-acid or a salt thereof, or the compound N-(3-carboxy-1-oxopropyl)-(4S)-(p-phenylphenylmethyl)-4-amino-(2R)-methylbutanoic acid ethyl ester or a salt thereof, by optionally removing—if present—any nitrogen protecting group Re, optionally reacting the obtained compound of formula (VIII) wherein Ra and Re are hydrogen with a coupling reagent in the presence of a $C_1$-$C_6$-alkanol, to provide the compound of formula (VIII), wherein Ra is $C_1$-$C_6$-alkyl, and Re is hydrogen, and reacting the compound of formula (VIII) wherein Ra is selected from the group consisting of hydrogen and $C_1$-$C_6$-alkyl, and Re is hydrogen, with succinic acid anhydride.

2. The process according to claim 1, wherein the compound of the formula (I), wherein Ra is selected from the group consisting of hydrogen, a carboxyl protecting group and $C_1$-$C_6$-alkyl, is prepared by reacting a compound of formula (II), or a salt thereof,

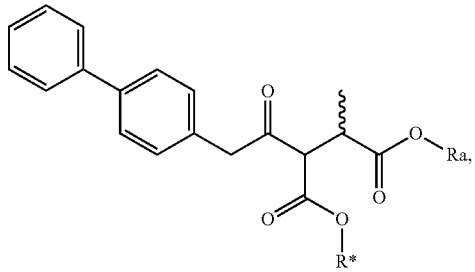

(II)

wherein:

Ra and R* are, independently of each other, selected from the group consisting of hydrogen, a carboxyl protecting group, and $C_1$-$C_6$-alkyl, under—if required—deprotection reaction conditions, followed by decarboxylation reaction conditions, and optionally by introduction of a moiety Ra selected from the group consisting of a carboxyl protecting group and $C_1$-$C_6$-alkyl, to provide the compound of formula (I).

3. The process according to claim 2, wherein the compound of the formula (II), or a salt thereof,

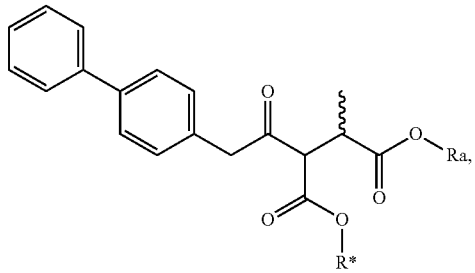

(II)

wherein:

Ra and R* are, independently of each other, selected from the group consisting of hydrogen, a carboxyl protecting group, and $C_1$-$C_6$-alkyl, is prepared by a process comprising, reacting a compound of formula (III),

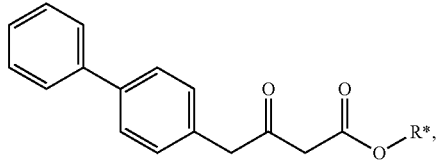

(III)

wherein:

R* is selected from the group consisting of a carboxyl protecting group and $C_1$-$C_6$-alkyl, with a propionate derivative of formula (IV),

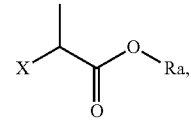

(IV)

wherein:

X is a leaving group and Ra is selected from the group consisting of a carboxyl protecting group and $C_1$-$C_6$-alkyl, and, if required, replacing the carboxyl protecting groups R* and Ra with a group selected from hydrogen and $C_1$-$C_6$-alkyl, to provide the compound of formula (II).

4. The process according to claim 3, wherein the compound of the formula (III),

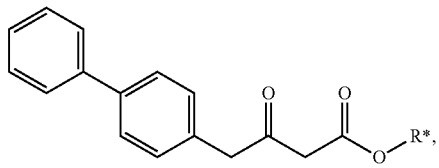

(III)

wherein R* is selected from the group consisting of a carboxyl protecting group and $C_1$-$C_6$-alkyl, is prepared by a process comprising reacting a compound of formula (V),

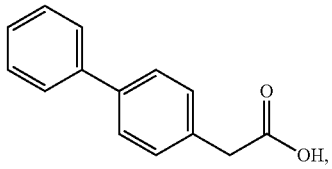

(V)

or a reactive derivative thereof, with a salt of a malonic acid half ester of formula (VI),

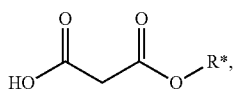

(VI)

wherein R* is selected from the group consisting of a carboxyl protecting group and $C_1$-$C_6$-alkyl.

5. The process according to claim 1, wherein the compound of the formula (I), wherein Ra is selected from the group consisting of hydrogen, a carboxyl protecting group, and $C_1$-$C_6$-alkyl, is prepared by reacting an activated dianionic derivate of the compound of formula (V), or a salt thereof,

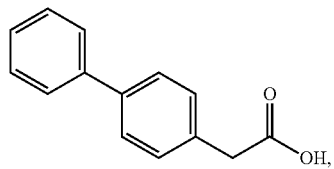

(V)

with a compound of formula (XIV), or a salt thereof,

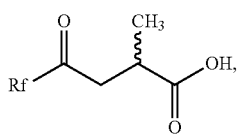

(XIV)

wherein:
Rf is selected from the group consisting of:
—O—R* wherein R* is selected from the group consisting of a carboxyl protecting group and $C_1$-$C_6$-alkyl,
—N($CH_3$)-O($CH_3$),
morpholinyl, and
imidazolinyl,
in the presence of a base, and followed by a decarboxylation reaction, to obtain compound of formula (I), or a salt thereof wherein Ra is hydrogen, optionally followed by reacting the obtained compound of formula (I), or a salt thereof, wherein Ra is hydrogen, with an agent introducing a carboxyl protecting group, to provide the compound of formula (I), wherein Ra is a carboxyl protecting group, and/or
optionally followed by reacting the compound of the formula (I), or a salt thereof, wherein Ra is hydrogen, with a coupling reagent in the presence of an $C_1$-$C_6$-alkanol, to provide the compound of formula (I), wherein Ra is $C_1$-$C_6$-alkyl.

* * * * *